US012734040B2

(12) United States Patent
Winston et al.

(10) Patent No.: US 12,734,040 B2
(45) Date of Patent: Sep. 15, 2026

(54) PATIENT-SPECIFIC SPINAL FUSION DEVICES AND ASSOCIATED SYSTEMS AND METHODS

(71) Applicant: Carlsmed, Inc., Carlsbad, CA (US)

(72) Inventors: Jeremy Winston, San Diego, CA (US); Kyle Seaman, Vista, CA (US); Josh Barkhimer, Vista, CA (US); Alexander Roeca, San Diego, CA (US); Jade Sommers, Lemon Grove, CA (US); Niall Patrick Casey, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 19/566,906

(22) Filed: Mar. 13, 2026

(65) Prior Publication Data

US 2026/0207347 A1 Jul. 23, 2026

Related U.S. Application Data

(63) Continuation of application No. 19/249,682, filed on Jun. 25, 2025, which is a continuation of application No. PCT/US2024/010202, filed on Jan. 3, 2024.

(Continued)

(51) Int. Cl.
*A61F 2/44* (2006.01)
*A61F 2/30* (2006.01)

(52) U.S. Cl.
CPC ........ *A61F 2/4455* (2013.01); *A61F 2/30749* (2013.01); *A61F 2002/30787* (2013.01); *A61F 2002/30952* (2013.01)

(58) Field of Classification Search
CPC .................................................... A61F 2/4455
See application file for complete search history.

(56) References Cited

U.S. PATENT DOCUMENTS 4,704,686 A 11/1987 Aldinger
4,936,862 A 6/1990 Walker et al.
(Continued)

FOREIGN PATENT DOCUMENTS

CN 104318009 A 1/2015
CN 104353121 A 2/2015
(Continued)

OTHER PUBLICATIONS

Endo, Kenji et al. “Measurement of whole spine sagittal alignment using the Slot radiography of the Sonialvision safire series clinical application.” Medical Now, No. 78; Aug. 2015, 4 pages.
(Continued)

*Primary Examiner* — Andrew Yang
(74) *Attorney, Agent, or Firm* — Ashurst Perkins Coie US LLP

(57) ABSTRACT

The present technology includes patient-specific spinal fusion devices, which may include an interbody implant that is designed to be positioned within a disc space between two vertebral bodies and one or more fixation elements that can anchor the interbody implant to the vertebral bodies. The fusion devices include one or more retention mechanisms for retaining the fixation elements within corresponding lumens or bore holes extending through the interbody implant. Methods for designing and manufacturing patient-specific spinal fusion devices are also described herein.

31 Claims, 23 Drawing Sheets

Related U.S. Application Data

(60) Provisional application No. 63/436,860, filed on Jan. 3, 2023.

(56) References Cited

U.S. PATENT DOCUMENTS 5,431,562 A 7/1995 Andreiko et al.
5,514,180 A 5/1996 Heggeness et al.
D420,995 S 2/2000 Imamura
D436,580 S 1/2001 Navano
6,315,553 B1 11/2001 Sachdeva
6,540,512 B1 4/2003 Sachdeva
6,696,073 B2 2/2004 Boyce et al.
6,772,026 B2 8/2004 Bradbury
6,932,842 B1 8/2005 Litschko et al.
6,978,188 B1 12/2005 Christensen
6,988,241 B1 1/2006 Guttman
7,018,415 B1 3/2006 McKay
7,174,282 B2 2/2007 Hollister et al.
7,187,790 B2 3/2007 Sabol et al.
D548,242 S 8/2007 Viegers
7,438,715 B2 10/2008 Doubler
7,662,154 B2 2/2010 Ribeiro
D614,191 S 4/2010 Takano
7,747,305 B2 6/2010 Dean et al.
7,756,314 B2 7/2010 Karau et al.
7,799,077 B2 9/2010 Lang
D633,514 S 3/2011 Tokunaga
7,972,363 B2 7/2011 Moskowitz et al.
8,118,847 B2 2/2012 Wallenstein et al.
D656,153 S 3/2012 Imamura
8,147,556 B2 4/2012 Louis et al.
8,172,885 B2 5/2012 Songer
8,177,821 B2 5/2012 Peppers
8,246,680 B2 8/2012 Betz
8,265,949 B2 9/2012 Haddad
8,273,127 B2 9/2012 Jones et al.
8,275,594 B2 9/2012 Lin
8,328,872 B2 12/2012 Duffield et al.
8,337,507 B2 12/2012 Lang
8,394,142 B2 3/2013 Bertagnoli
8,425,569 B2 4/2013 O Farrell
8,454,667 B2 6/2013 Humphreys
8,454,694 B2 6/2013 Armstrong et al.
8,457,930 B2 6/2013 Shroeder
8,480,716 B2 7/2013 Perrow et al.
8,532,806 B1 9/2013 Masson
8,556,983 B2 10/2013 Bojarski et al.
8,562,655 B2 10/2013 Butler
8,641,768 B2 2/2014 Duffield et al.
8,644,568 B1 2/2014 Hoffman
8,652,182 B1 2/2014 Walker et al.
8,709,083 B2 4/2014 Duffield et al.
8,734,516 B2 5/2014 Moskowitz et al.
8,735,773 B2 5/2014 Lang
8,758,357 B2 6/2014 Frey
8,775,133 B2 7/2014 Schroeder
8,781,557 B2 7/2014 Dean
8,795,368 B2 8/2014 Trieu
8,795,373 B2 8/2014 Jones et al.
8,814,912 B2 8/2014 Carlson
8,843,229 B2 9/2014 Vanasse
8,855,389 B1 10/2014 Hoffman
8,858,603 B1 10/2014 Zufelt
8,870,889 B2 10/2014 Frey
8,882,813 B2 11/2014 Jones et al.
8,882,840 B2 11/2014 McClintock
8,900,310 B2 12/2014 Carlson
8,932,335 B2 1/2015 Humphreys
8,940,030 B1 1/2015 Stein et al.
9,005,295 B2 4/2015 Kueenzi et al.
9,020,788 B2 4/2015 Lang
D735,231 S 7/2015 Omiya
9,078,718 B2 7/2015 Campbell
9,089,374 B2 7/2015 Peppers
D737,309 S 8/2015 Kito
9,114,023 B2 8/2015 Kana et al.
9,149,365 B2 10/2015 Lawson et al.
9,161,841 B2 10/2015 Kana et al.
9,173,689 B2 11/2015 Humphreys
9,198,678 B2 12/2015 Frey et al.
9,208,558 B2 12/2015 Dean
9,248,028 B2 2/2016 Gamache
9,265,543 B2 2/2016 Gephart
9,271,770 B2 3/2016 Costabile
9,283,091 B2 3/2016 Melkent et al.
D757,025 S 5/2016 Kim
9,326,803 B2 5/2016 Humphreys
9,364,340 B2 6/2016 Lawson et al.
9,370,435 B2 6/2016 Walkenhorst et al.
D761,842 S 7/2016 Johnson
9,381,093 B1 7/2016 Morris et al.
9,411,939 B2 8/2016 Furrer
9,445,907 B2 9/2016 Meridew
9,451,995 B1 9/2016 Olson
9,452,050 B2 9/2016 Miles et al.
9,504,584 B1 11/2016 Stein et al.
D774,076 S 12/2016 Fuller
9,526,627 B2 12/2016 Tabor
9,532,819 B2 1/2017 Campbell
9,542,525 B2 1/2017 Arisoy et al.
D779,065 S 2/2017 Brotman et al.
9,561,113 B2 2/2017 Howard
9,615,936 B2 4/2017 Duffield et al.
9,622,875 B2 4/2017 Moskowitz et al.
9,642,633 B2 5/2017 Frey et al.
9,642,652 B2 5/2017 Scioscia et al.
9,649,198 B2 5/2017 Wolters
9,675,467 B2 6/2017 Duffield et al.
9,681,959 B2 6/2017 Petersheim et al.
9,693,831 B2 7/2017 Mosnier et al.
9,707,058 B2 7/2017 Bassett
9,715,563 B1 7/2017 Schroeder
9,730,807 B2 8/2017 Donaldson
D797,760 S 9/2017 Tsujimura
D797,766 S 9/2017 Ibsies
D798,312 S 9/2017 Tsujimura
D798,455 S 9/2017 Brotman et al.
9,757,163 B2 9/2017 Jacene et al.
9,757,245 B2 9/2017 O'Neil et al.
D798,894 S 10/2017 Ibsies
9,775,680 B2 10/2017 Bojarski et al.
9,782,228 B2 10/2017 Mosnier et al.
9,848,994 B2 12/2017 Petersheim et al.
9,872,780 B2 1/2018 Reed et al.
D812,628 S 3/2018 Okado
9,907,589 B2 3/2018 Ross et al.
9,918,749 B2 3/2018 Altarac et al.
9,918,750 B2 3/2018 Tipping et al.
9,925,064 B2 3/2018 Duffield et al.
9,936,984 B2 4/2018 Blain
9,968,461 B2 5/2018 Zappacosta et al.
9,993,341 B2 6/2018 Vanasse
9,999,455 B2 6/2018 Eom
10,034,676 B2 7/2018 Donner
10,034,771 B2 7/2018 Capote et al.
D825,605 S 8/2018 Jann
D826,977 S 8/2018 Nakajima
10,045,797 B1 8/2018 Walkenhorst et al.
10,089,413 B2 10/2018 Wirx-Speetjens et al.
10,105,238 B2 10/2018 Koch et al.
10,123,884 B2 11/2018 Melkent et al.
10,130,491 B2 11/2018 Garber et al.
10,137,002 B2 11/2018 Padovani et al.
10,159,582 B2 12/2018 Gamache
D841,675 S 2/2019 Hoffman
10,213,311 B2 2/2019 Mafhouz
D845,973 S 4/2019 Jaycobs
D845,974 S 4/2019 Cooperman
D847,165 S 4/2019 Kolbenheyer
10,245,155 B2 4/2019 Petersheim et al.
10,265,109 B2 4/2019 Lauf
D848,468 S 5/2019 Ng
D849,029 S 5/2019 Cooperman
D849,773 S 5/2019 Jiang

(56) References Cited

U.S. PATENT DOCUMENTS 10,292,770 B2 5/2019 Ryan
10,299,863 B2 5/2019 Grbic et al.
D854,560 S 7/2019 Field
D854,561 S 7/2019 Field
10,390,958 B2 8/2019 Maclennan
D860,237 S 9/2019 Li
D860,238 S 9/2019 Bhardwaj
10,405,900 B2 9/2019 Ha
10,426,530 B2 10/2019 Humphreys
10,426,634 B1 10/2019 Al Jazaeri
D866,577 S 11/2019 Eisert
D867,379 S 11/2019 Ang
D867,389 S 11/2019 Jamison
10,463,433 B2 11/2019 Turner et al.
D870,762 S 12/2019 Mendoza
10,492,836 B2 12/2019 Altarac et al.
10,492,912 B2 12/2019 Gregersen
10,512,546 B2 12/2019 Kamer et al.
10,512,547 B2 12/2019 Altarac et al.
10,517,681 B2 12/2019 Roh et al.
D872,117 S 1/2020 Kobayashi
D872,756 S 1/2020 Howell
10,524,929 B2 1/2020 Shoshtaev
10,537,438 B2 1/2020 Martynova et al.
D874,490 S 2/2020 Dodsworth
D875,761 S 2/2020 Heffernan
D876,454 S 2/2020 Knowles
D876,462 S 2/2020 Li
10,548,738 B2 2/2020 Milz
10,548,743 B2 2/2020 Faulhaber
10,555,764 B2 2/2020 Gregersen
D877,167 S 3/2020 Knowles
D877,905 S 3/2020 Linder et al.
D879,112 S 3/2020 Hejazi
10,575,960 B2 3/2020 Duffield et al.
10,588,589 B2 3/2020 Bregman-Amitai et al.
10,603,055 B2 3/2020 Donner et al.
D880,513 S 4/2020 Wang
D881,908 S 4/2020 Sunil
D881,910 S 4/2020 Lin
10,621,289 B2 4/2020 Schroeder
10,631,988 B2 4/2020 Arnold et al.
D884,008 S 5/2020 Thornberg
10,646,236 B2 5/2020 Donner et al.
10,646,258 B2 5/2020 Donner et al.
10,729,556 B2 8/2020 Capote et al.
10,736,698 B2 8/2020 Bohl
10,751,188 B2 8/2020 Guo et al.
D896,825 S 9/2020 Abel
D896,828 S 9/2020 Linares
D898,054 S 10/2020 Everhart
D899,438 S 10/2020 Crafts
10,806,597 B2 10/2020 Sournac et al.
10,813,773 B2 10/2020 Gamache
10,828,075 B2 11/2020 Gault
10,869,703 B2 12/2020 Dunaway
10,902,944 B1 1/2021 Casey et al.
10,912,591 B2 2/2021 Altarac et al.
D916,868 S 4/2021 Evangeliou
D916,879 S 4/2021 Mitsumori
10,980,641 B2 4/2021 Altarac et al.
D918,253 S 5/2021 Choe
11,000,321 B2 5/2021 White
11,000,334 B1 5/2021 Young
D921,675 S 6/2021 Kmak
D921,677 S 6/2021 Kmak
D921,687 S 6/2021 Kmak
D924,909 S 7/2021 Nasu
D925,567 S 7/2021 Hayamizu
D927,528 S 8/2021 Heisler
11,076,967 B2 8/2021 Reed et al.
11,083,586 B2 8/2021 Cordonnier
11,112,770 B2 9/2021 Roh et al.
11,116,645 B2 9/2021 Zakelj
D933,692 S 10/2021 Smith
11,166,764 B2 11/2021 Roh et al.
11,173,042 B2 11/2021 Walsh et al.
11,179,246 B2 11/2021 Seifert et al.
11,185,369 B2 11/2021 Ryan
D937,870 S 12/2021 Pinto
D937,876 S 12/2021 Harvey
D938,461 S 12/2021 Hoffman
D938,986 S 12/2021 Grossberg
D940,178 S 1/2022 Ang
11,229,460 B2 1/2022 Wolfe et al.
D946,022 S 3/2022 Nuttbrown
D946,023 S 3/2022 Nuttbrown
D946,024 S 3/2022 Vogler-Ivashchanka
D946,616 S 3/2022 Tsai
11,259,937 B2 3/2022 Shi et al.
11,272,963 B2 3/2022 Wolfe et al.
11,298,244 B2 4/2022 Schultz
11,304,734 B2 4/2022 Wolfe et al.
11,304,820 B2 4/2022 Terrell et al.
D958,151 S 7/2022 Casey et al.
11,376,076 B2 7/2022 Casey et al.
11,432,943 B2 9/2022 Casey et al.
11,439,514 B2 9/2022 Casey et al.
11,443,838 B1 9/2022 Cordonnier
11,478,283 B2 10/2022 Altarac et al.
D971,411 S 11/2022 Kang et al.
11,497,559 B1 11/2022 Roh et al.
11,504,175 B2 11/2022 Bush et al.
11,510,708 B2 11/2022 Lewis et al.
11,547,457 B2 1/2023 Cordaro et al.
11,547,459 B2 1/2023 Ahn
D979,063 S 2/2023 Refai
11,612,492 B2 3/2023 McDonough et al.
11,633,290 B2 4/2023 Valkoun et al.
11,678,938 B2 6/2023 Casey et al.
D1,004,776 S 11/2023 James
11,813,006 B2 11/2023 Lauf et al.
11,854,683 B2 12/2023 Casey et al.
11,857,264 B2 1/2024 Roh et al.
11,984,205 B2 5/2024 Cordonnier
12,053,212 B2 8/2024 Afshar et al.
12,127,769 B2 10/2024 Casey et al.
12,133,803 B2 11/2024 Casey et al.
12,178,516 B2 12/2024 McAfee et al.
12,226,315 B2 2/2025 Casey et al.
12,232,980 B2 2/2025 Cordonnier
12,245,952 B2 3/2025 Casey et al.
12,251,320 B2 3/2025 Casey et al.
12,274,506 B2 4/2025 Roh et al.
12,324,746 B2 6/2025 Shin
12,427,025 B2 9/2025 Cordonnier
12,491,075 B2 12/2025 Casey et al.
12,491,085 B2 12/2025 Casey et al.
12,530,015 B2 1/2026 Roh et al.
12,575,895 B2 3/2026 Mosadegh et al.
2002/0016595 A1 2/2002 Michelson
2003/0139813 A1 7/2003 Messerli et al.
2004/0104512 A1 6/2004 Eidenschink
2004/0210314 A1 10/2004 Michelson
2005/0049590 A1 3/2005 Alleyne et al.
2005/0177245 A1 8/2005 Leatherbury et al.
2005/0234555 A1 10/2005 Sutton et al.
2005/0273170 A1 12/2005 Navarro et al.
2007/0272747 A1 11/2007 Woods et al.
2007/0276369 A1 11/2007 Allard et al.
2007/0276501 A1 11/2007 Betz
2008/0089566 A1 4/2008 Node-Langlois
2008/0227047 A1 9/2008 Lowe
2009/0062739 A1 3/2009 Anderson
2010/0191088 A1 7/2010 Anderson et al.
2010/0298942 A1 11/2010 Hansell
2010/0324692 A1 12/2010 Uthgenannt
2011/0196451 A1 8/2011 Hill
2012/0150243 A9 6/2012 Crawford et al.
2012/0322018 A1 12/2012 Lowe
2013/0079680 A1 3/2013 Stein et al.
2013/0323669 A1 12/2013 Lowe
2014/0072608 A1 3/2014 Karagkiozaki
2014/0074438 A1 3/2014 Furrer

(56) References Cited

U.S. PATENT DOCUMENTS

2014/0081659 A1 3/2014 Nawana et al.
2014/0086780 A1 3/2014 Miller
2014/0100886 A1 4/2014 Woods
2014/0164022 A1 6/2014 Reed
2014/0263674 A1 9/2014 Cerveny
2014/0277487 A1 9/2014 Davenport et al.
2014/0350614 A1 11/2014 Frey
2015/0079533 A1 3/2015 Lowe
2015/0089590 A1 3/2015 Krishnan et al.
2015/0105891 A1 4/2015 Golway et al.
2015/0199488 A1 7/2015 Falchuk
2015/0213225 A1 7/2015 Amarasingham
2015/0324490 A1 11/2015 Page
2015/0328004 A1 11/2015 Mafhouz
2015/0328005 A1 11/2015 Padovani et al.
2015/0332018 A1 11/2015 Rosen
2016/0001039 A1 1/2016 Armour et al.
2016/0015465 A1 1/2016 Steines et al.
2016/0030067 A1 2/2016 Frey et al.
2016/0074048 A1 3/2016 Pavlovskaia
2016/0081810 A1 3/2016 Reiley et al.
2016/0117817 A1 4/2016 Seel
2016/0143744 A1 5/2016 Bojarski et al.
2016/0151171 A1 6/2016 Mozeleski
2016/0184054 A1 6/2016 Lowe
2016/0210374 A1 7/2016 Mosnier et al.
2016/0217268 A1 7/2016 Otto
2016/0242857 A1 8/2016 Scholl
2016/0300026 A1 10/2016 Bogoni et al.
2016/0354039 A1 12/2016 Soto et al.
2016/0354161 A1 12/2016 Deitz
2016/0354213 A1 12/2016 Cowan
2016/0378919 A1 12/2016 McNutt et al.
2017/0000566 A1 1/2017 Gordon
2017/0014169 A1 1/2017 Dean
2017/0020679 A1 1/2017 Maclennan
2017/0035514 A1 2/2017 Fox et al.
2017/0061375 A1 3/2017 Laster
2017/0065311 A1 3/2017 George
2017/0068792 A1 3/2017 Reiner
2017/0112548 A1 4/2017 Alamin et al.
2017/0135706 A1 5/2017 Frey et al.
2017/0143494 A1 5/2017 Mahfouz
2017/0143831 A1 5/2017 Varanasi et al.
2017/0196499 A1 7/2017 Hunter
2017/0216047 A1 8/2017 Hawkes et al.
2017/0220740 A1 8/2017 D'Urso
2017/0252107 A1 9/2017 Turner et al.
2017/0262595 A1 9/2017 Vorhis
2017/0340447 A1 11/2017 Mahfouz
2017/0354510 A1 12/2017 O'Neil et al.
2017/0367645 A1 12/2017 Klinder
2018/0008349 A1 1/2018 Gillman
2018/0113992 A1 4/2018 Eltorai et al.
2018/0116727 A1 5/2018 Caldwell et al.
2018/0168499 A1 6/2018 Bergold
2018/0168731 A1 6/2018 Reid
2018/0185075 A1 7/2018 She
2018/0233222 A1 8/2018 Daley
2018/0233225 A1 8/2018 Experton
2018/0250075 A1 9/2018 Cho
2018/0271602 A1 9/2018 Frey et al.
2018/0301213 A1 10/2018 Zehavi et al.
2018/0303552 A1 10/2018 Ryan
2018/0303616 A1 10/2018 Bhattacharyya et al.
2018/0308569 A1 10/2018 Luellen
2018/0318100 A1 11/2018 Altarac
2018/0338841 A1 11/2018 Miller et al.
2019/0029842 A1 1/2019 Xiao et al.
2019/0065685 A1 2/2019 Pickover
2019/0069956 A1 3/2019 Ryan et al.
2019/0099221 A1 4/2019 Schmidt et al.
2019/0105170 A1 4/2019 Wang et al.
2019/0133783 A1 5/2019 Unger et al.
2019/0201106 A1 7/2019 Siemionow
2019/0262084 A1 8/2019 Roh et al.
2019/0266597 A1 8/2019 Mohtar
2019/0328929 A1 10/2019 Kugler et al.
2019/0333622 A1 10/2019 Levin
2019/0354693 A1 11/2019 Yoon
2019/0380792 A1 12/2019 Poltaretskyi et al.
2019/0388131 A1 12/2019 Mehl et al.
2020/0015980 A1 1/2020 McDonough
2020/0021570 A1 1/2020 Lin
2020/0046511 A1 2/2020 Singh
2020/0078180 A1 3/2020 Casey et al.
2020/0085509 A1 3/2020 Roh et al.
2020/0138523 A1 5/2020 Greenwald
2020/0246162 A1 8/2020 Schultz et al.
2020/0258605 A1 8/2020 Blechman
2020/0261156 A1 8/2020 Schmidt
2020/0281736 A1 9/2020 Milz
2020/0289288 A1 9/2020 Müller et al.
2020/0315708 A1 10/2020 Mosnier et al.
2020/0323654 A1 10/2020 Marrapode
2021/0015524 A1 1/2021 Montello et al.
2021/0015627 A1 1/2021 Weiman
2021/0064605 A1 3/2021 Balint
2021/0068796 A1 3/2021 Predick
2021/0068975 A1 3/2021 Choi et al.
2021/0077268 A1 3/2021 Struck et al.
2021/0085482 A1 3/2021 Flickinger et al.
2021/0085483 A1* 3/2021 MacMillan ........... A61F 2/4455
2021/0145519 A1 5/2021 Mosnier et al.
2021/0169576 A1 6/2021 Ryan et al.
2021/0192759 A1 6/2021 Lang
2021/0209757 A1 7/2021 Min et al.
2021/0236176 A1 8/2021 Lewis et al.
2021/0236297 A1 8/2021 Sanders et al.
2021/0287770 A1 9/2021 Anderson
2021/0338289 A1 11/2021 Afshar et al.
2021/0346168 A1 11/2021 Padovani et al.
2021/0401587 A1 12/2021 Zakelj
2022/0000635 A9 1/2022 Flickinger
2022/0006642 A1 1/2022 Maj et al.
2022/0013211 A1 1/2022 Steinberg et al.
2022/0015918 A1* 1/2022 Parr ........................ A61F 2/442
2022/0023063 A1 1/2022 Burkhardt et al.
2022/0047402 A1 2/2022 Casey et al.
2022/0054277 A1 2/2022 Seifert
2022/0071774 A1 3/2022 Walsh et al.
2022/0096246 A1 3/2022 Valkoun et al.
2022/0133489 A1 5/2022 Moskowitz et al.
2022/0160518 A1 5/2022 Casey et al.
2022/0241088 A1 8/2022 Giri
2022/0401150 A1 12/2022 Cordonnier
2022/0409140 A1 12/2022 Cordonnier
2023/0014384 A1 1/2023 Cordonnier
2023/0023440 A1 1/2023 Casey et al.
2023/0034731 A1 2/2023 Cordonnier
2023/0067537 A1 3/2023 Casey et al.
2023/0136813 A1 5/2023 Cordonnier
2023/0360768 A1 11/2023 Shannon et al.
2023/0372113 A1 11/2023 Pointillart et al.
2023/0372122 A1 11/2023 Martin et al.
2024/0225705 A1 7/2024 Flint et al.
2024/0350179 A1 10/2024 Wolfe et al.
2024/0374395 A1 11/2024 Padovani et al.
2025/0072946 A1 3/2025 Blain et al.
2025/0099263 A1 3/2025 Seaman et al.
2025/0127626 A1 4/2025 Walters et al.
2025/0177170 A1 6/2025 Cordonnier
2025/0235324 A1 7/2025 Casey et al.
2025/0318936 A1 10/2025 Winston et al.

FOREIGN PATENT DOCUMENTS

CN 204468348 U 7/2015
CN 105796214 A 7/2016
CN 106202861 A 12/2016
CN 107220933 B 9/2017
CN 108670506 A 10/2018
CN 110575289 A 12/2019
CN 111281613 A 6/2020

(56) References Cited

FOREIGN PATENT DOCUMENTS

| | | | |
|---|---|---|---|
| CN | 112155792 | A | 1/2021 |
| CN | 113643790 | A | 11/2021 |
| EP | 3120796 | A1 | 1/2017 |
| WO | WO9507509 | A1 | 3/1995 |
| WO | WO2004110309 | A2 | 12/2004 |
| WO | WO2010151564 | A1 | 12/2010 |
| WO | WO2012154534 | A1 | 11/2012 |
| WO | WO2014180972 | A2 | 11/2014 |
| WO | WO2016172694 | A1 | 10/2016 |
| WO | WO2017116346 | A1 | 7/2017 |
| WO | WO2019018013 | A1 | 1/2019 |
| WO | WO2019112917 | A1 | 6/2019 |
| WO | WO2019148154 | A1 | 8/2019 |
| WO | WO2019165152 | A1 | 8/2019 |
| WO | WO2019241167 | A1 | 12/2019 |
| WO | WO2020055874 | A1 | 3/2020 |
| WO | WO2021061662 | A1 | 4/2021 |
| WO | WO2022045956 | A1 | 3/2022 |
| WO | WO2022109097 | A1 | 5/2022 |
| WO | WO2022261171 | A1 | 12/2022 |
| WO | WO2022266313 | A1 | 12/2022 |
| WO | WO2023034405 | A1 | 3/2023 |
| WO | WO2025023347 | A1 | 1/2025 |
| WO | WO2025085702 | A1 | 4/2025 |

OTHER PUBLICATIONS

International Search Report and Written Opinion for International Application No. PCT/US24/10202, mailed Jul. 16, 2024, 14 pages.

Materialise Mimics, “Efficiently turn scans into accurate virtual 3D models,” Retrieved on Nov. 1, 2019, at www. materialize.com/en/medical/software/mimics, 1 page.

Pimenta, Dr. Luiz, “Current Surgical Strategies to Restore Proper Sagittal Alignment,” Journal of Spine 2015, vol. 4, Issue 4, 2 pages.

* cited by examiner

PATIENT-SPECIFIC SPINAL FUSION DEVICES AND ASSOCIATED SYSTEMS AND METHODS

CROSS-REFERENCE TO RELATED APPLICATIONS

This application is a continuation of U.S. patent application Ser. No. 19/249,682, filed on Jun. 25, 2025, which is a continuation of International Patent Application No. PCT/US2024/010202, filed on Jan. 3, 2024, which claims priority to U.S. Provisional Application No. 63/436,860, filed Jan. 3, 2023, the contents of which are incorporated herein by reference in their entireties.

TECHNICAL FIELD

The present disclosure is generally related to medical care, and more particularly to patient-specific medical implants, including systems and methods designing and manufacturing the same.

BACKGROUND

Surgical procedures to implant orthopedic implants are used to correct numerous different maladies in a variety of contexts, including spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma. Spine surgery itself may encompass a variety of procedures and targets, such as one or more of the cervical spine, thoracic spine, lumbar spine, or sacrum, and may be performed to treat a deformity or degeneration of the spine and/or related back pain, leg pain, or other body pain. Common spinal deformities that may be treated using an orthopedic implant include irregular spinal curvature such as scoliosis, lordosis, or kyphosis (hyper- or hypo-), and irregular spinal displacement (e.g., spondylolisthesis). Other spinal disorders that can be treated using an orthopedic implant include osteoarthritis, lumbar degenerative disc disease or cervical degenerative disc disease, lumbar spinal stenosis, and cervical spinal stenosis.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1:
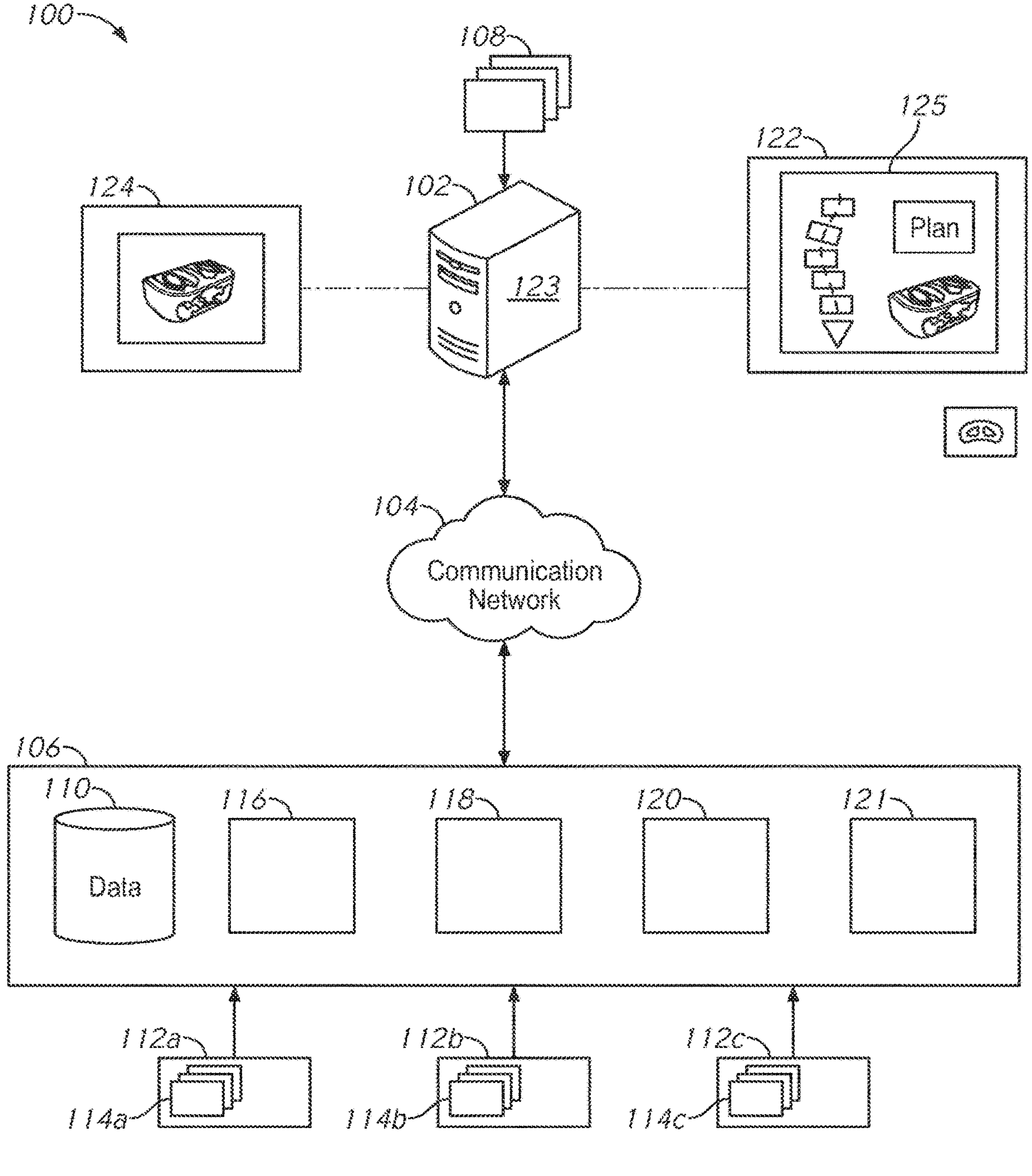
FIG. 1 is a network connection diagram illustrating a system for providing patient-specific medical care in accordance with embodiments of the present technology.

The present technology includes patient-specific spinal fusion devices. In many embodiments, the fusion devices include an interbody implant that is designed to be positioned within a disc space between two vertebral bodies to promote fusion thereof. The fusion devices can further include one or more fixation elements that can anchor the interbody implant to the vertebral bodies. In many of the embodiments described herein, the fusion devices include one or more retention mechanisms for retaining the fixation elements within corresponding lumens or bore holes extending through the interbody implant. The retention mechanisms can be advantageously designed to include certain features that restrict rotation of the retention mechanisms along a predefined path and through incremental, predefined positions. Without intending to be bound by theory, such features are expected to improve the performance of the retention mechanisms, such as by simplifying the process of the locking the retention mechanism and reducing inadvertent unlocking of the retention mechanism. Examples of patient-specific spinal fusion devices are described in detail throughout this Detailed Description, including in Section C below.

In some embodiments, the present technology includes methods of manufacturing the patient-specific spinal fusion devices. The method can include obtaining a virtual model of spinal fusion device. Manufacturing instructions can be generated based on the virtual model. A manufacturing machine can execute the manufacturing instructions to manufacture the spinal fusion device. In many embodiments, the method can include forming, via additive and/or subtractive manufacturing, a spinal fusion body, retention mechanism(s), instruments, or the like. The retention mechanism(s) can be manufactured based on the design of the spinal fusion body. In many embodiments, the spinal fusion body can be one-piece unitary spacer body. The retention mechanism(s) can be configured to be captively held by and rotatable relative to the one-piece unitary spacer body to anchor the implant to bony tissue. Examples of methods of manufacturing patient-specific spinal fusion devices are described in detail throughout this Detailed Description, including in Section D below.

In some embodiments, the present technology includes systems and methods for designing patient-specific surgical plans. This may include, for example, designing patient-specific spinal fusion devices to be implanted in a patient in accordance with the patient-specific surgical plan. Examples of systems and methods for designing patient-specific surgical plans, including designing patient-specific spinal fusion devices, are described in detail throughout this Detailed Description, including in Sections A and B below.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

The headings are provided for convenience only and should not be used to interpret the scope of the present technology.

A. SELECT EMBODIMENTS OF SYSTEMS FOR DESIGNING PATIENT-SPECIFIC SURGICAL PLANS AND PATIENT-SPECIFIC IMPLANTS

FIG. 1 is a network connection diagram illustrating a system 100 for providing patient-specific medical care, according to embodiments of the present technology. As described in further detail herein, the system 100 is configured to generate a medical treatment plan for a patient. In some embodiments, the system 100 is configured to generate a medical treatment plan for a patient suffering from an orthopedic or spinal disease or disorder, such as trauma (e.g., fractures), cancer, deformity, degeneration, pain (e.g., back pain, leg pain), irregular spinal curvature (e.g., scoliosis, lordosis, kyphosis), irregular spinal displacement (e.g., spondylolisthesis, lateral displacement axial displacement), osteoarthritis, lumbar degenerative disc disease, cervical degenerative disc disease, lumbar spinal stenosis, or cervical spinal stenosis, or a combination thereof. The medical treatment plan can include surgical information, technology recommendations (e.g., device and/or instrument recommendations), and/or medical device designs. For example, the medical treatment plan can include at least surgical procedure (e.g., a surgical procedure or intervention) and/or at least one medical device (e.g., an implanted medical device (also referred to herein as an "implant" or "implanted device") and/or implant delivery instrument). In some embodiments, the medical treatment plan is therefore also referred to as a "surgical plan," a "patient-specific surgical plan," a "patient-specific treatment plan," or the like.

In some embodiments, the system 100 generates a medical treatment plan that is customized for a particular patient or group of patients, also referred to herein as a "patient-specific" or "personalized" treatment or surgical plan. The patient-specific surgical plan can include at least one patient-specific surgical procedure and/or at least one patient-specific medical device that are designed and/or optimized for the patient's particular characteristics (e.g., condition, anatomy, pathology, condition, medical history). For example, the patient-specific medical device can be designed and manufactured specifically for the particular patient, rather than being an off-the-shelf device. However, it shall be appreciated that a patient-specific surgical plan can also include aspects that are not customized for the particular patient. For example, a patient-specific or personalized surgical procedure can include one or more instructions, portions, steps, etc. that are non-patient-specific. Likewise, a patient-specific or personalized medical device can include one or more components that are non-patient-specific, and/or can be used with an instrument or tool that is non-patient-specific. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof.

The system 100 includes a client computing device 102, which can be a user device, such as a smart phone, mobile device, laptop, desktop, personal computer, tablet, phablet, or other such devices known in the art. As discussed further herein, the client computing device 102 can include one or more processors, and memory storing instructions executable by the one or more processors to perform the methods described herein. The client computing device 102 can be associated with a healthcare provider (e.g., a surgeon, healthcare administrator, hospital system, etc.) that is treating the patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the client computing system and/or the plurality of client computing devices.

The client computing device 102 is configured to receive a patient data set 108 associated with a patient to be treated. The patient data set 108 can include data representative of the patient's condition, anatomy, pathology, medical history, preferences, and/or any other information or parameters relevant to the patient. For example, the patient data set 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient data set 108 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The client computing device 102 is also configured to enable a user (e.g., a surgeon) to review one or more proposed surgical plans for a patient to be treated. In particular, the client computing device 102 can include a surgical plan review software module 123 ("the review module 123"). The review module 123 can comprise computer-executable instructions for generating, displaying, and/or implementing a surgical plan review program or platform 125 ("the review program 125") that facilitates surgeon or user review of one or more patient-specific surgical plans via the client computing device 102.

The review module 123 can be stored in the form of computer-readable or computer-executable instructions on a memory (not shown) of the client computing device 102. In other embodiments, the review module 123 can be stored remotely from the client computing device 102 (e.g., in the cloud or at a remote server) and implemented on the client computing device 102 via a remote (e.g., wireless) connection. In yet other embodiments, some of the review module 123 can be stored locally at the client computing device 102 while other aspects of the review module 123 can be store remotely.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "treatment assistance network" or "prescriptive analytics network," can include one or more computing devices and/or systems. As discussed further herein, the server 106 can include one or more processors, and memory storing instructions executable by the one or more processors to perform some or all of the methods described herein. In some embodiments, the server 106 is implemented as a distributed "cloud" computing system or facility across any suitable combination of hardware and/or virtual computing resources.

The client computing device 102 and server 106 can individually or collectively perform some or all of the various methods described herein for providing patient-specific medical care. For example, some or all of the steps of the methods described herein can be performed by the client computing device 102 alone, the server 106 alone, or a combination of the client computing device 102 and the server 106. Thus, although certain operations are described herein with respect to the server 106, it shall be appreciated that these operations can also be performed by the client computing device 102, and vice-versa, unless the context clearly dictates otherwise.

The server 106 includes at least one database 110 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one surgical procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, pain level, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112*a*-112*c*, collectively 112). The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114*a*-114*c*, collectively 114) associated with reference patients treated by the corresponding healthcare provider. The reference patient data sets 114 can include, for example, electronic medical records, electronic health records, biomedical data sets, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

As described in further detail herein, the server 106 can be configured with one or more algorithms that generate patient-specific surgical plan data (e.g., treatment procedures, target anatomical corrections, medical devices, etc.) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning methods described herein. For example, in the depicted embodiment, the server 106 includes a data analysis module 116, a treatment planning module 118, a disease progression module 120, and an intervention timing module 121. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 116 is configured with one or more algorithms for identifying a subset of reference data from the database 110 that is likely to be useful in developing a patient-specific treatment plan. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular health-care provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific surgical plan to perform a battlefield surgery can be based on reference patient data from similar battlefield surgeries and/or data sets associated with battlefield surgeries. In another example, the patient-specific surgical plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 118 is configured with one or more algorithms to generate at least one surgical plan (e.g., pre-operative plans, intra-operative plans, post-operative plans etc.) based on the output from the data analysis module 116. In some embodiments, the treatment planning module 118 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a surgical plan will produce a favorable outcome for the particular patient. The predictive model(s) can be validated, e.g., by inputting data into the model(s) and comparing the output of the model to the expected output.

In some embodiments, the treatment planning module 118 is configured to generate the surgical plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g. implant design data) that are associated with favorable or desired treatment outcomes for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific surgical plan can be determined by selecting surgical plan(s) based on the score (e.g., higher or highest score; lower or lowest score; score that is above, below, or at a specified threshold value). The personalized patient-specific surgical plan can be based on, at least in part, the patient-specific technologies or patient-specific selected technology.

Alternatively or in combination, the treatment planning module 118 can generate the surgical plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine surgical procedure(s) and/or medical device design(s) that are optimal or likely to produce a favorable outcome for the patient to be treated.

Alternatively or in combination, the treatment planning module 118 can generate the surgical plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the surgical plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training data set can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a surgical plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one surgical plan for the patient. In some embodiments, the trained machine learning model(s) can determine candidate procedures (or candidate surgical plans), analyze the candidate procedures, select the candidate surgical plans or portions thereof, score plans, and/or generate surgical plans for the patient. Each surgical plan can be scored (e.g., scored based on favorable outcome, likelihood of outcome, etc.) and ranked according to the score. The trained machine learning model(s) can determine a set of surgical plans that meet selection criteria for plan review by a user. The selection criteria can be based on, for example, regulatory requirements, reimbursement criteria, healthcare/provider expertise, available surgical equipment, manufacturing capabilities, elimination criteria, combinations thereof, or the like. A user can input one or more selection criteria to control the types and/or features of the surgical plans for comparison. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific surgical plan generated by the treatment planning module 118 can include at least one patient-specific surgical procedure (e.g., a surgical procedure or intervention) and/or at least one patient-specific medical device (e.g., an implant or implant delivery instrument). A patient-specific surgical plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific surgical procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, removal tools, awls, drivers, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, an ALIF kit can include both standard components and patient-specific customized components. In some embodiments, the ALIF kit can include a patient specific interbody device that can be used with standard interfixating screws. In some embodiments, the generated design is for a patient-specific implant that can be used with a standard, off-the-shelf delivery instrument. For example, the implants (e.g., interbody device, screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments in which the patient-specific surgical plan includes a specific surgical procedure to implant a medical device, the treatment planning module 118 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 118 can convert the implant surgery information into formats useable for machine-learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The disease progression module 120 can be used to analyze, predict, and/or model disease progression for a particular patient. As described in detail below, the disease progression module 120 can estimate the rate of disease progression for the patient under a variety of different circumstances, including (a) if no surgical intervention occurs, and (b) if one or more surgical plans (e.g., surgical procedures identified by the treatment planning module 118) are performed. The disease progression module 120 can therefore include an algorithm, machine learning model, or other software analytical tool for predicting disease progression in a particular patient.

In some embodiments, the disease progression module 120 includes a machine learning model or other software module that can be trained based off a plurality of reference patient data sets that includes, in addition to the patient data described above, disease progression metrics for each of the reference patients. The progression metrics can include measurements for disease metrics over a period of time. Suitable metrics may include spinopelvic parameters (e.g., lumbar lordosis, pelvic tilt, sagittal vertical axis (SVA), cobb angel, coronal offset, etc.), disability scores, functional ability scores, flexibility scores, VAS pain scores, or the like. The progression of the metrics for each reference patient can be correlated to other patient information for the specific reference patient (e.g., age, sex, height, weight, activity level, diet, etc.). The disease metrics can include values over a period of time. For example, the reference patient data may include values of disease metrics on a daily, weekly, monthly, bi-monthly, yearly, or other basis. By measuring the metrics over a period of time, changes in the values of the metrics can be tracked as an estimate of disease progression and correlated to other patient data.

In some embodiments, the disease progression module 120 can therefore estimate the rate of disease progression for a particular patient. The progression may be estimated by providing estimated changes in one or more disease metrics over a period of time (e.g., X % increase in a disease metric per year). The rate can be constant (e.g., 5% increase in pelvic tilt per year) or variable (e.g., 5% increase in pelvic tilt for a first year, 10% increase in pelvic tilt for a second year, etc.). In some embodiments, the estimated rate of progression can be transmitted to a surgeon or other healthcare provider as part of a surgical plan, as described in greater detail below.

As a non-limiting example, a particular patient who is a fifty-five-year-old male may have a SVA value of 6 mm. The disease progression module 120 can analyze patient reference data sets to identify disease progression for individual reference patients having one or more similarities with the particular patient (e.g., individual patients of the reference patients who have an SVA value of about 6 mm and are approximately the same age, weight, height, and/or sex of the patient). Based on this analysis, the disease progression module 120 can predict the rate of disease progression if no surgical intervention occurs (e.g., the patient's VAS pain scores may increase 5%, 10%, or 15% annually if no surgical intervention occurs, the SVA value may continue to increase by 5% annually if no surgical intervention occurs, etc.).

The surgical treatment plans and/or associated patient-specific implants described herein can also be at least partially based on the estimated rates of disease progression, enabling the modeling of different outcomes over a desired period of times. Additionally, the models/simulations can account for any number of additional diseases or conditions to predict the patient's overall health, mobility, or the like. These additional diseases or conditions can, in combination with other patient health factors (e.g., height, weight, age, activity level, etc.) be used to generate a patient health score reflecting the overall health of the patient. The patient health score can be displayed for surgeon review and/or incorporated into the estimation of disease progression. Accordingly, the present technology can generate one or more virtual simulations of the predicted disease progression to demonstrate how the patient's anatomy is predicted to change over time. Physician input can be used to generate or modify the virtual simulation(s). The present technology can generate one or more post-treatment virtual simulations based on the received physician input for review by the healthcare provider, patient, etc.

In some embodiments, the present technology can also predict, model, and/or simulate disease progression based on one or more potential surgical plans. For example, the disease progression module 120 may simulate what a patient's anatomy and/or spinal metrics may be 1, 2, 5, or 10 years post-surgery for several different surgical plans. The simulations may also incorporate non-surgical factors, such as patient age, height, weight, sex, activity level, other health conditions, or the like, as previously described. The system and/or a surgeon can use the disease progression to aid in selecting which surgical plan provides the best long-term efficacy, as described below. These simulations can also be used to determine patient-specific corrections that compensate for the projected diseases progression.

Accordingly, in some embodiments, multiple disease progression models (e.g., two, three, four, five, six, or more) are simulated to provide disease progression data for several different surgical plans. For example, the disease progression module can generate models that predict post-surgical disease progression for each of three different surgical plans. A surgeon or other healthcare provider can review the disease progression models and, based on the review, select which of the three surgical plans is likely to provide the patient with the best long-term outcome.

Based off of the modeled disease progression, the systems and methods described herein can also (i) identify a recommended time for surgical intervention, and/or (ii) identify a recommended type of surgical procedure for the patient. In some embodiments, the present technology therefore includes an intervention timing module 121 that includes an algorithm, machine learning model, or other software analytical tool for determining the optimal time for surgical intervention in a particular patient. This can be done, for example, by analyzing patient reference data that includes (i) pre-operative disease progression metrics for individual reference patients, (ii) disease metrics at the time of surgical intervention for individual reference patients, (iii) post-operative disease progression metrics for individual reference patients, and/or (iv) scored surgical outcomes for individual reference patients. The intervention timing module 121 can compare the disease metrics for a particular patient to the reference patient data sets to determine, for similar patients, the point of disease progression at which surgical intervention produced the most favorable outcomes.

As a non-limiting example, the reference patient data sets may include data associated with reference patients'sagittal vertical axis. The data can include (i) sagittal vertical axis values for individual patients over a period of time before surgical intervention (e.g., how fast and to what degree the sagittal vertical axis value changed), (ii) sagittal vertical axis of the individual patients at the time of surgical intervention, (iii) the change in sagittal vertical axis after surgical intervention, and (iv) the degree to which the surgical intervention was successful (e.g., based on pain, quality of life, or other factors). Based on the foregoing data, the intervention timing module 121 can, based on a particular patient's sagittal vertical axis value, identify at which point surgical intervention will have the highest likelihood of producing the most favorable outcome. Of course, the foregoing metric is provided by way of example only, and the intervention timing module 121 can incorporate other metrics (e.g., lumbar lordosis, pelvic tilt, sagittal vertical axis, cobb angel, coronal offset, disability scores, functional ability scores, flexibility scores, VAS pain scores) instead of or in combination with sagittal vertical axis to predict the time at which surgical intervention has the highest probability of providing a favorable outcome for the particular patient.

The intervention timing module 121 may also incorporate one or more mathematical rules based on value thresholds for various disease metrics. For example, the intervention timing module 121 may indicate surgical intervention is necessary if one or more disease metrics exceed a predetermined threshold or meet some other criteria. Representative thresholds that indicate surgical intervention may be necessary include SVA values greater than 7 mm, a mismatch between lumbar lordosis and pelvic incidence greater than 10 degrees, a cobb angle of greater than 10 degrees, and/or a combination of cobb angle and LL/PI mismatch greater than 20 degrees. Of course, other threshold values and metrics can be used; the foregoing are provided as examples only. In some embodiments, the foregoing rules can be tailored to specific patient populations (e.g., for males over 50 years of age, an SVA value greater than 7 mm indicates the need for surgical intervention). If a particular patient does not exceed the thresholds indicating surgical intervention is recommended, the intervention timing module 121 may provide an estimate for when the patient's metrics will exceed one or more thresholds, thereby providing the patient with an estimate of when surgical intervention may become recommended.

In some embodiments, the treatment planning module 118 identifies one or more types of surgical procedures for the patient based at least in part on the disease progression of the patient determined using the disease progression module 120 and/or the intervention timing module 121. The treatment planning module 118 may also incorporate one or more mathematical rules for identifying surgical procedures. As a non-limiting example, if a LL/PI mismatch is between 10 and 20 degrees, the treatment planning module 118 may recommend an anterior fusion surgery, but if the LL/PI mismatch is greater than 20 degrees, the treatment planning module may recommend both anterior and posterior fusion surgery. As another non-limiting example, if a SVA value is between 7 mm and 15 mm, the treatment planning module may recommend posterior fusion surgery, but if the SVA is above 15 mm, the treatment planning module may recommend both posterior fusion surgery and anterior fusion surgery. Of course, other rules can be used; the foregoing are provided as examples only.

Without being bound by theory, incorporating disease progression modeling into the patient-specific surgical plans described herein may even further increase the effectiveness of the procedures and/or provide a surgeon more data by which to evaluate various surgical plans. For example, in many cases it may be disadvantageous to operate after a patient's disease progresses to an irreversible or unstable state. However, it may also be disadvantageous to operate too early, such as before the patient's disease is causing symptoms and/or if the patient's disease may not progress further. The disease progression module 120 and/or the intervention timing module 121 can therefore help identify the window of time during which surgical intervention in a particular patient has the highest probability of providing a favorable outcome for the patient.

The surgical plan(s) generated by the treatment planning module 118 can be transmitted via the communication network 104 to the client computing device 102 for output to a user (e.g., clinician, surgeon, healthcare provider, patient). In some embodiments, the client computing device 102 includes or is operably coupled to a display 122 for outputting the treatment plan(s). The display 122 can include a graphical user interface (GUI) for visually depicting various aspects of the surgical plan(s). For example, the display 122 can show various aspects of a surgical procedure to be performed on the patient, such as the surgical approach, treatment levels, corrective maneuvers, tissue resection, and/or implant placement. To facilitate visualization, the surgical plan can include a virtual model of the surgical procedure that can be displayed via the display 122. The display 122 may also display additional aspects of the surgical plan, such as predicted post-operative patient metrics, predicted disease progression metrics associated with the identified surgical procedure, etc. As another example, the display 122 can show a design for a medical device to be implanted in the patient in accordance with the transmitted surgical plan, such as a two- or three-dimensional model of the device design. The display 122 can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

In some embodiments, one or more aspects of the surgical plan are displayed using the surgical plan review program 125. For example, the review program 125, which may be implemented as a mobile phone application, a computer application, or the like, can display (e.g., via the display 122) one or more aspects of the surgical plan (e.g., a surgical procedure, a virtual model of patient anatomy, an implant, etc.). The review program 125 may provide an interactive interface that further enables a surgeon to select between different patients, select between different surgical plans for the same patient, compare surgical plans for the same patient, review the status of a surgical plan, provide feedback on a proposed surgical plan, accept a surgical plan, reject a surgical plan, etc. The review program 125 may further enable a surgeon or other user to select between different views of a virtual model of patient anatomy, and/or different views of a patient-specific implant to be used in the surgical plan.

In some embodiments, the medical device design(s) generated by the treatment planning module 118 can be transmitted from the client computing device 102 and/or server 106 to a manufacturing system 124 for manufacturing a corresponding medical device. The manufacturing system 124 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The surgical plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 118 generates control instructions configured to cause a surgical robot (e.g., robotic surgery systems, navigation systems, etc.) to partially or fully perform a surgical procedure. The control instructions can be transmitted to the robotic apparatus by the client computing device 102 and/or the server 106.

Following the treatment of the patient in accordance with the surgical plan, treatment progress can be monitored over one or more time periods to update the data analysis module 116, treatment planning module 118, disease progression module 120, and/or intervention timing module 121. Post-treatment data can be added to the reference data stored in the database 110. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116, the treatment planning module 118, the disease progression module 120, and/or the intervention timing module 121 can be components of the client computing device 102, rather than the server 106. As another example, the database 110, the data analysis module 116, the treatment planning module 118, the disease progression module 120, and/or the intervention timing module 121 can be located across a plurality of different servers, computing systems, or other types of cloud-computing resources, rather than at a single server 106 or client computing device 102.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
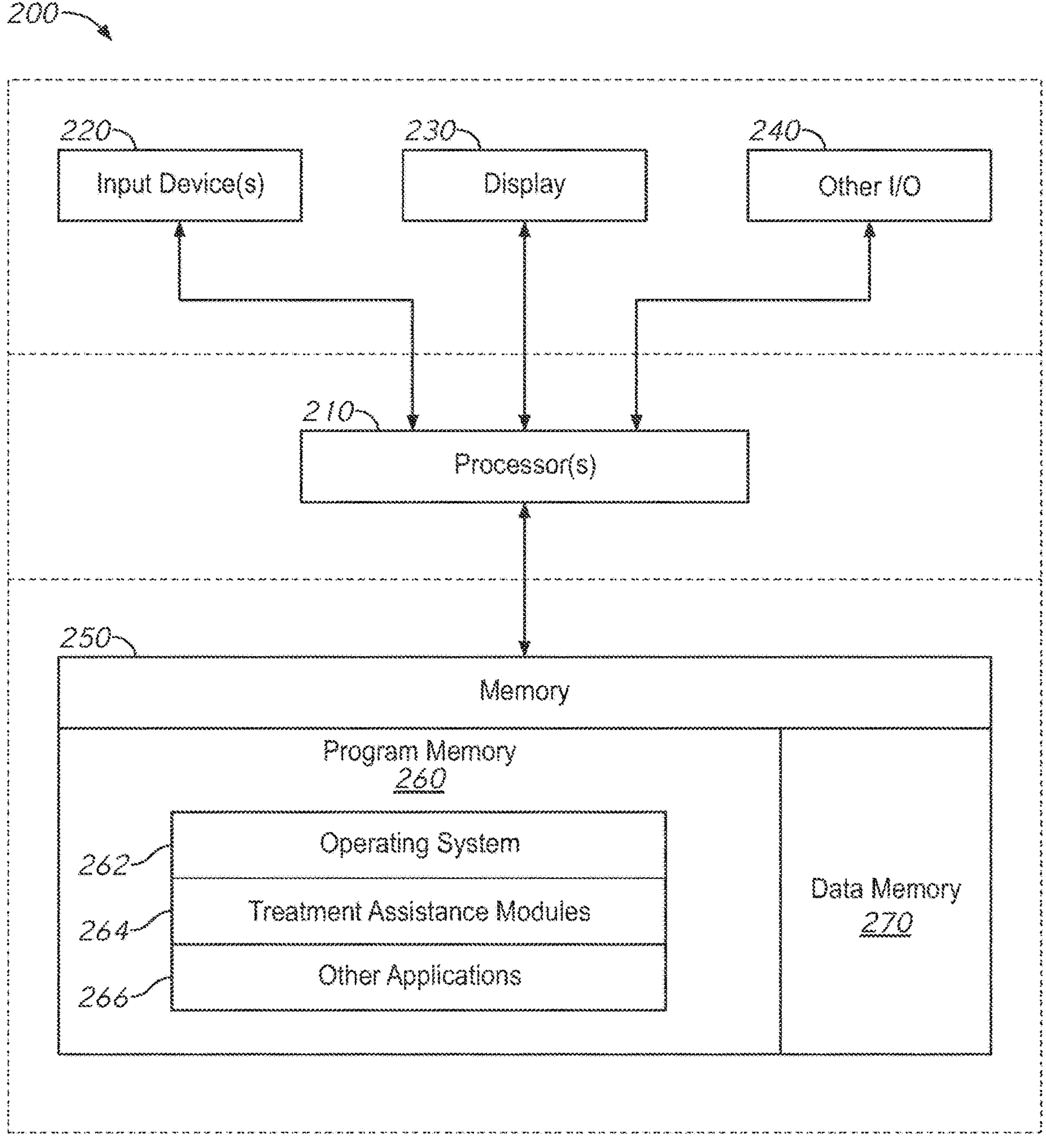
FIG. 2 illustrates a computing device suitable for use in connection with the system of FIG. 1 in accordance with embodiments of the present technology.

FIG. 2 illustrates a computing device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-Ray machines, CT machines, etc. Other I/O devices 240 can further include input ports for receiving data from these types of machine from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more treatment assistance modules 264, and other application programs 266. The treatment assistance module(s) 264 can include one or more modules configured to perform the various methods described herein (e.g., the data analysis module 116 and/or treatment planning module 118 described with respect to FIG. 1). Memory 250 can also include data memory 270 that can include, e.g., reference data, configuration data, settings, user options or preferences, etc., which can be provided to the program memory 260 or any other element of the computing device 200.

B. SELECT METHODS OF MODELING AND DESIGNING PATIENT-SPECIFIC SURGICAL PLANS AND ASSOCIATED PATIENT-SPECIFIC IMPLANTS

The present technology includes systems and methods for designing and/or generating one or more patient-specific surgical plans and associated patient specific implants. In some embodiments, the patient-specific surgical plan is for a spinal fusion surgery, and the patient-specific implant is a patient-specific fusion device. For example, the spinal fusions surgery can include an ALIF procedure, and the patient-specific implant can be a patient-specific interbody ALIF implant.

Figure 3:
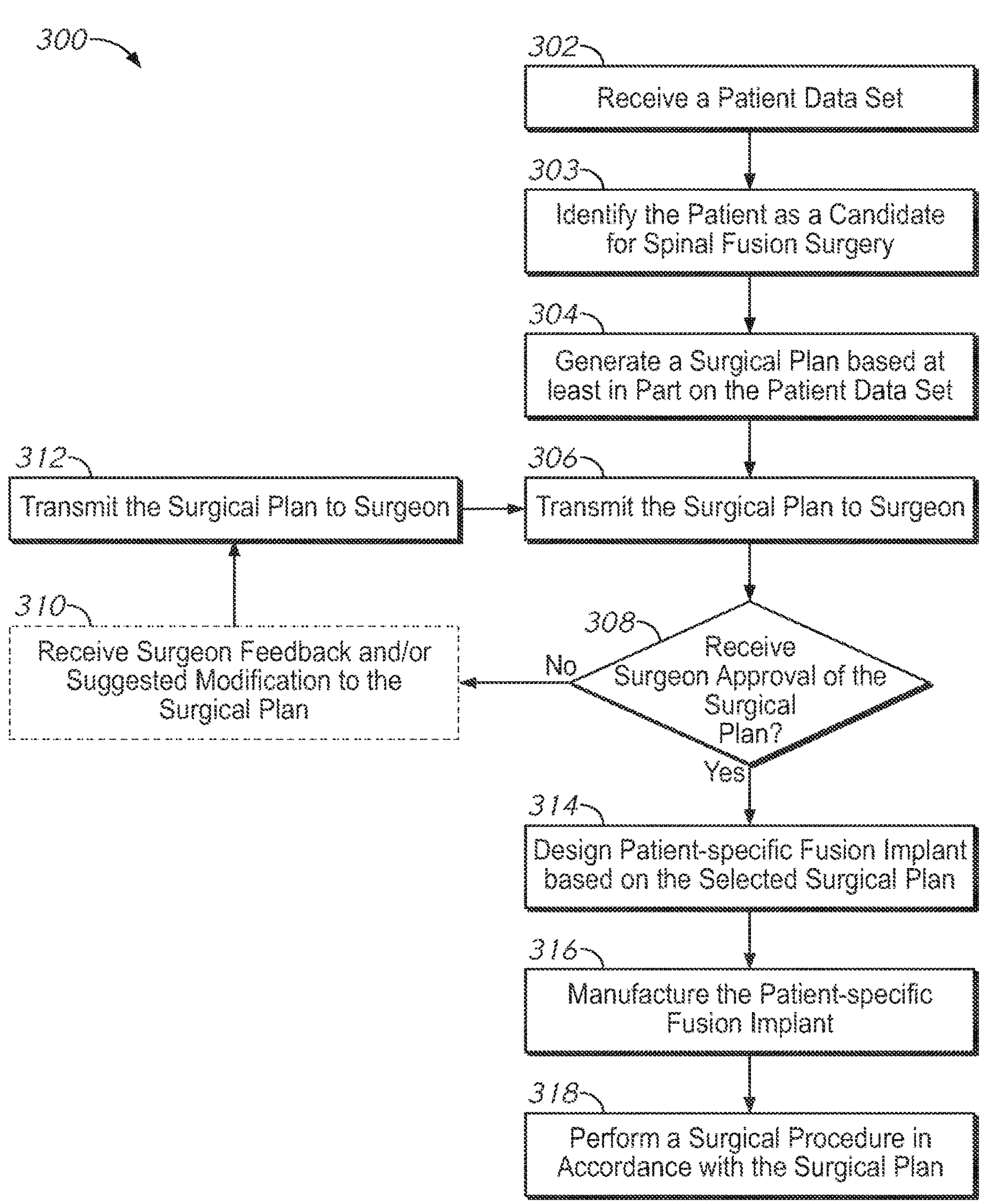
FIG. 3 is a flow diagram illustrating a method for providing patient-specific medical care in accordance with embodiments of the present technology.

FIG. 3 is a flow diagram illustrating a method 300 for providing patient-specific medical care, according to an embodiment of the present technology. Some or all of the method 300 can be performed by various computing systems or software modules, including, for example, the computing systems described above with respect to FIGS. 1 and 2.

The method 300 can begin at block 302 by receiving a patient data set for a particular patient in need of medical treatment. The patient data set can include data representative of the patient's condition, anatomy, pathology, symptoms, medical history, preferences, and/or any other information or parameters relevant to the patient. For example, the patient data set can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.) or the like. The patient data set can also include image data, such as camera images, Magnetic Resonance Imaging (MRI) images, ultrasound images, Computerized Aided Tomography (CAT) scan images, Positron Emission Tomography (PET) images, X-Ray images, and the like. In some embodiments, the patient data set includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. The patient data set can be received at a server, computing device, or other computing system. For example, in some embodiments the patient data set can be received by the server 106 shown in FIG. 1. In some embodiments, the computing system that receives the patient data set at block 302 also stores one or more software modules (e.g., the data analysis module 116, the treatment planning module 118, the disease progression module 120, and/or the intervention timing module 121, shown in FIG. 1, or additional software modules for performing various operations of the method 300).

In some embodiments, the received patient data set can include disease metrics such as lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 300 includes determining (e.g., automatically determining) one or more of the disease metrics based on the patient image data, as described below. In some embodiments, the received patient data can include functional mobility test scores (e.g., step test, six-meter walk test, sit-to-stand test, timed up and go test, etc.). The received patient data set can include additional subjective test scores that reflect aspects of the patient condition, such as pain tests (e.g., Visual Analog Scale (VAS) pain scores, Low Back Pain Rating scale scores, etc.), disability tests (e.g., Oswestry Disability Index scores, Quebec back pain disability test scores, etc.), quality of life tests (e.g., Quality of Life Scale scores), etc.

The method 300 can continue at block 303 by identifying the patient as a candidate for spinal fusion surgery. In some embodiments, the operation at block 303 includes analyzing the received patient data set from the operation in block 302 to determine whether the patient would benefit from spinal fusion surgery. In some embodiments, the operation of identifying the patient as a candidate for spinal fusion surgery can be performed by one or more treatment planning programs or modules, such as described with reference to FIG. 1.

If the patient is identified as being a candidate for spinal fusion surgery, the method 300 can continue at block 304 by generating a surgical plan based at least in part on the patient data set received at block 302. As described in detail below, the surgical plan can include a target location or region of interest for surgical intervention and one or more surgical procedures or interventions to be performed at the region of interest. The surgical plan can also include predicted post-operative data associated with performing the surgical procedure at the target location. For example, the surgical plan may include a predicted or target post-operative anatomical configuration shown as a two or three dimensional virtual model. In some embodiments, the surgical plan also includes additional predicted post-operative analytics, such as predicted disease progression, predicted patient satisfaction, predicted patient mobility, predicted patient pain, predicted patient quality of life, etc.

In some embodiments, the operation of generating the surgical plan includes identifying a specific target location to be involved in the surgical procedure. For example, in the context of spinal fusion surgery, generating the surgical plan may include identifying one or more vertebral levels for fusion. In some embodiments, the vertebral level is a lumbar vertebral level (e.g., L1-L5) and/or the sacrum. In some embodiments, the identified target location includes a specific range of vertebral levels to be involved in a surgery (e.g., L5-S1, L3-L4, etc.). The identified target location may include two, three, four, five, or more vertebral levels. Of course, the foregoing target locations are provided by way of example only, and the present technology is not limited to the anatomical locations listed above. Indeed, in some embodiments the target location may include other vertebral levels, such as cervical and/or thoracic vertebral levels, and/or anatomical structures other than the spine, such as the hip, knee, ankle, shoulder, elbow, wrist, hand, the jaw, the skull, or other anatomical locations, as described throughout this Detailed Description.

The target location can be identified by reviewing image data of the patient. In some embodiments, a computing system (e.g., the server 106 of FIG. 1) and/or one or more software modules (e.g., the treatment planning module 118 of FIG. 1) can review and analyze patient image data and automatically identify the target location. In such embodiments, a trained machine learning program or other software-based program can analyze patient image data, extract measurements from the patient image data, compare the extracted measurements to reference data (e.g., predetermined thresholds or ranges associated with "healthy" patients normalized for age, sex, gender, etc.), and identify anatomical regions that are candidates for surgical correction. Alternatively or additionally, the target location can be identified and/or confirmed through other suitable means, such as via a technician or healthcare provider reviewing image data and identifying anatomical deformities.

As provided above, in some embodiments the operation of generating the surgical plan also includes identifying a surgical procedure for the patient. In embodiments in which the surgical plan includes identifying a target location, the surgical procedure can be associated with the target location. In the context of spinal surgery, representative surgical procedures include spinal fusion, artificial disc replacement, vertebroplasty, kyphoplasty, spinal laminectomy/decompression, discectomy, facetectomy, foraminotomy, or other spine surgery procedures. Examples of spinal fusion surgery include posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). The foregoing are provided by way of example only, and the present technology can include identifying any type of spinal or other surgical procedures at block 304.

The surgical procedure associated with the surgical plan can be identified using any of the methods and systems described herein. For example, in some embodiments the server 106 of FIG. 1 and/or the associated software modules (e.g., the treatment planning module 118) can identify one or more surgical procedures based on, for example, user input, the received or extracted patient data, and/or the identified target location(s). For example, if the server 106 determines that a patient is suffering from disc degeneration from L3-L5, the server 106 may recommend an ALIF procedure to fuse L2-T12. Alternatively, the server 106 may recommend an artificial disc replacement at L3-L4 and L4-L5 to correct the degeneration while preserving motion. The surgical procedure can be identified using other methods and systems as well.

In some embodiments, the operation at block 304 can include reviewing and/or analyzing multiple types of surgical procedures and/or surgical steps to identify the surgical procedure for inclusion within the surgical plan. Types of surgical procedures and/or surgical steps can be selected for inclusion with the surgical plan (or eliminated from inclusion with the surgical plan) based on, for example, user input, insurance coverage of the procedure or step, healthcare provider parameters (e.g., based on healthcare provider ranking/scores such as hospital/physician expertise, number of similar procedures performed, hospital ranking for procedure, etc.), healthcare resource parameters (e.g., diagnostic equipment, facilities, surgical equipment such as surgical robots), and/or other non-patient related information (e.g., information that can be used to score, predict outcomes and risk profiles for procedures for the present healthcare provider, and/or rank procedures).

In some embodiments, the operation of generating the surgical plan includes identifying or designing a corrected anatomical configuration for the patient (the corrected anatomical configuration can also be referred to herein as the "planned configuration," "optimized geometry," "post-operative anatomical configuration," or "target outcome"). The corrected anatomical configuration can reflect the desired and/or predicted anatomy of the patient if the surgical plan were performed. In some embodiments, generating the surgical plan includes generating one or more virtual models (two-dimensional models, three-dimensional models, etc.) showing the corrected anatomical configuration. The virtual model may include some or all of the patient's anatomy within the target location (e.g., any combination of tissue types including, but not limited to, bony structures, cartilage, soft tissue, vascular tissue, nervous tissue, etc.). In some embodiments, the corrected anatomical configuration is identified/determined before the surgical procedure and/or target location. That is, a computing system or user can model a preferred anatomical outcome, and, based on the desired anatomical outcome, identify a surgical procedure and target location that will achieve the desired anatomical outcome once performed.

In some embodiments, generating the surgical plan includes generating one or more patient metrics associated with the corrected anatomical configuration. In the context of spinal surgery, patient metrics may include, for example, coronal parameters, sagittal parameters, pelvic parameters, Cobb angles, shoulder tilt, iliolumbar angles, coronal balance, lordosis angles, intervertebral space height, or other similar spinal parameters. Similar as described above, the patient metrics can be determined before identifying a surgical procedure and/or target location for surgical intervention. That is, a computing system or user can use the patient metrics to identify a surgical procedure and target location that will achieve the patient metrics once performed.

The surgical plan can include additional features. In some embodiments, for example, the surgical plan can include predicted disease progression, predicted patient satisfaction, predicted patient mobility, predicted patient pain, predicted patient quality of life, or the like. For example, the surgical plan may include estimates of disease progression if the patient were to undergo the identified surgical procedure at the identified target location. That is, the surgical plan can include virtual models (e.g., two-dimensional or three-dimensional virtual models) of patient anatomy at various intervals post-operation. For example, the surgical plan may include a predictive model of patient anatomy at one or more of 6 months post-op, 1 year post-op, 2 years post-op, 3 years post-op, 4 year post-op, 5 years post-op, 6 years post-op, 7 years post-op, 8 years post-op, 9 years post-op, and/or 10 years post-op. The disease progression model may also include predicted patient metrics (e.g., any of the patient metrics described herein, including coronal parameters, sagittal parameters, pelvic parameters, Cobb angles, shoulder tilt, iliolumbar angles, coronal balance, lordosis angles, intervertebral space height, or other similar spinal parameters) at any of the various post-operative intervals identified above, in addition to or in lieu of including the virtual model of predicted patient anatomy.

Once generated, the surgical plan can be digitally displayed as a surgical report on one or more display screens for ease of review, editing, annotation, the like. In some embodiments, the surgical plan can be stored as computer-executable instructions that can be executed via the surgical plan review module 123 on the client computing device 102 of FIG. 1.

In some embodiments, the operation of generating the surgical plan at block 304 includes generating a plurality of candidate surgical plans (or subsets of surgical plans such as surgical procedures), and then selecting the surgical from within the plurality of candidate surgical plans. For example, in some embodiments a computing system can automatically identify a plurality (e.g., two, three, four, five, six, seven, eight, nine, ten, or more) of surgical plans (or subsets of surgical plans such as surgical procedures) based on the patient-data set and/or one or more user-inputted criteria. The identified candidate surgical plans may be ranked and/or scored based on various factors, including predicted patient outcomes, user-review, etc. The highest ranked identified candidate surgical plans (e.g., based on predicted patient outcomes) can be selected as the surgical plan. In some embodiments, certain ranked surgical plans may not be selected as the surgical plan based on user review and/or failure to meet various user criteria. For example, if a particular surgical plan is identified as requiring a surgical procedure that the physician is unfamiliar with, the particular surgical plan may not be selected, and the method can instead include selecting the next best surgical plan as the surgical plan. Accordingly, in some implementations, physician-specific scoring is used to score candidate procedures/surgical plans before selecting the surgical plan. For example, procedures with scores meeting a threshold score (e.g., threshold post-operative metrics score, physician inputted threshold score, threshold outcome score, etc.) can be identified for user review. The system can therefore compare advantages and disadvantages of candidate procedures with respect to each other before selecting the surgical plan.

Once the surgical plan is generated at block 304, the method 300 can continue at block 306 by transmitting the surgical plan to a surgeon. In some embodiments, the same computing system used at blocks 302 and 304 can transmit the surgical plan to a computing device for surgeon review (e.g., the client computing device 102 described in FIG. 1). This can include directly transmitting the surgical plan to the computing device or uploading the first and second surgical plans to a cloud or other storage system for subsequent downloading.

The surgeon can review the surgical plan and, at block 308, approve or disapprove of the surgical plan. For example, the surgeon may review the surgical plan using the surgical plan reviewing program 125 (FIG. 1) to determine whether the surgeon deems the surgical plan acceptable. This may include, for example, reviewing the surgical plans target locations, surgical procedure, target/predicted post-operative anatomical configuration, and predicted post-operative patient metrics.

In some embodiments, the surgeon may not approve the surgical plan at block 308. In such embodiments, the surgeon can optionally provide feedback and/or suggested modifications to the surgical plan (e.g., by adjusting the virtual model or changing one or more aspects about the plan, providing comments on or more requested changes to the surgical plan, etc.). Accordingly, the method 300 can optionally include receiving (e.g., via the computing system) the surgeon feedback and/or suggested modifications at block 310. This may include, for example, modifying target locations for surgical intervention, surgical procedures, and/or target post-operative anatomical configuration. If surgeon feedback and/or suggested modifications are received at block 310, the method 300 can continue at block 312 by revising (e.g., automatically revising via the computing system) the surgical plan based at least in part on the surgeon feedback and/or suggested modifications received at block 310. In some embodiments, the surgeon does not provide feedback and/or suggested modifications if they reject the surgical plan. In such embodiments, block 310 can be omitted, and the method 300 can continue at block 312 by revising (e.g., automatically revising via the computing system) the surgical plans by selecting new and/or additional reference patient data sets and/or generating a new candidate surgical plan. The revised and/or new surgical plan can then be transmitted to the surgeon for review. The operations at blocks 306, 308, 310, and 312 can be repeated as many times as necessary until the surgeon selects and approves a particular surgical plan.

Once surgeon approval of a surgical plan is received at block 308, the method 300 can continue at block 314 by designing (e.g., via the same computing system that performed blocks 302-308) a patient-specific fusion implant based on the selected surgical plan. For example, the patient-specific fusion implant can be designed based on the target location and surgical procedure included in the selected surgical plan. The patient-specific implant(s) can also be specifically designed such that, when implanted in the particular patient at the target location using the identified surgical procedure, it directs the patient's anatomy to occupy the target post-operative anatomical configuration (e.g., transforming the patient's anatomy from the patient's native anatomical configuration to the corrected anatomical configuration). The patient-specific fusion implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, the patient-specific fusion implant is designed solely based on the virtual model of the corrected anatomical configuration and/or without reference to pre-operative patient images.

The patient-specific fusion implant can be any of the implants described herein. For example, the patient-specific fusion implant can be any of the ALIF interbody implants described in Section C of this Detailed Description. In other embodiments, the patient-specific fusion implant can include other implants, such as those described in U.S. application Ser. Nos. 16/048,167, 16/242,877, 16/207,116, 16/352,699, 16/383,215, 16/569,494, 16/699,447, 16/735,222, 16/987,113, 16/990,810, 17/085,564, 17/100,396, 17/342,329, 17/518,524, 17/531,417, 17/835,777, 17/851,487, 17/867,621, and 17/842,242, each of which is incorporated by reference herein in its entirety. The patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.). In addition to the interbody device, in some embodiments the patient-specific fusion implant can further include one or more screws (e.g., bone screws, spinal screws, pedicle screws, facet screws), cages, plates, rods, discs, spacers, expandable devices, stents, brackets, ties, scaffolds, fixation device, anchors, nuts, bolts, rivets, connectors, tethers, fasteners, or the like.

In some embodiments, designing the implant at block 316 can optionally include generating fabrication instructions for manufacturing the implant. For example, the computing system may generate computer-executable fabrication instructions that that, when executed by a manufacturing system, cause the manufacturing system to manufacture the implant.

In some embodiments, the patient-specific implant is designed at block 316 only after the surgeon has selected a surgical plan. Accordingly, in some embodiments, the implant design is neither transmitted to the surgeon with the surgical plan at block 308, nor manufactured before receiving surgeon approval of the surgical plan. Without being bound by theory, waiting to design the patient-specific implant until after the surgeon approves the surgical plan may increase the efficiency of the method 300 and/or reduce the resources necessary to perform the method 300. In other embodiments, one or more patient-specific implants can be designed and included in the surgical plans transmitted to the surgeon at block 306. For example, a virtual implant of the patient-specific fusion implant can be generated and transmitted for surgeon review concurrent with the surgical plan during the operation of block 306. Accordingly, in some embodiments the operation at block 314 can be included within the block 304.

The method 300 can continue at block 316 by manufacturing the patient-specific fusion implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively or additionally, the implant can be manufactured using subtractive manufacturing techniques, such as CNC machining, electrical discharge machining (EDM), grinding, laser cutting, water jet machining, manual machining (e.g., milling, lathe/turning), or like technologies, or combinations thereof. The implant may be manufactured by any suitable manufacturing system (e.g., the manufacturing system 124 shown in FIG. 1). In some embodiments, the implant is manufactured by the manufacturing system executing the computer-readable fabrication instructions generated by the computing system at block 316.

Once the implant is manufactured at block 316, the method 300 can continue at block 318 by performing the selected surgical plan and implanting the patient-specific fusion implant into the patient. Aspects of the surgical plan, such as some or all of the surgical procedure, can be performed manually, by a robotic surgical platform (e.g., a surgical robot), or a combination thereof. In embodiments in which the surgical procedure is performed at least in part by a robotic surgical platform, the surgical plan can include computer-readable control instructions configured to cause the surgical robot to perform, at least partly, the patient-specific surgical procedure.

The method 300 can be implemented and performed in various ways. In some embodiments, the operations at blocks 302-314 can be performed by a computing system associated with a first entity, block 316 can be performed by a manufacturing system associated with a second entity, and block 318 can be performed by a surgical provider, surgeon, and/or robotic surgical platform associated with a third entity. Any of the foregoing blocks may also be implemented as computer-readable instructions stored in memory and executable by one or more processors of the associated computing system(s).

C. SELECT EMBODIMENTS OF PATIENT-SPECIFIC SPINAL FUSION DEVICES

The systems and methods described with reference to FIGS. 1-3 can be used to design and manufacture patient-specific medical devices for use with a patient-specific surgical plan. In some embodiments, the patient-specific medical devices include a patient-specific spinal fusion device. The patient-specific spinal fusion devices can include one or more interbody implants for spinal fusion surgery, such as PLIF implants, ALIF implants, TLIF implants, LLIF implants, DLIF implants, and/or XLIF implants. In some embodiments, the patient-specific fusion devices further include, in addition to the interbody device, one or more fixation elements or screws configured to anchor the interbody device to patient anatomy. Accordingly, in some embodiments the patient-specific spinal fusion devices include at least a patient-specific interbody device and one or more screws for fixating the patient-specific interbody devices to patient anatomy.

Figure 4:
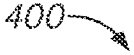
FIG. 4 is a front view of a representative patient-specific spinal fusion device configured in accordance with select embodiments of the present technology.
Figure 4:
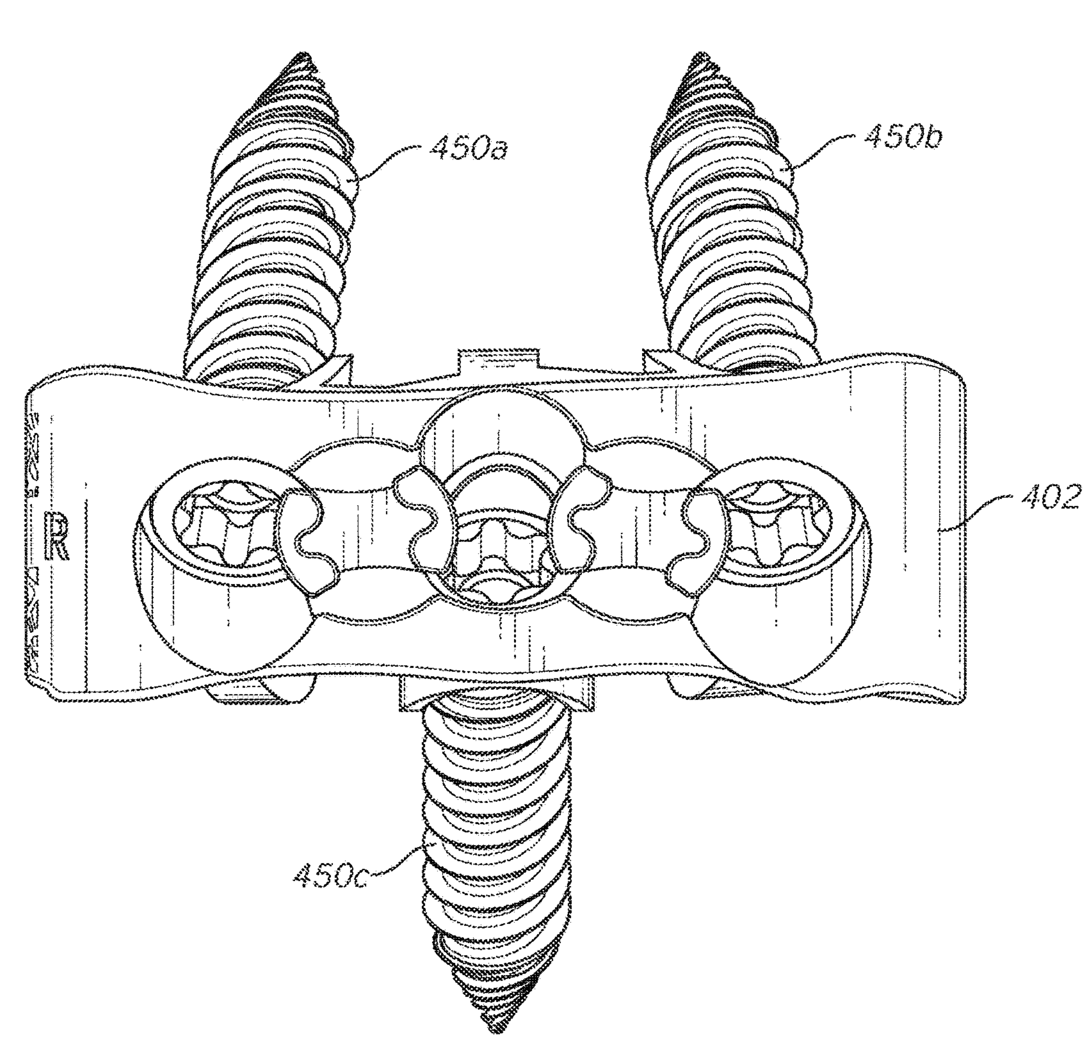

FIG. 4 is a front view of a representative patient-specific spinal fusion device 400 ("the device 400") configured in accordance with select embodiments of the present technology. The device 400 can include a patient-specific interbody implant 402 (which can also be referred to herein as an intervertebral spacer) and a plurality of fixation elements or screws. More specifically, the illustrated device 400 includes three fixation elements: a first fixation element 450*a*, a second fixation element 450*b*, and a third fixation element 450*c* (collectively referred to as "the fixation elements 450").

In operation, the device 400 can be implanted in a patient's spine to promote fusion of two or more vertebral bodies. In particular, the interbody implant 402 can be positioned within a disc space between two vertebral endplates (e.g., after a discectomy). The interbody implant 402 can be secured to the vertebral endplates using the fixation elements 450. In the illustrated embodiment, the first fixation element 450*a* and the second fixation element 450*b* are angled superiorly and posteriorly (relative to patient anatomy when the device 400 is implanted) and the third fixation element 450*c* is angled inferiorly and posteriorly (relative to patient anatomy when the device 400 is implanted). As a result, the first fixation element 450*a* and the second fixation element 450*b* are configured to anchor the interbody implant 402 to the superior vertebra and the third fixation element 450*c* is configured to anchor the interbody implant 402 to the inferior vertebra. For example, if the interbody implant 402 is positioned in the L5-S1 disc space, the first fixation element 450*a* and the second fixation element 450*b* can anchor the interbody implant 402 to the L5 vertebral body, and the third fixation element 450*c* can anchor the interbody implant 402 to the S1 vertebral body. In some embodiments, the device 400 can include more or fewer fixation elements 450, such as one, two, four, five, six, seven, or more fixation elements 450. Similarly, the fixation elements 450 can have different orientations than those shown in FIG. 4. For example, in some embodiments the device 400 can include one fixation element having a superior-posterior angle and two fixation elements having an inferior-posterior angle. As another example, the device 400 can include one fixation element having a superior-posterior angle and one fixation element having an inferior-posterior angle. Without intending to be bound by theory, anchoring the interbody implant 402 to both the superior and inferior vertebrae is expected to reduce the risk of implant expulsion from the disc space prior to fusion.

One or more aspects of the device 400 can be "patient-specific" in that they are specifically designed for use with a particular patient. Accordingly, in some embodiments the device 400 can be designed and manufactured using the systems described with reference to FIGS. 1 and 2 and/or the method described with reference to FIG. 3. In other embodiments, the device 400 can be manufactured using other suitable systems and methods that incorporate patient-specific parameters into the design of the device 400.

Figure 5A:
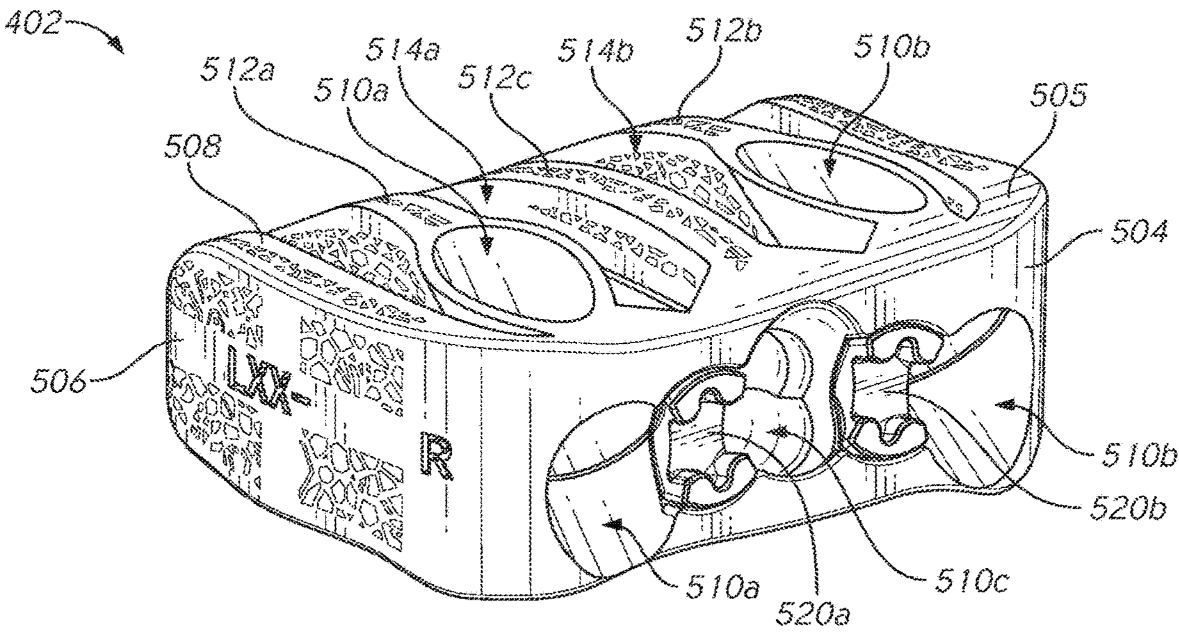
FIGS. 5A and 5B are isometric and side views, respectively, of an interbody implant of the spinal fusion device of FIG. 4 with other features omitted to more clearly illustrate features of the interbody implant.
Figure 5B:
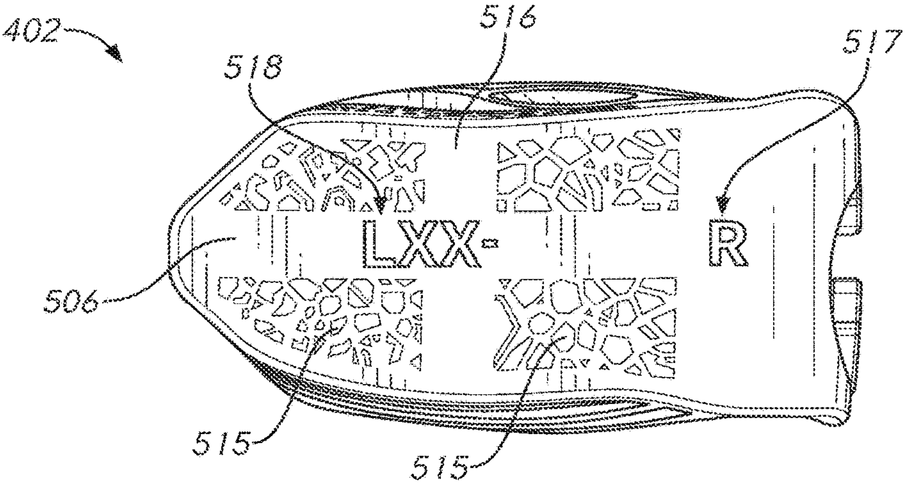

FIG. 5A is an isometric view of the interbody implant 402 of FIG. 4 with the fixation elements 450 omitted to more clearly illustrate features of the interbody implant 402, and FIG. 5B is a side view of the interbody implant 402 of FIG. 4 also with the fixation elements 450 omitted to more clearly illustrate features of the interbody implant 402. Referring first to FIG. 5A, the interbody implant 402 can include an anterior surface or face 504, a posterior surface or face (not visible in FIG. 5A) a first lateral or side surface or face 506, a second lateral or side surface or face (not visible in FIG. 5A), a superior surface or face 508, and an inferior surface or face (not visible in FIG. 5B). The implant 402 includes a first lumen 510*a*, a second lumen 510*b*, and a third lumen 510*c* (collectively referred to as lumens 510). The lumens 510 can be bore, screw, or anchor holes or channels that are configured to receive the fixation elements 450 (FIG. 4). Accordingly, each of the lumens 510 can include a first (e.g., "entry") aperture in the anterior surface 504 of the implant 402, and a second (e.g., "exit") aperture. The exit aperture can be either in the superior surface 508 or the inferior surface (not shown), depending on the angular orientation of the corresponding lumen 510. For example, in the illustrated embodiment the first lumen 510*a* and the second lumen 510*b* have exit apertures in the superior surface 508, and the third lumen 510*c* has an exit aperture in the inferior surface. The angled orientation of the lumens 510 sets the angled orientation of the fixation elements 450 (FIG. 4), and thus can be adjusted based on a desired fixation angle and/or desired fixation target.

In some embodiments, an inner surface of the lumens 510 is smooth, as opposed to rough and/or textured. In such embodiments, the inner surface of the lumens 510 can be smoothed during a specific step during manufacture of the implant 402, although in other embodiments the inner surface is relatively smooth as a result of the manufacturing process used to produce the implant 402, without the need for an additional step to smooth the inner surface. Without intending to be bound by theory, having a relatively smooth inner surface for the lumens 510 is expected to be advantageous because it reduces friction between the fixation elements 450 (FIG. 4) and the inner surface, e.g., as the fixation elements 450 are advanced through the lumens 510 and anchored to patient anatomy. Despite the relative low friction between the fixation elements 450 and the lumens 510, the fixation elements 450 can be retained within the lumens 510 via other retention mechanisms described in detail below. In some embodiments such as the embodiment described below with reference to FIGS. 11A-11E, the inner surfaces of the lumens 510 can include a thread for engaging the fixation elements 450, even in embodiments in which the surface is otherwise smooth. In some embodiments, the inner surface is a continuous surface that extends (e.g., without gaps or apertures) from the entry aperture of each lumen 510 to the exit aperture of each lumen 510.

The implant 402 can include one or more inner support walls or beams extending at least partially between the anterior surface 504 and the posterior surface. In the illustrated embodiment, for example, the implant 402 includes a first inner support wall 512*a*, a second inner support wall 512*b*, and a third inner support wall 512*c* (collectively referred to as the inner support walls 512). The inner support walls 512 can be associated with the lumens 510. That is, each lumen can be formed at least partially within a corresponding inner support wall 512. For example, the first inner support wall 512*a* can be associated with the first lumen 510*a*, the second inner support wall 512*b* can be associated with the second lumen 510*b*, and the third inner support wall 512*c* can be associated with the third lumen 510*c*. In this way, the inner support walls 512 provide structural integrity for the lumens 510.

The inner support walls 512 can be composed of solid material and/or a lattice structure. In some embodiments, the inner support walls 512 can be load bearing (e.g., in addition to the perimeter of the device being load bearing). In some embodiments, the implant 402 includes a denser load bearing portion 505 that is configured to bear a majority of loading applied by the patient's spine (e.g., when the patient stands upright). In such embodiments, a mass of the dense load-bearing portion 505 can comprise a majority of the total mass of the implant 402.

The inner support walls 512 can also at least partially define one or more chambers or openings 514 (shown as a first opening 514*a* and a second opening 514*b*) extending at least partially between the superior surface 508 and the inferior surface (not shown) of the implant 402. In operation, the openings 514 can be filled with graft material (e.g., autograft and/or allogenic bone graft comprised of cancellous and/or corticocancellous bone) to promote bone growth and fusion of the implant 402 to patient bony anatomy.

The implant 402 further includes a first retention mechanism 520*a* and a second retention mechanism 520*b* (collectively referred to as "the retention mechanisms 520") for retaining the fixation elements 450 within the lumens 510. As described in greater detail below with reference to FIGS. 6A and 6B, the retention mechanisms 520 can be selectively rotated or otherwise manipulated between a first, unlocked configuration that permits a user to insert the fixation elements 450 into the corresponding lumens 510, and a second, locked configuration that locks the fixation elements 450 in the corresponding lumens 510. Once in the locked configuration, the first retention mechanism can hold (e.g., prevent back-out of) the first fixation element 450*a* and the third fixation element 450*c* (FIG. 4) in the first lumen 510*a* and the third lumen 510*c*, respectively, and the second retention mechanism can hold the second fixation element 450*b* and the third fixation element 450*c* in the second lumen 510*b* and the third lumen 510*c*, respectively.

The implant 402 can be a patient-specific implant designed to correspond to a particular patient's anatomy. In some embodiments one or more implant surfaces can be designed to have a topography that matches (e.g., mates with) a topography of patient anatomy that the implant surface will contact once the implant 402 is implanted in the patient. For example, in embodiments in which the implant is configured for placement in the L5-S1 disc space, the superior surface 508 of the implant 402 can have a topography configured to mate with a topography of the inferior endplate of the L5 vertebral body, and the inferior surface (not shown) of the implant 402 can have a topography configured to mate with a topography of the superior endplate of the S1 vertebral body. As a result, the superior surface 508 and the inferior surface, including the portions of these surfaces surrounding the exit apertures to the lumens 510, can be irregularly contoured to match a contouring of the adjacent vertebral endplates. Also as a result, the implant 402 can be asymmetrical with respect to a mid-sagittal plane of the implant 402 and/or with respect to a transverse plane of the implant 402. Other properties of the implant (e.g., size, geometry, load-bearing characteristics, shear forces, and any other properties that can be made patient-specific as described with reference to FIGS. 1-3) can also be patient-specific.

In some embodiments, the implant 402 is a single, contiguous component (e.g., a one-piece interbody implant). For example, the implant 402 can be manufactured as a single structure using various additive manufacturing techniques, such as described below with reference to FIGS. 14-16. In some embodiments, the implant 402 is composed of metal (e.g., titanium, etc.) and/or a metal alloy (e.g., stainless steel, Nitinol, etc.). In other embodiments, the implant 402 can be composed of a biocompatible plastic. The implant 402 can also include a combination of lattice portions and solid portions. For example, as shown in FIG. 5B, the first side 506 includes lattice portions 515 and solid portions 516. The combination of lattice portions 515 and solid portions 516 can be designed based on desired implant properties, such as stiffness, load-bearing capabilities, promotion of bone growth, fit, cost, or the like.

As best shown in FIG. 5B, the implant 402 can also include one or more visual indicators for providing information to the surgeon implanting the implant 402. For example, the implant 402 includes an orientation indicator 517 (shown as "R" on the implant 402). The orientation indicator 517 can confirm the correct orientation that the implant 402 should be implanted at. For example, the "R" on the implant 402 should be located upright and on the right side of the patient. The implant 402 also includes an implant indicator 518 (shown as "LXX-" on the implant 402) which can designate the type of implant. In other embodiments, the implant 402 can include more or fewer visual indicators.

Figure 6A:
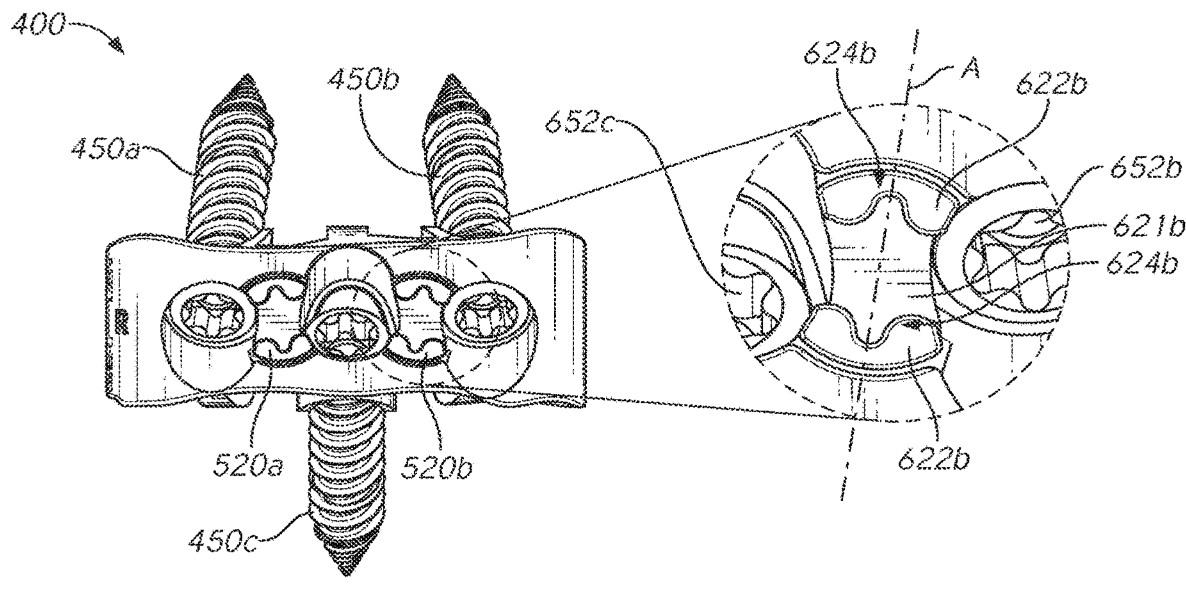
FIGS. 6A and 6B are front views of the spinal fusion device of FIG. 4 and illustrate the device in an unlocked configuration and a locked configuration, respectively.
Figure 6B:
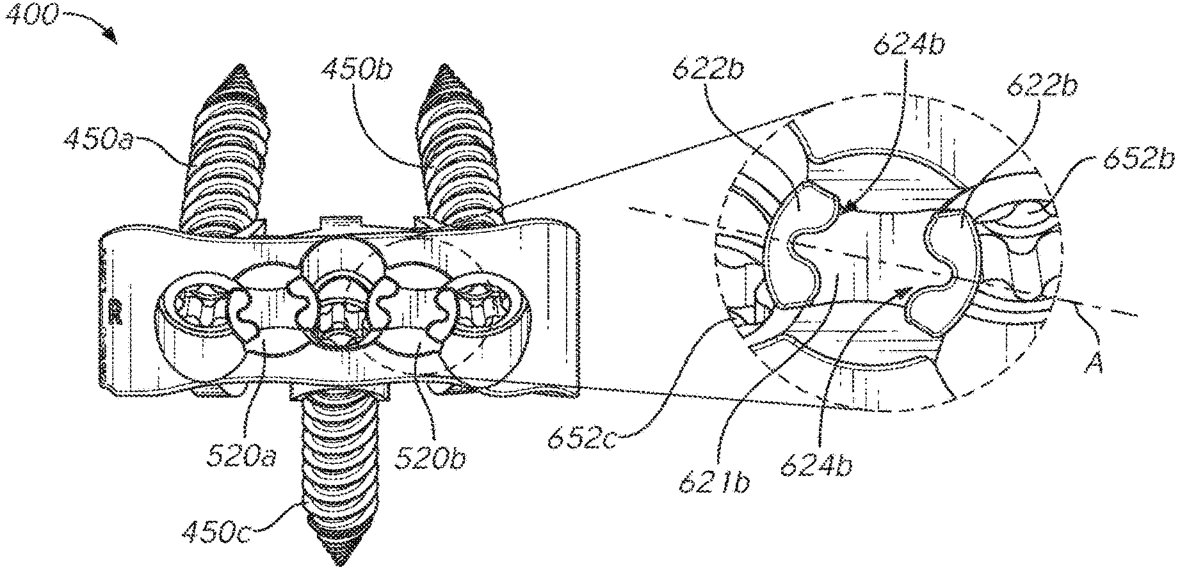

As set forth above, the device 400 can include one or more retention mechanisms 520 (e.g., cams) that can be transitioned between an unlocked configuration that permits a user to insert the fixation elements 450 into the corresponding lumens 510, and a locked configuration that holds the fixation elements 450 in the lumens 510. FIG. 6A is a front view of the device 400 in the unlocked configuration, and FIG. 6B is a front view of the device 400 in the locked configuration. Referring first to FIG. 6A, and specifically to the enlarged cut-away view of the portion of the implant 402 shown with dot-dash line, the second retention mechanism 620*b* can include a cam head 621*b* with one or more ridges or raised portions 622*b* forming a drive feature 624*b*. The cam head 621*b* has a longitudinal axis A extending through a center of the cam head 621*b* (e.g., through the drive features 624*b*). In the unlocked configuration, the longitudinal axis A has a first orientation, which in the illustrated embodiment is within about 50 degrees of vertical. Of note, the cam head 621 *b* does not block the entry apertures to the lumens 510 when in the unlocked configuration. As a result, the cam head 621 does not cover a head 652*b* of the second fixation element 650*b* or a head 652*c* of the third fixation element 650*c* in the unlocked configuration. This enables a user to insert the fixation elements 450 into the lumens 510.

Referring next to FIG. 6B, the cam head 621*b* has been rotated to the locked configuration. More specifically, the cam head 621 *b* has been rotated about 90 degrees in a clockwise direction relative to the configuration shown in FIG. 6A such that the longitudinal axis A has a second orientation, which in the illustrated embodiment is within about 50 degrees of horizontal. Of note, in the locked configuration, the cam head 621*b* at least partially blocks/covers the entry apertures to the second lumen 510*b* and the third lumen 510*c*, and therefore at least partially overlaps with the head 652*b* of the second fixation element 650*b* and the head 652*c* of the third fixation element 650*c*. As a result, the cam head 621*b* holds the second fixation element 450*b* and the third fixation element 450*c* in the second lumen 510*b* and the third lumen 510*c*, respectively. The cam head 621*b* can be rotated by inserting a tool into the drive features 624*b* of the cam head 621*b* and rotating the tool in the desired direction.

The first retention mechanism 520*a* can operate in the same or generally similar fashion as described for the second retention mechanism 520*b*. In some embodiments, the direction of rotation for transitioning between the unlocked and locked configurations may be different for the first retention mechanism 520*a* and the second retention mechanism 520*b*. For example, the first retention mechanism 520*a* can be transitioned from the unlocked configuration to the locked configuration by rotating its cam head in a counterclockwise direction, while the second retention mechanism 520*b* can be transitioned from the unlocked configuration to the locked configuration by rotating the cam head 621*b* in a clockwise direction. As a result, the first retention mechanism 520*a* can be transitioned from the locked configuration to the unlocked configuration by rotating its cam head in a clockwise direction, while the second retention mechanism 520*b* can be transitioned from the locked configuration to the unlocked configuration by rotating the cam head 621*b* in a counterclockwise direction. In such embodiments, rotating either retention mechanism 520 away from a center of the anterior surface 504 locks the retention mechanism 520, while rotating the retention mechanism 520 toward a center of the anterior surface 504 unlocks the retention mechanism 520. In other embodiments, the retention mechanisms 520 can be configured such that the direction of rotation is the same for moving between the locked and unlocked configurations.

The retention mechanisms 520 can also include one or more features for biasing the retention mechanism 520 toward retaining the configuration it is in at any given time. That is, the retention mechanism 520 can resist rotational movement unless a substantial rotational force is applied (e.g., by engaging the drive features 624*b*). This is expected to retain the retention mechanism 520 in its desired configuration and prevent accidental rotation of the retention mechanism 520. Examples of features for restricting rotational movement of retention mechanisms similar are described below with reference to FIGS. 10A-10C.

FIGS. 7A-10C illustrate features of an interbody implant 702 ("the implant 702") configured in accordance with select embodiments of the present technology. As one skilled in art will appreciate from the following description, the implant 702 can include certain features generally similar to the implant 402 described with reference to FIGS. 4-6B. For example, the implant 702 can include one or more retention mechanisms that can be generally similar to or the same as the retention mechanisms 520 of the implant 402 (FIGS. 4-6B). Accordingly, the following description of the implant 702 applies equally to the implant 402, and vice versa.

Figures 7A, 7B:
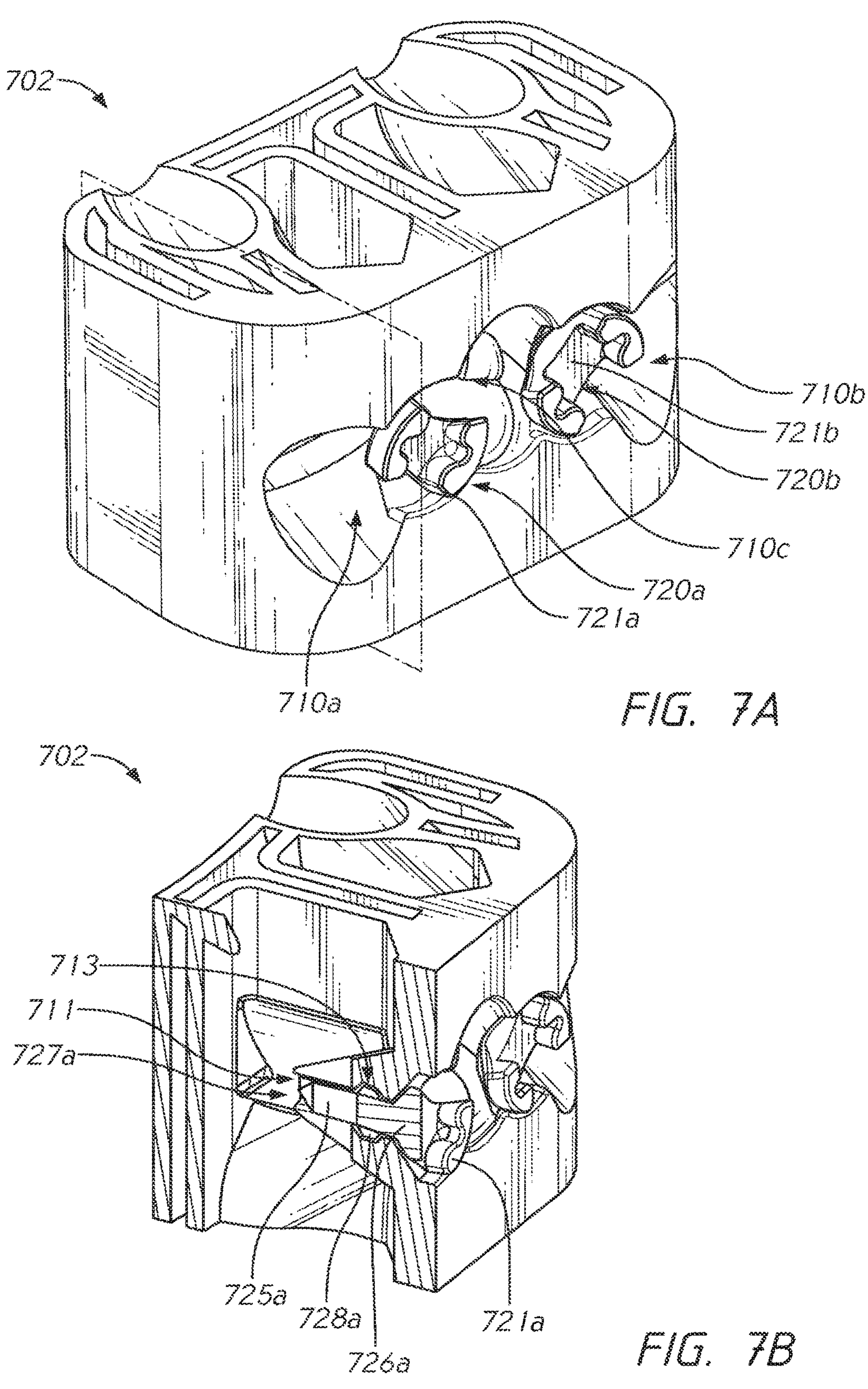
FIG. 7A is a perspective of another patient-specific interbody implant configured in accordance with select embodiments of the present technology.
FIGS. 7B and 7C are perspective and side cross-sectional views, respectively, of the interbody implant taken along the plane indicated in FIG. 7A.

FIG. 7A is a perspective view of the implant 702. As shown, the implant 702 is generally similar to the implant 402 described with respect to FIGS. 4-6B. For example, the implant 700 is configured for placement within an interbody space of a patient's spine to promote spinal fusion. The implant 702 can include a first lumen 710*a*, a second lumen 710*b*, and a third lumen 710*c* (collectively referred to as "the lumens 710"). The lumens 710 can be bores or screw holes that are configured to receive fixation elements (not shown) for anchoring the implant 702 to patient anatomy. The implant 702 can further include a first retention mechanism 720*a* and a second retention mechanism 720*b*. In operation, the first retention mechanism 720*a* can assist in holding fixation elements positioned within the first lumen 710*a* and the third lumen 710*c* in place. Similarly, the second retention mechanism 720*b* can assist in holding fixation elements positioned within the second lumen 710*b* and the third lumen 710*c* in place. Similar to the retention mechanisms 520 described with reference to FIGS. 5A-6B, the retention mechanisms 720 can include corresponding cam heads 721*a*, 721*b* that enable a user to selectively rotate the retention mechanisms 720 between unlocked and locked configurations.

Figures 7C, 8A:
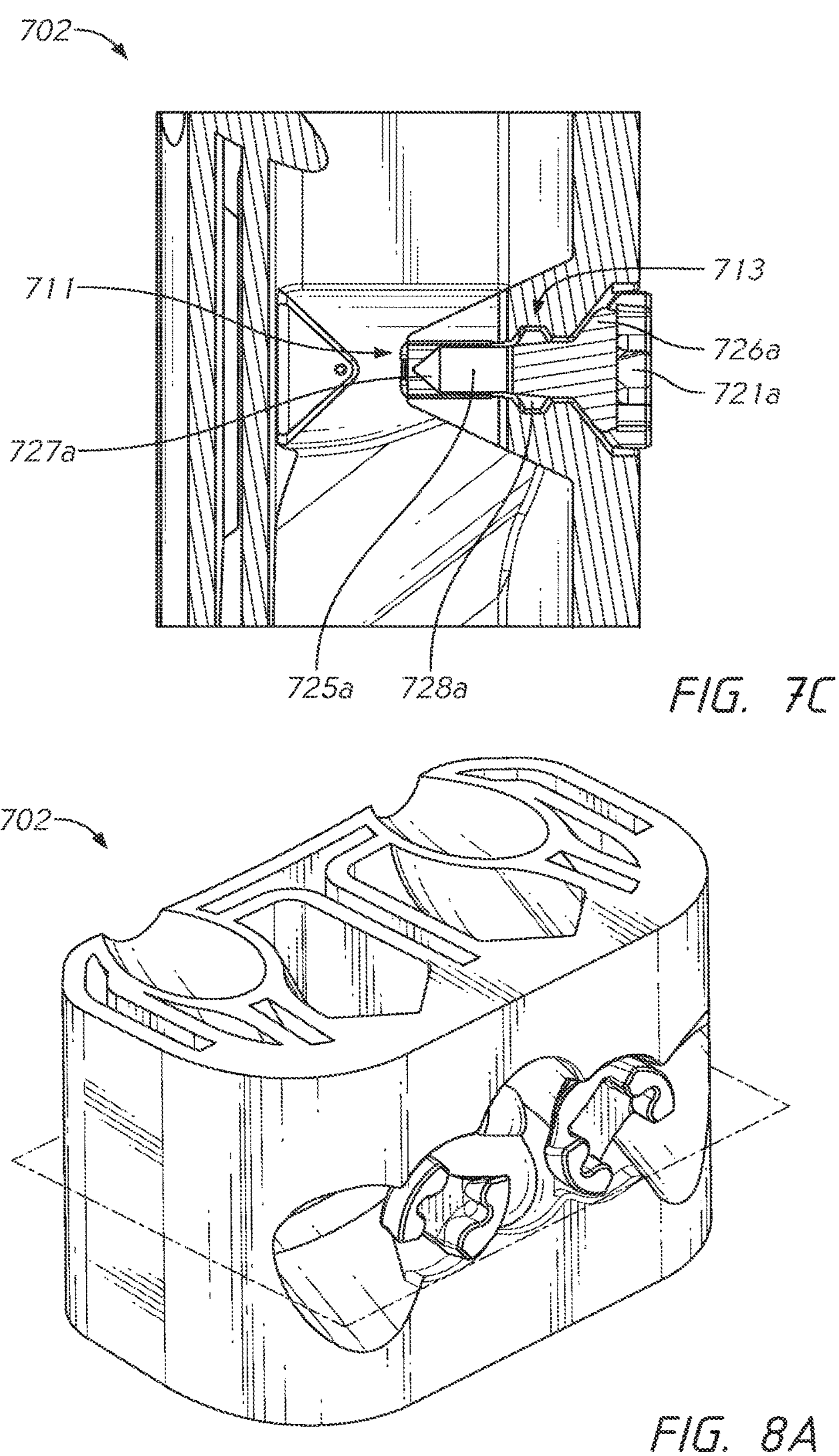
FIG. 8A is a perspective of the patient-specific interbody implant of FIG. 7A.

FIG. 7B is a perspective cross-sectional view of the implant 702 taken along the plane indicated in FIG. 7A, and FIG. 7C is a side cross-sectional view of the implant 702 taken along the same plane. Referring collectively to FIGS. 7B and 7C, the first retention mechanism 720*a* includes a shaft 725*a* extending distally from the cam head 721*a*. The shaft 725*a* extends between a tapered shank region 726*a* proximal the cam head 721*a* and a distal end region 727*a* defining a tip. The shaft 725*a* further includes a raised lip or ridge 728*a*. As described in detail below with respect to FIGS. 9A-9C, the ridge 728*a* extends partially, but not fully, around a circumference of the shaft 725*a* and helps define the range of rotational motion of the retention mechanism 720*a*.

The implant 702 further includes a retention mechanism lumen 711 for receiving the shaft 725*a* of the retention mechanism. The retention mechanism lumen 711 can also include a corresponding channel 713 for receiving the ridge 728*a* on the shaft 725*a*. Similar to the ridge 728*a*, and as described in detail below with respect to FIGS. 9A-9C, the channel 713 extends partially, but not fully, around a circumference of the retention mechanism lumen 711. In some embodiments, the shaft 725*a* and the retention mechanism lumen 711 are both smooth (e.g., non-threaded). In other embodiments, the shaft 725*a* and/or the retention mechanism lumen 711 can be threaded to assist with the connection between the retention mechanism 720*a* and the retention mechanism lumen 711.

Figure 8B:
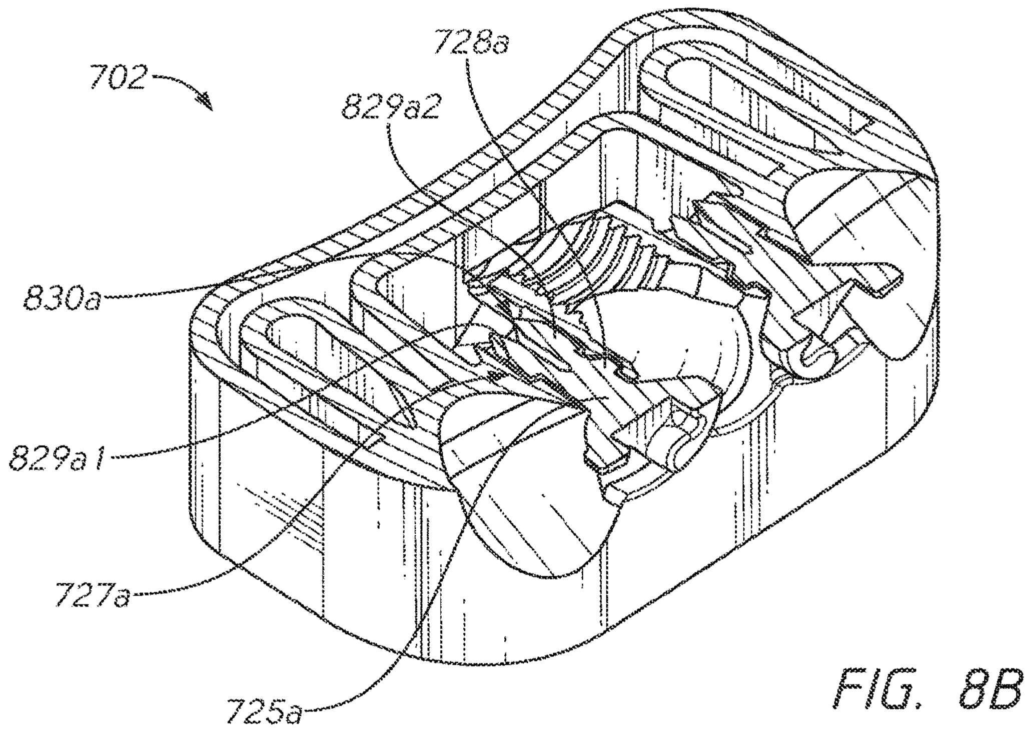
FIGS. 8B and 8C are perspective and top cross-sectional views, respectively, of the interbody implant taken along the plane indicated in FIG. 8A.
Figure 8C:
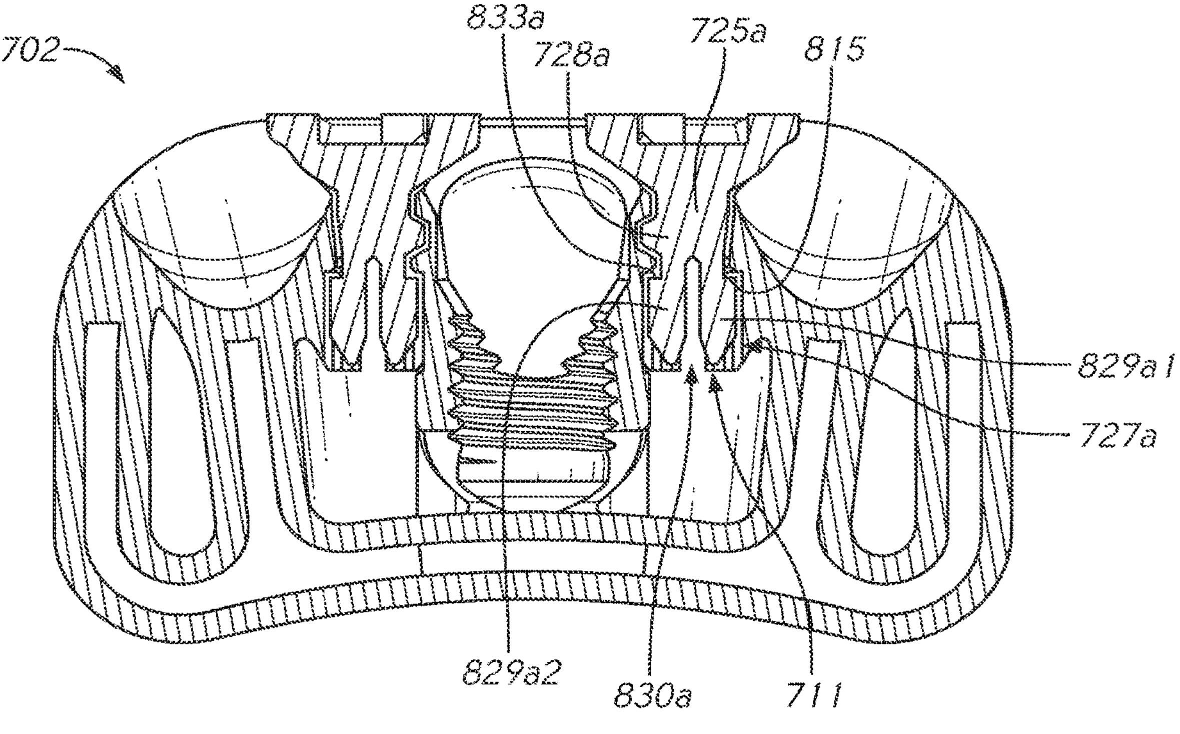

FIGS. 8A-8C illustrate additional features of the implant 702. More specifically, FIG. 8A is a perspective view of the implant 702, FIG. 8B is a perspective cross-sectional view of the implant 702 taken along the plane indicated in FIG. 8A, and FIG. 8C is a top view of the implant 702 taken along the same plane. Referring collectively to FIGS. 8B and 8C, the distal end region 727*a* of the shaft 725*a* includes a first prong 829$a_1$ and a second prong 829$a_2$ (collectively referred to as the "prongs 829*a*") extending distally into the tip portion of the shaft 725*a*. The prongs 829*a* are separated by a gap 830*a*. As described in detail below with reference to FIGS. 10A-10C, the prongs 829*a* can include features that prevent or at least reduce inadvertent rotation of the retention mechanism 720*a*. In some embodiments, the prongs 829*a* can also assist with preventing the retention mechanism 720*a* from backing out of the retention mechanism lumen 711. For example, as the shaft 725*a* is inserted into the retention mechanism lumen 711, the prongs 829*a* can be at least partially elastically deformed (e.g., squeezed together to close or at least partially close the gap 830*a*). As the prongs 829*a* pass a step 815 (FIG. 8C) of the retention mechanism lumen 711, the prongs 829*a* can elastically snap back to and/or toward their undeformed shape that includes the gap 830*a*. A back surface 833*a* (FIG. 8C) of the prongs 829*a* can then abut the step 815 and prevent expulsion of the retention mechanism 720*a* from the retention mechanism lumen 711. In some embodiments, such as described below with reference to FIGS. 14-16, the retention mechanism 720*a* can be manufactured (e.g., printed) in the retention mechanism lumen 711. In such embodiments, the prongs 829*a* are not elastically deformed as the shaft 725*a* is inserted into the retention mechanism lumen 725 (because the shaft 725*a* is printed in its intended position). However, in such embodiments the back surface 833*a* can still engage the step 815 to help hold the retention mechanism 720*a* in the retention mechanism lumen 711.

Figures 9A, 9B:
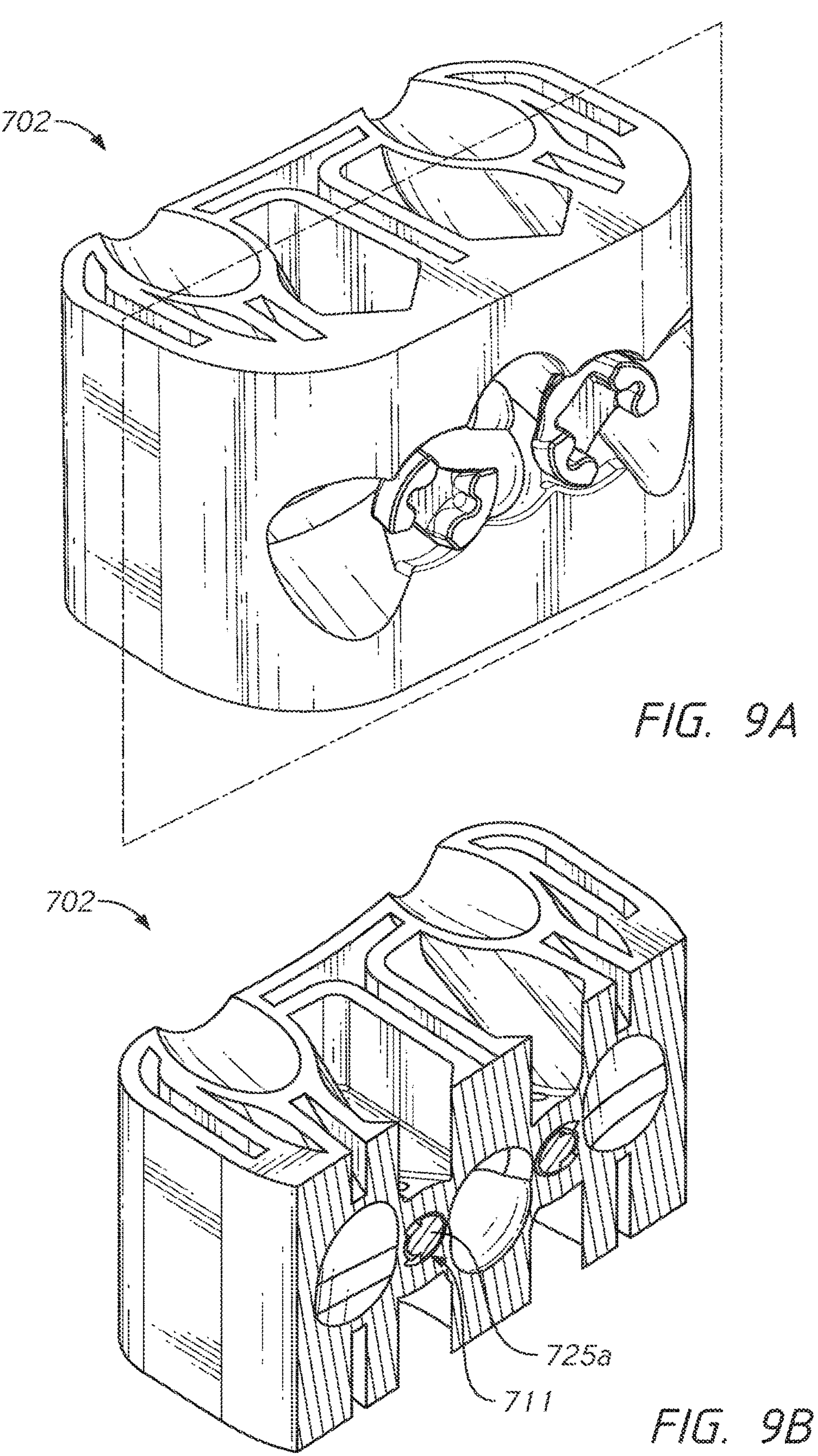
FIG. 9A is a perspective of the patient-specific interbody implant of FIG. 7A.
FIGS. 9B and 9C are perspective and front cross-sectional views, respectively, of the interbody implant taken along the plane indicated in FIG. 9A.
Figure 9C:
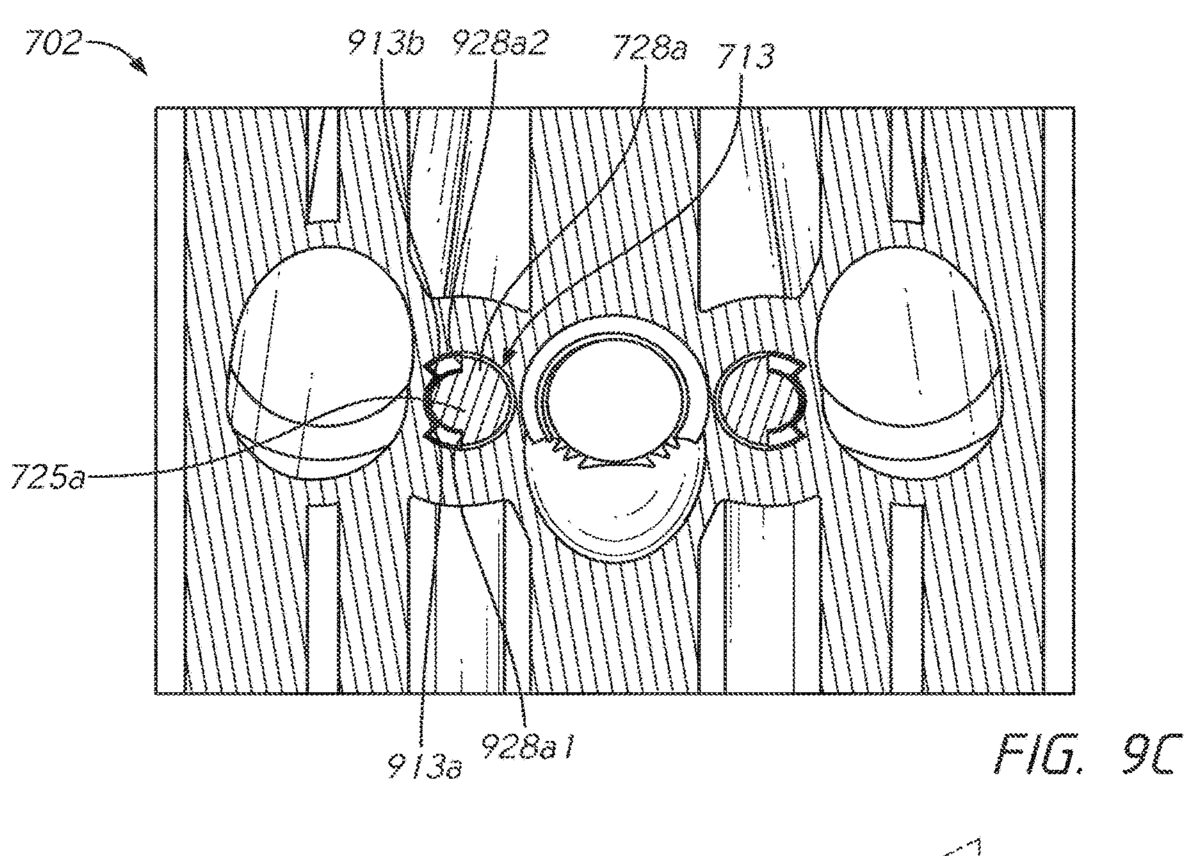

FIGS. 9A-9C illustrate additional features of the implant 702. More specifically, FIG. 9A is a perspective view of the implant 702, FIG. 9B is a perspective cross-sectional view of the implant 702 taken along the plane indicated in FIG. 9A, and FIG. 9C is a front view of the implant 702 taken along the same plane. As shown in FIG. 9B, the cross-section illustrates a portion of the shaft 725*a* in the retention mechanism lumen 711. More specifically, and as best shown in FIG. 9C, the cross-section illustrates the portion of the shaft 725*a* including the ridge 728*a*. As shown, the ridge 728*a* extends around about 180 degrees of a circumference of the shaft 725 *a*, between a first surface $928a_1$ and a second surface $928a_2$ (the degree to which the ridge 728*a* extends around the shaft 725*a* can be referred to herein as a circumferential length of the ridge 728*a*). In some embodiments, the ridge 728*a* can extend around more or less of the shaft 725*a*, such as between about 90 degrees and about 270 degrees, or between about 135 degrees and about 225 degrees, or between about 160 degrees and about 200 degrees, or between about 170 degrees and about 190 degrees. The ridge 728*a* can have a height that is between about 10% and 100% of the diameter of the shaft 725*a*. For example, the ridge can have a height that is between about 20% and about 80% of the diameter of the shaft 725*a*, or between about 20% and about 50% of the diameter of the shaft 725*a*, or between about 20% and about 30% of the diameter of the shaft 725*a*. Although described separately, the ridge 725*a* can be contiguous with the shaft 725*a*.

As set forth above, the retention mechanism lumen 711 includes a channel 713 for receiving the ridge 728*a*. As shown, the channel 713 extends around about 270 degrees of a circumference of the retention mechanism lumen 711, between a first channel wall 913*a* and a second channel wall 913*b* (the degree to which the channel 713 extends around the retention mechanism lumen 711 can be referred to herein as a circumferential length of the channel 713). In some embodiments, the channel 713 can extend around more or less of the retention mechanism lumen 711, such as between about 325 degrees and about 180 degrees, or between about 325 degrees and about 225 degrees, or between about 300 degrees and about 240 degrees. Of note, the channel 713 extends further than the ridge 728*a*, such that the ridge 728*a* can rotate within the channel 713 as described in greater detail below. That is, the ridge 728*a* can have a first circumferential length that is less than a second circumferential length of the channel 713. The channel 713 can have a height that corresponds to (e.g., is equal to or slightly greater than) the height of the ridge 728*a*.

In operation, the shaft 725*a* can rotate within the retention mechanism lumen 711 as the retention mechanism 720*a* is transitioned between the unlocked configuration and the locked configuration. The ridge 728*a* and the channel 713 define the degree to which the retention mechanism 720*a* can rotate. For example, when the retention mechanism 720*a* is in an unlocked configuration, the first surface $928a_1$ of the ridge 728*a* is positioned proximate (e.g., in contact with) the first channel wall 913*a*. Thus, when the retention mechanism 720*a* is in the unlocked configuration, the engagement between the first surface $928a_1$ and the first channel wall 913*a* prevents clockwise rotation of the retention mechanism 720*a*. From the unlocked configuration, the retention mechanism 720*a* can be rotated counterclockwise about 90 degrees until the second surface $928a_2$ of the ridge 728*a* contacts the second channel wall 913*b*, which corresponds to the locked configuration. Thus, when the retention mechanism 720*a* is in the locked configuration, the engagement between the second surface $928a_2$ and the second channel wall 713*b* prevents counterclockwise rotation of the retention mechanism 720*a* (FIG. 9C illustrates the retention mechanism 720*a* in an intermediate configuration between the unlocked configuration and the locked configuration). Thus, the ridge 728*a* and the channel 713 restricts rotation of the retention mechanism 720*a* to a predefined path and degree.

The distance (e.g., degrees of rotation) that the retention mechanism 720*a* can be rotated through is set based on a difference between the circumferential length of the ridge 728*a* and the circumferential length of the channel 713. In the illustrated embodiment, for example, the ridge 728*a* extends about 180 degrees and the channel 713 extends about 270 degrees. Thus, the retention mechanism 720 *a* can be rotated about 90 degrees (the difference between 270 degrees and 180 degrees). Accordingly, the dimensions of the ridge 728*a* and the channel 713 can be selected based on the desired amount of rotation for the retention mechanism 720*a*.

Figure 10A:
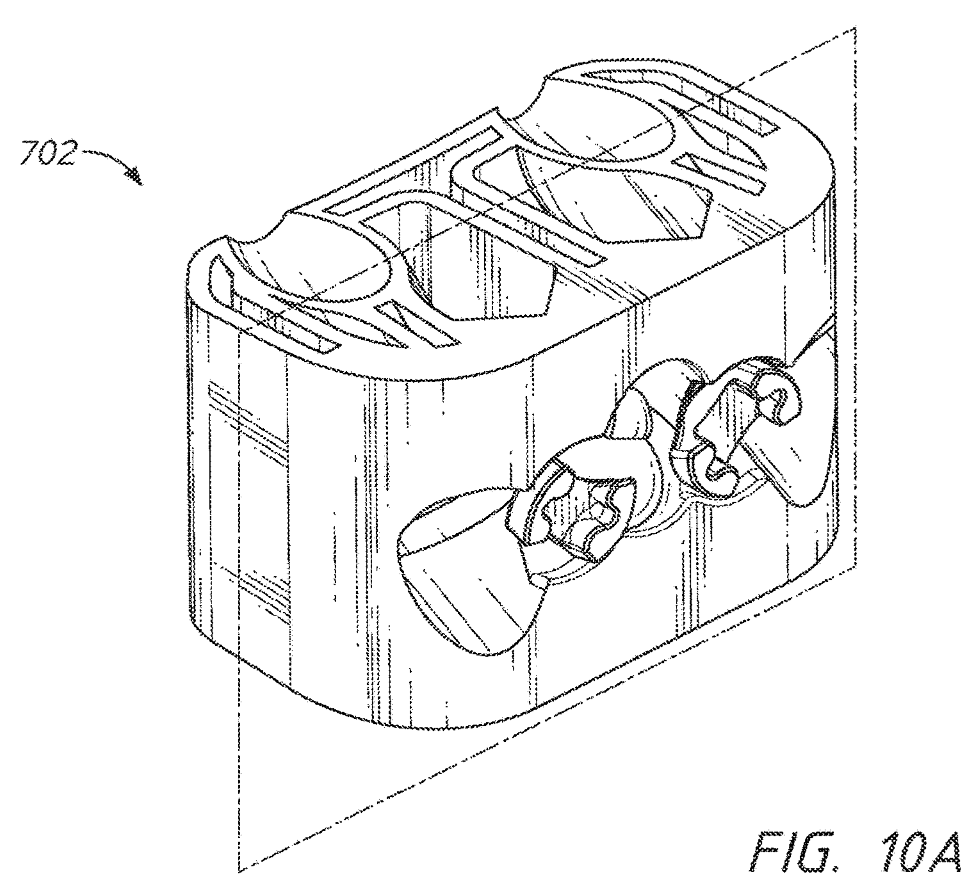
FIG. 10A is a perspective of the patient-specific interbody implant of FIG. 7A.
Figure 10B:
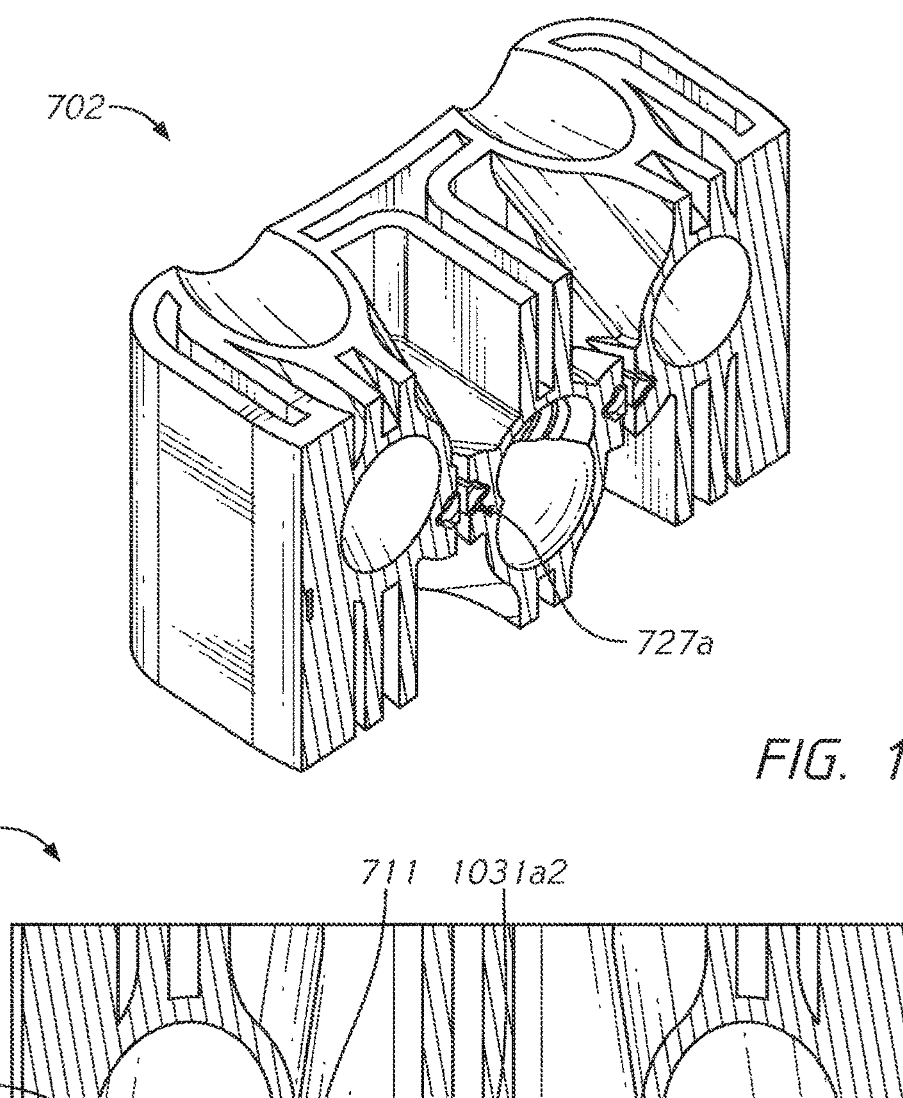
FIGS. 10B and 10C are perspective and front cross-sectional views, respectively, of the interbody implant taken along the plane indicated in FIG. 10A.
Figure 10C:
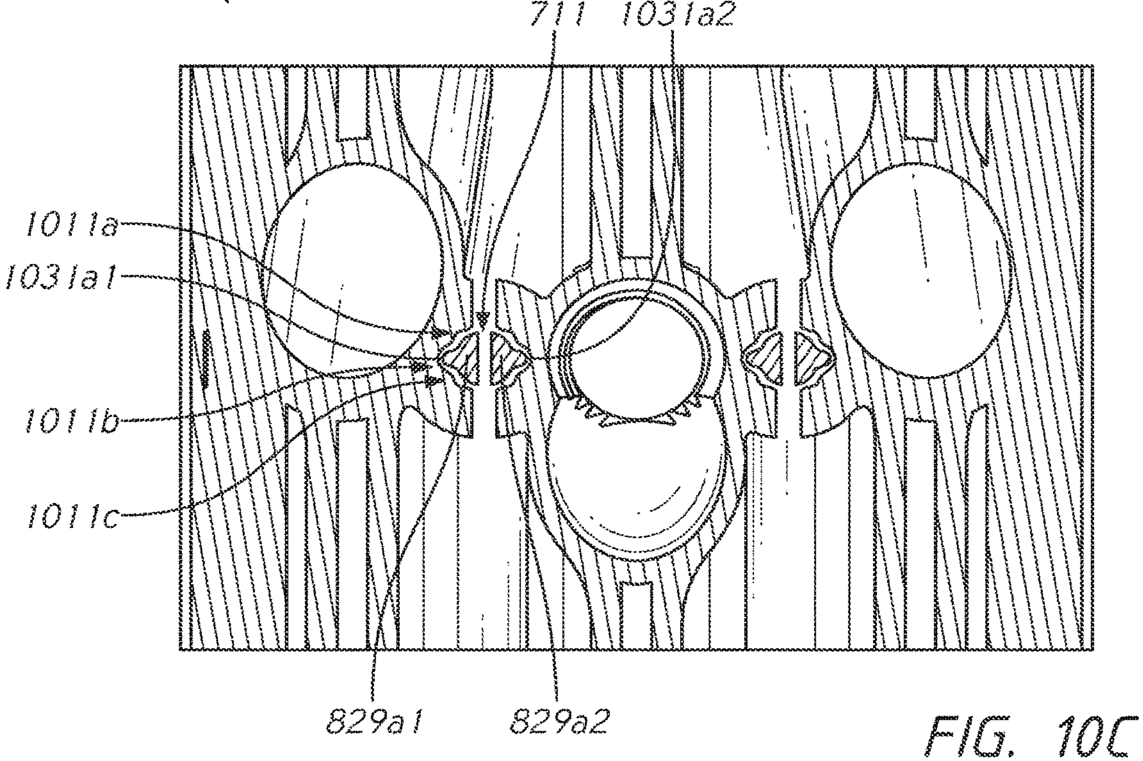

FIGS. 10A-10C illustrate additional features of the implant 702. More specifically, FIG. 10A is a perspective view of the implant 702, FIG. 10B is a perspective cross-sectional view of the implant 702 taken along the plane indicated in FIG. 10A, and FIG. 10C is a front view of the implant 702 taken along the same plane. As shown in FIG. 10B, the cross-section illustrates a portion of the distal end region 727*a* of the shaft 725*a*. More specifically, and as best shown in FIG. 10C, the cross-section illustrates a cross-sectional profile of the prongs 829*a*. As shown, the first prong $829a_1$ includes a first projection $1031a_1$ (e.g., a first nipple, nub, bump, etc.) and the second prong $829a_2$ includes a second projection $1031a_2$ (e.g., a second nipple, nub, bump, etc.). The projections 1031*a* can extend transverse or at least generally transverse to a longitudinal axis of the shaft 725*a*.

The portion of the retention mechanism lumen 711 that receives the prongs 829*a* can include a first groove or notch 1011*a*, a second groove or notch 1011*b*, and a third groove or notch 1011*c*. The retention mechanism lumen 711 can include similar grooves or notches corresponding to the second projection $1031a_2$. As a result, the portion of the retention mechanism lumen 711 that receives the prongs 829*a* has an at least partially irregular-shaped cross-section (e.g., a flower-shaped cross-sectional area). In some embodiments, the retention mechanism lumen 711 can include more or fewer grooves, such as two, four, five, six, seven, or eight grooves.

In operation, the prongs 829*a* rotate within the retention mechanism lumen 711 as the retention mechanism 720*a* is rotated between the unlocked configuration and the locked configuration. When the retention mechanism 720*a* is in the unlocked configuration, the projection 1031$a_1$ is positioned within the first groove 1011*a*. When the retention mechanism 720*a* is in the locked configuration, the projection 1031$a_1$ is positioned within the third groove 1011*c*. When the retention mechanism 720*a* is positioned in an intermediate configuration between the unlocked configuration and the locked configuration, the projection 1031$a_1$ can be positioned within the second groove 1011*b*. In embodiments with more grooves 1011, each groove can correspond to another intermediate configuration. In embodiments with only two grooves 1011 (e.g., only the first groove 1011*a* and the second groove 1011*b*), the grooves can correspond to the unlocked configuration and the locked configuration.

Together, the first projection 1031$a_1$ and the grooves 1011 define incremental, predefined positions for the retention mechanism 720*a*. For example, in the illustrated embodiment there are three predefined positions: the unlocked configuration, the intermediate configuration, and the locked configuration. Each of these configurations represents a relatively "low energy" state of the retention mechanism 720*a*, whereas other configurations in which the projection 1031$a_1$ is not in a groove 1011 represent relatively higher energy states of the retention mechanism 720*a*. Thus, the retention mechanism 720*a* can be biased toward occupying the three predefined positions. To move between the incremental, predefined positions, a rotational force must be applied to the retention mechanism 720*a* that is sufficient to cause the projection 1031*a* to jump over a bump between two grooves 1011 (e.g., sufficient to pass the retention mechanism 720*a* through the relatively higher energy state). Without intending to be bound by theory, the projections 1031*a* and the grooves 1011 are therefore expected to reduce unintentional rotation of the retention mechanism 1020*a*. Thus, the projections 1031*a* and the grooves 1011 help retain the retention mechanism 1020*a* in whichever configuration a user sets them to (e.g., the locked configuration).

Figure 11A:
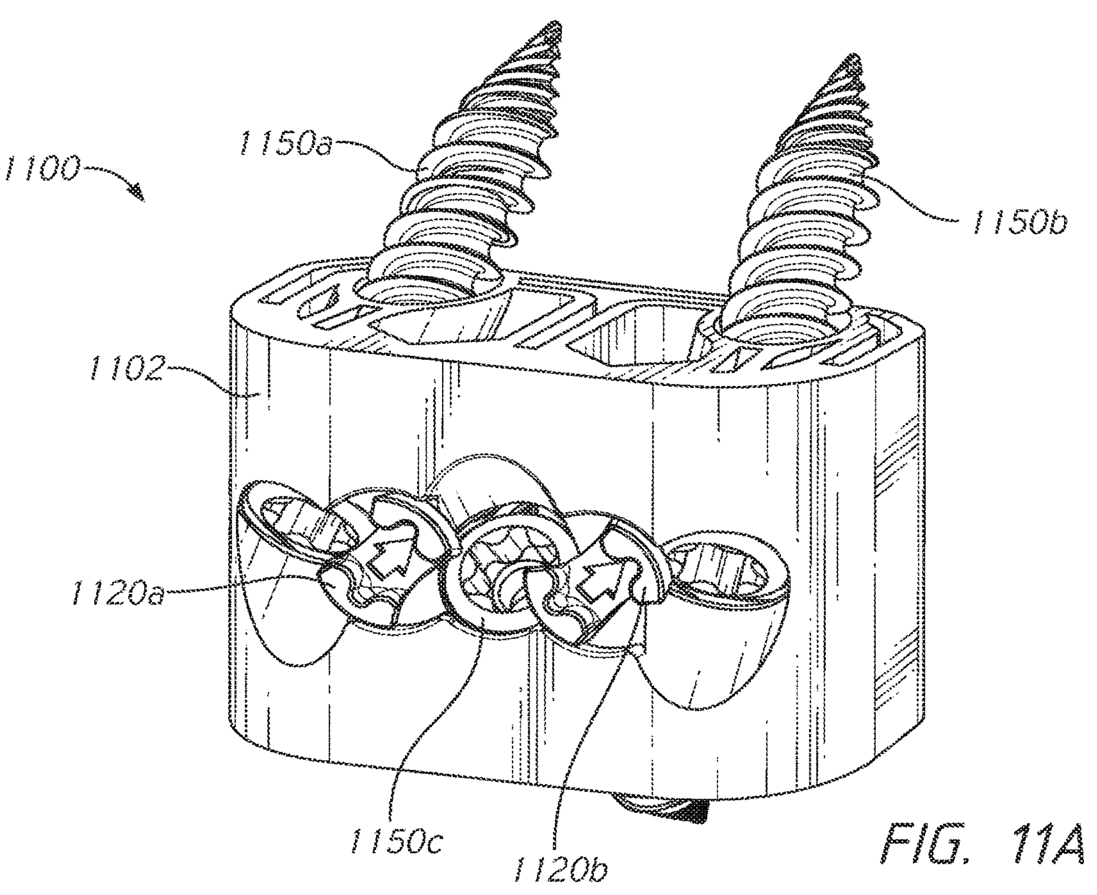
FIGS. 11A-11C illustrate another patient-specific interbody implant configured in accordance with select embodiments of the present technology.
Figure 11B:
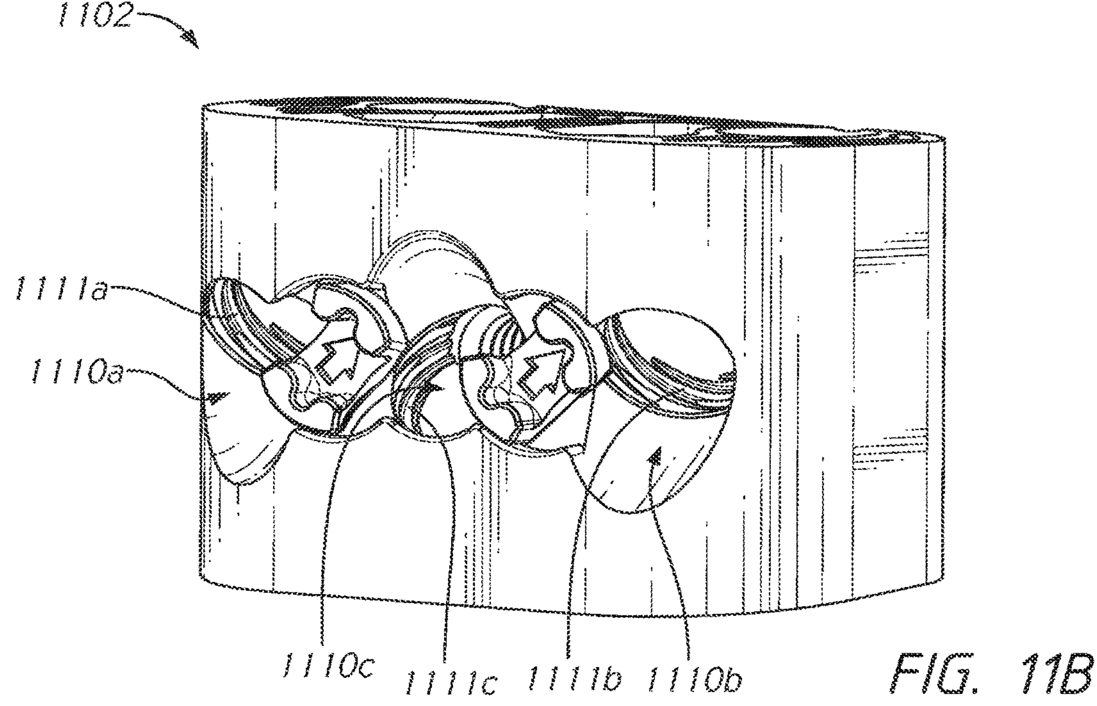
Figure 11C:
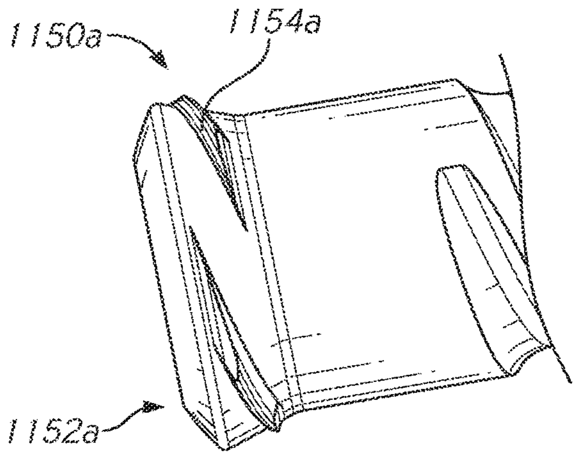

FIGS. 11A-11C illustrate another patient-specific spinal fusion device 1100 ("the device 1100") configured in accordance with select embodiments of the present technology. The device 1100 can include certain features generally similar to the device 400 described with reference to FIGS. 4-6B and the implant 702 described with reference to FIGS. 7A-10C. Accordingly, the following description of the device 1100 can apply to the device 400 and the implant 702, and vice versa.

FIG. 11A is a perspective view of the device 1100. Similar to the device 400 of FIG. 4, the device 1100 includes a patient-specific interbody implant 1102 and a plurality of fixation elements or screws 1150*a-c*. The device further includes a first retention mechanism 1120*a* and a second retention mechanism 1120*b* ("the retention mechanisms 1120") that can operate similar to or the same as the retention mechanisms 520 described with reference to FIGS. 5A-6B. For example, the retention mechanisms 1120 can be selectively and independently rotated between an unlocked configuration and a locked configuration.

FIG. 11B is a perspective view of the implant 1102 with the fixation elements 1150*a-c* removed to more clearly illustrate certain features of the implant 1102. As shown, the implant 1102 includes a first lumen 1110*a* for receiving the first fixation element 1150*a*, a second lumen 1110*b* for receiving the second fixation element 1150*b*, and a third lumen 1110*c* for receiving the third fixation element 1150*c* (collectively referred to as "the lumens 1110"). Relative to the screw lumens described above with reference to FIGS. 4-6B, each of the lumens 1110 includes a threaded portion proximate its entrance (e.g., at and/or extending from the entry aperture). In particular, the first lumen 1110*a* includes a first threaded portion 1111*a*, the second lumen 1110*b* includes a second threaded portion 1111*b*, and the third lumen 1110*c* includes a third threaded portion 1111*c* (collectively referred to as "the threaded portions 1111"). In some embodiments, the threaded portions 1111 extend only partially along a length of the lumens 1110. For example, each threaded portion 1111 may extend less than about 25%, less than about 20%, less than about 15%, less than about 10%, or less than about 5% along the length of the corresponding lumen 1110. In other embodiments, the threaded portion 1111 can extend along substantially the entire length of the corresponding lumen 1110 (e.g., at least about 80%, or at least about 90%, or at least about 95% of the entire length of the lumen 1110).

The threaded portions 1111 can threadably mate with threads on the fixation elements 1150, e.g., to improve the connection between the fixation elements 1150 and the implant 1102. For example, FIG. 11C is an enlarged view of a proximal head portion 1152*a* of the first fixation element 1150*a*. As shown, the proximal head portion 1152*a* can include a first thread 1154*a*. The first thread can be sized and shape to threadably mate with the first threaded portion 1111*a* of the first lumen 1110*a* (FIG. 11B). Without intending to be bound by theory, providing a threaded connection between the fixation elements 1150 and the implant 1102 may further improve the stability of the connection therebetween, which in turn may further improve the stability of the device 1100 when implanted in the patient.

Figure 12A:
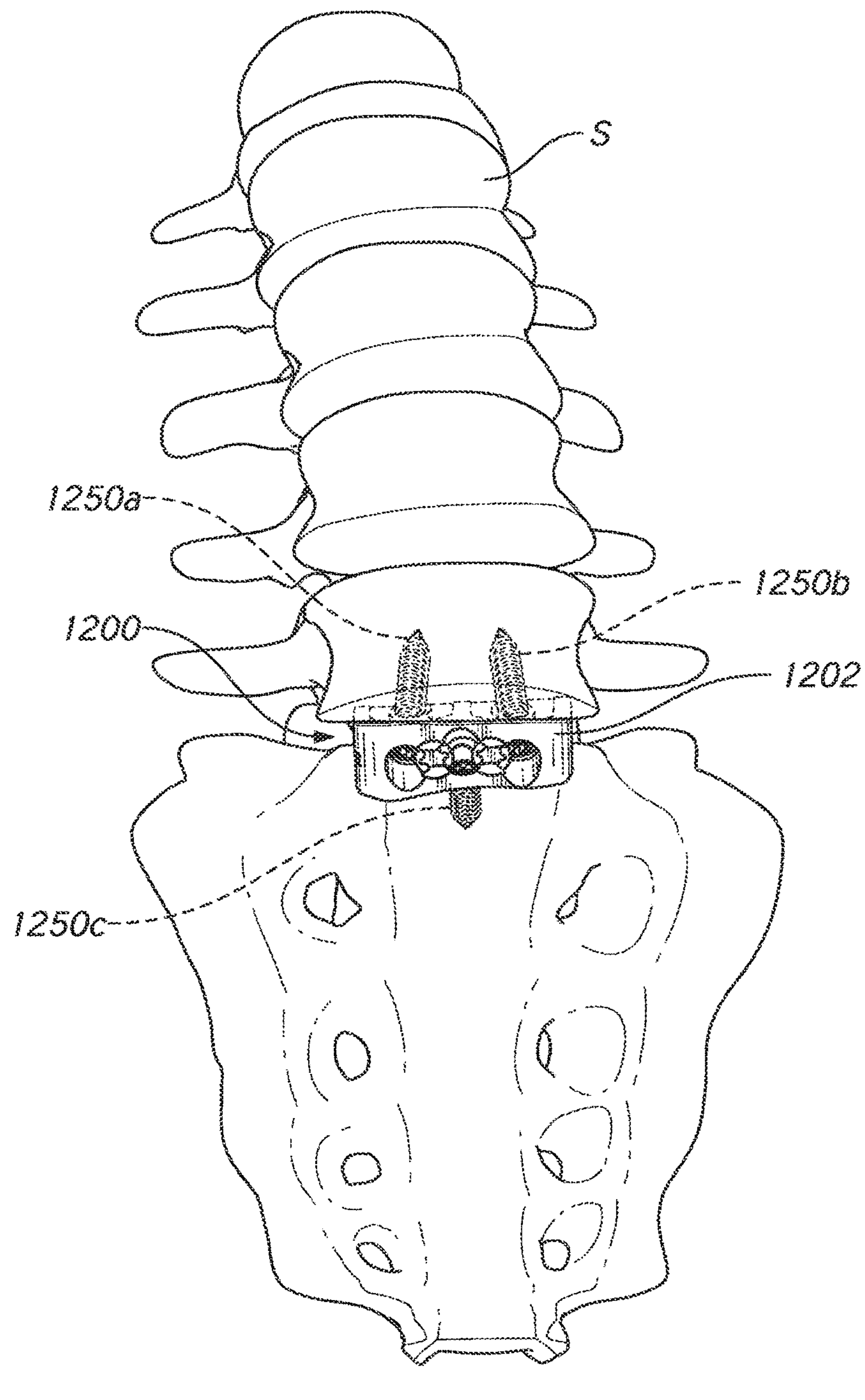
FIGS. 12A-12D are front, side, top, and bottom views, respectively, of another patient-specific spinal fusion device configured in accordance with select embodiments of the present technology and implanted in a patient's spine.
Figure 12B:
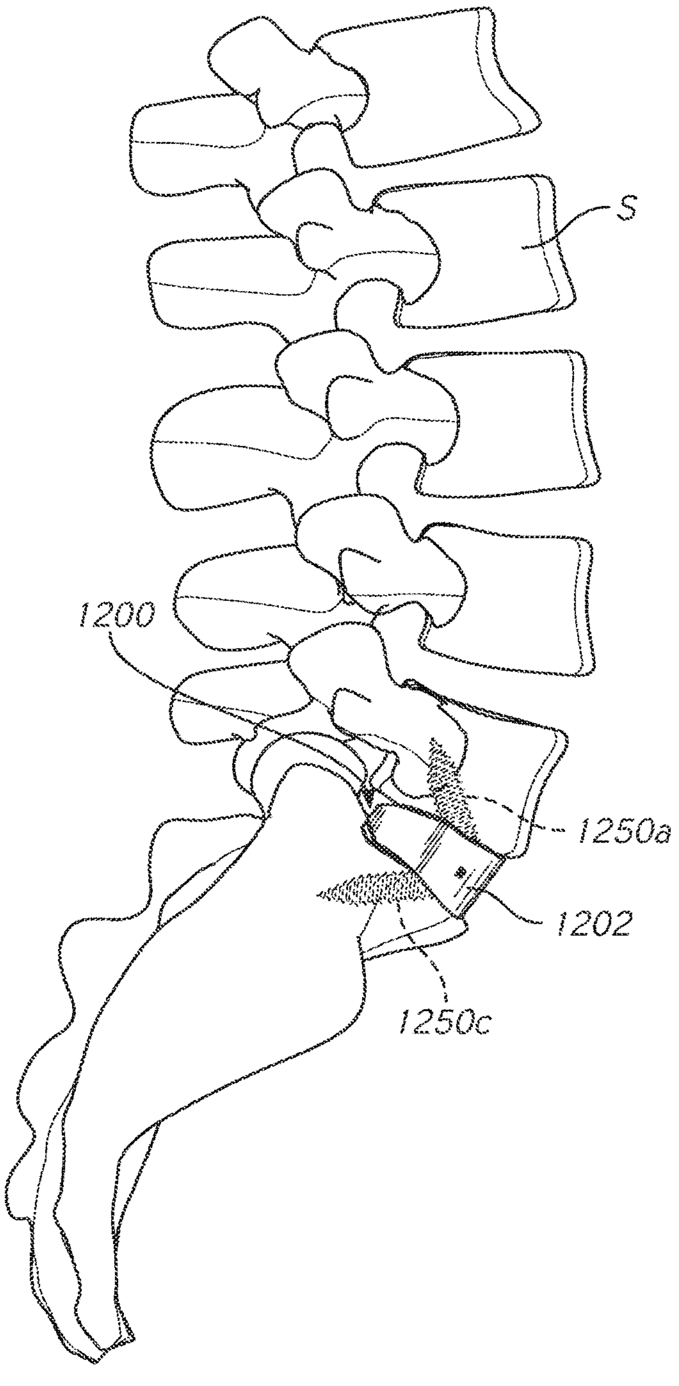
Figure 12C:
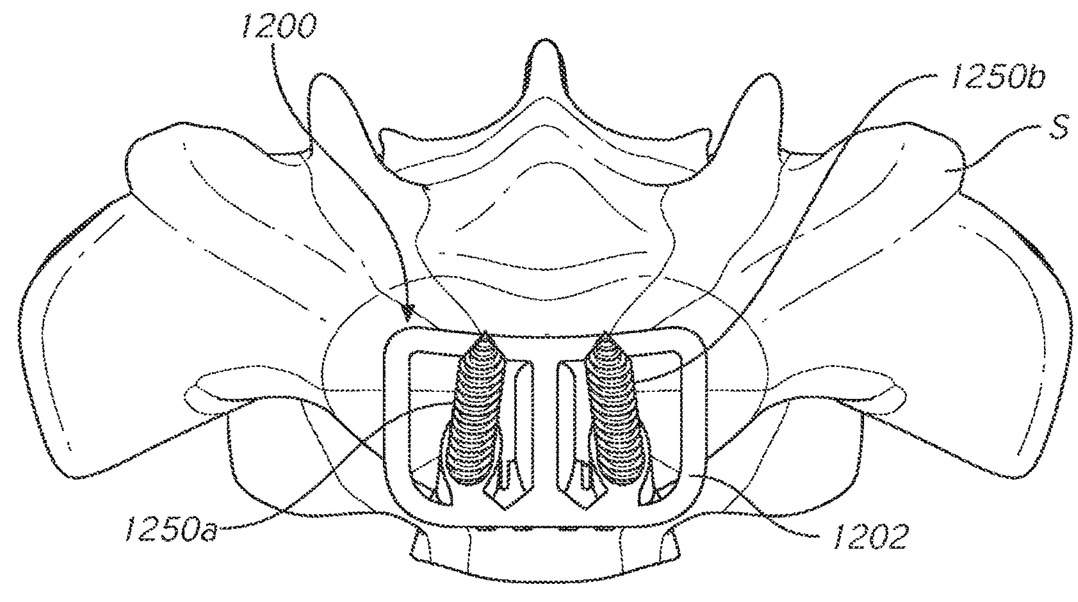
Figure 12D:
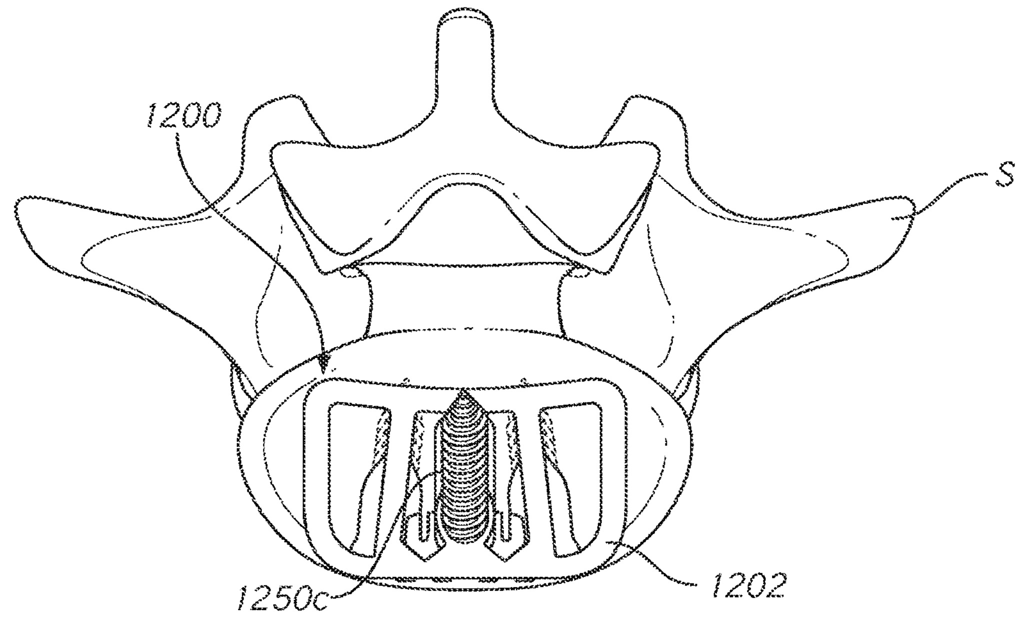

FIGS. 12A-12D illustrate a patient specific spinal fusion device 1200 ("the device 1200") implanted in a patient's spine S and configured in accordance with select embodiments of the present technology. More specifically, FIG. 12A is a front (e.g., anterior) view of the device 1200 implanted in the patient's spine S, FIG. 12B is a side (e.g., lateral) view of the device 1200 implanted in the patient's spine S, FIG. 12C is a top view of the device 1200 implanted in the patient's spine S, and FIG. 12D is a bottom view of the device 1200 implanted in the patient's spine S. Referring collectively to FIGS. 12A-12D, the device 1200 can include an interbody implant 1202 positioned within an intervertebral disc space of the spine S. The implant 1202 can be generally similar to or the same as the implant 402 described with respect to FIGS. 4-6B, the implant 702 described with reference to FIGS. 7A-10C, and/or the implant 1102 described with reference to FIGS. 11A-11C. The device 1200 can also include a first fixation element 1250*a*, a second fixation element 1250*b*, and a third fixation element 1250*c* (collectively referred to as "the fixation elements 1250"). The fixation elements 1250 can anchor the implant 1202 to the patient's spine S, as described throughout this Detailed Description.

Figure 13A:
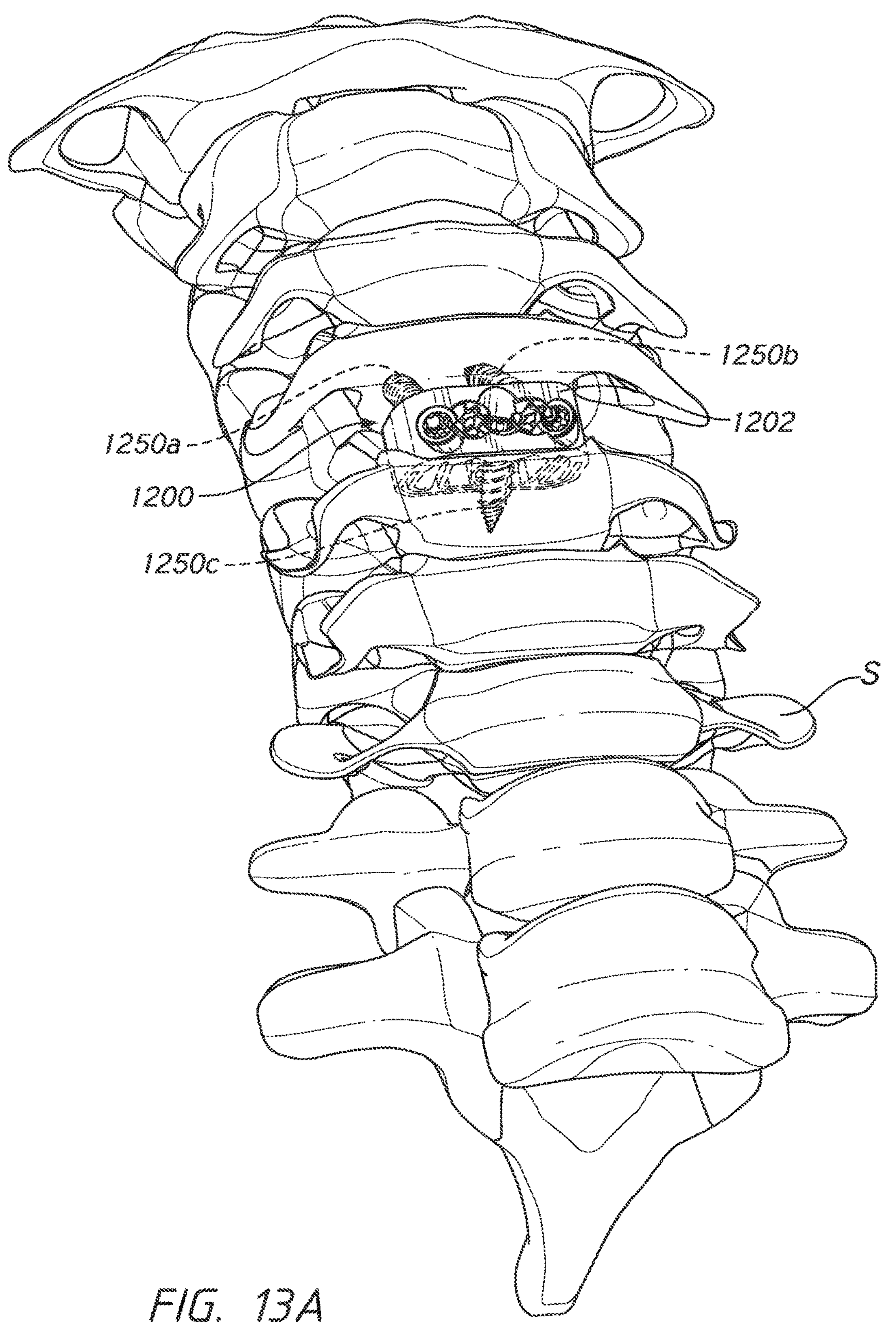
FIGS. 13A and 13B are front and side views, respectively, of another patient-specific spinal fusion device configured in accordance with select embodiments of the present technology and implanted in a cervical region of a patient's spine.
Figure 13B:
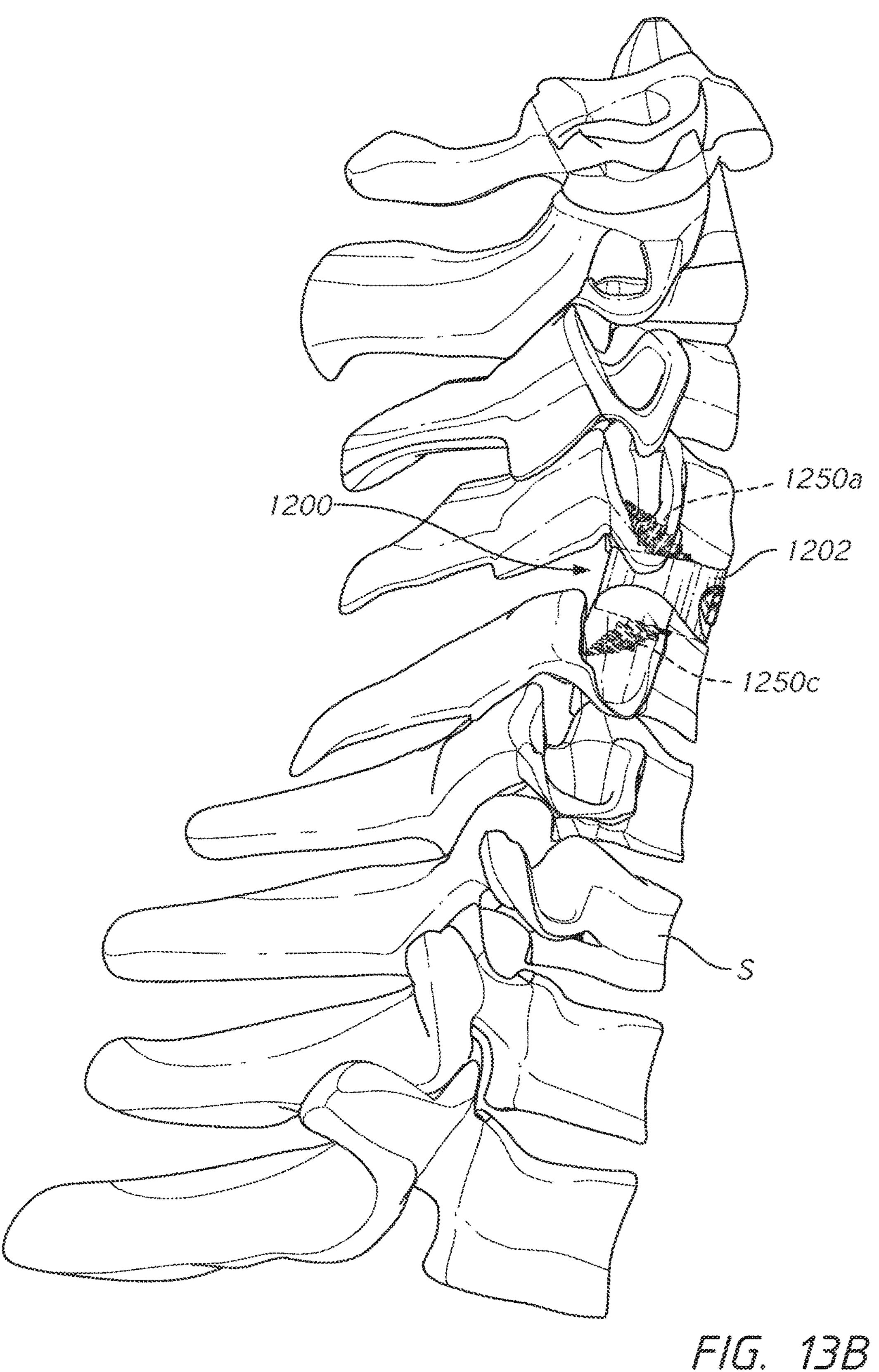

The device 1200 is shown as implanted in the sacral/lumbar region of the patient's spine S, e.g., between L5 and S1. In other embodiments, the device 1200 can be implanted at other vertebral levels, including other lumbar levels, thoracic levels, or cervical levels. For example, FIGS. 13A and 13B are front and side views of the device 1200 implanted between adjacent cervical vertebrae in the patient's spine S, e.g., to provide cervical fusion. As one skilled in the art will appreciate, FIGS. 12A-13B are provided as examples only—the devices described herein can be implanted at any vertebral level in the patient's spine S to promote intervertebral fusion.

As one skilled in the art will appreciate, the patient specific spinal fusion devices described with respect to FIGS. 4-13B are provided as representative embodiments. The present technology includes variations of these embodiments, including devices with combinations of features described with respect to FIGS. 4-13B and devices with only some of the features described with respect to FIGS. 4-13B.

D. SELECT METHODS OF MANUFACTURING PATIENT-SPECIFIC SPINAL FUSION DEVICES

Figure 14:
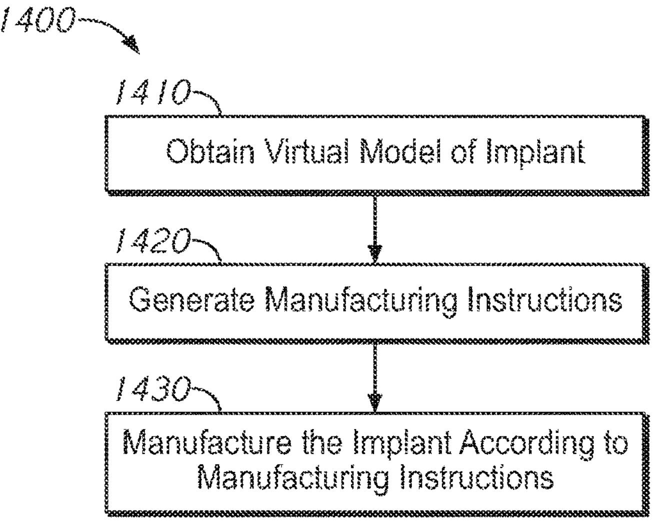
FIG. 14 is a flow diagram illustrating a method for manufacturing an implant in accordance with select embodiments of the present technology.

FIG. 14 is a flow diagram illustrating a method 1400 for manufacturing an implant in accordance with select embodiments of the present technology. The method 1400 can include obtaining a virtual model of an implant. Manufacturing instructions can be generated based on the virtual model. The manufacturing instructions can be designed for execution by a manufacturing system to form the implant in a single manufacturing process performed by a single manufacturing machine, multiple manufacturing processes performed by a single manufacturing machine, and/or multiple manufacturing processes performed by multiple manufacturing machines at the same site or different manufacturing sites (e.g., manufacturing sites remote from the healthcare provider). Details of the method 1400 are described in connection with FIGS. 12-14.

At block 1410 (FIG. 14), a virtual model is obtained. The virtual model can represent the implant designed to provide a correction to the patient's anatomy. The virtual model can be retrieved from, for example, a virtual model database, an implant design server, a digital filing cabinet, or other component of a system. In some embodiments, a manufacturing system (e.g., manufacturing 124 of FIG. 1) can obtain the implant virtual model from a client computing device (e.g., client computing device 102 of FIG. 1), database (e.g., database 110 of FIG. 1), server (e.g., server 106 of FIG. 1), or other component of the system 100 of FIG. 1. In some embodiments, the virtual model is received from CAD software, manufacturing software (e.g., additive manufacturing software, substrative manufacturing software, etc. running on the server 106 of FIG. 1), or the like.

The virtual model can be a two-dimensional or three-dimensional virtual model and can include, for example, CAD data, material data, surface modeling, manufacturing data, regulatory data, or the like. The CAD data can include, for example, solid modeling data (e.g., part files, assembly files, libraries, part/object identifiers, etc.), model geometry, object representations, parametric data, object representations, topology data, surface data, assembly data, metadata, etc. The material data can include, for example, material properties, material type, material manufacturing data (e.g., acceptable manufacturing techniques, manufacturing steps, etc.), or the like. The regulatory data can include, for example, governmental regulatory requirements, reimbursement requirements, etc. The object representations can be polygonal representations, boundary representations, etc. Details of examples for generating virtual models based on patient data are discussed in connection with FIG. 16.

At block 1420 (FIG. 14), manufacturing instructions can be generated for manufacturing systems capable of, for example, additive manufacturing, subtractive manufacturing, or other manufacturing techniques. The system can analyze manufacturability of the implant based on the virtual model, alter implant characteristics (e.g., modify virtual model geometry, dimensions, features, topology, composition, etc.), and then generate the manufacturing instructions according to the modified virtual model. In some embodiments, the system can identify potential implant characteristics to be modified such that the modified implant meets a manufacturable design match score. The manufacturable design match score can indicate matching of bone-contacting features, corrections, biomechanics, etc. A user can select the manufacturable design match score (or other scores) based on, for example, one or more dimensions between surfaces (e.g., opposing load bearing surfaces), topology (e.g., topology of bone-interfacing surfaces, retention mechanism interfacing surfaces, etc.), configuration of features for receiving additional components (e.g., retention mechanisms, anchors, screws, etc.), implant biomechanics, etc. Details of example manufacturing instructions are discussed in connection with FIG. 15.

At block 1430, a manufacturing system can manufacture the implant according to the manufacturing instructions. In additive manufacturing embodiments, an additive manufacturing machine can sequentially apply layers of material to form implants. For example, layers of the same material or different materials can be sequentially applied to form at least a portion of an implant (e.g., a one-piece unitary spacer body, a one-piece vertebral endplate of an articulating vertebral implant, etc.). In the same or different manufacturing process, additional features of the implant can be formed. For example, a one-piece body of the intervertebral spacer 402 of FIG. 5A can be formed and then the retention mechanisms 520*a*, 520*b* can be subsequently formed based on, for example, the manufacturing of the one-piece body. The manufacturing system can store manufacturing machine data (e.g., data generated by the manufacturing machine during manufacturing of the implant 405), images/scans of the implant 402, etc. to generate or modify manufacturing instructions for designing, modifying, and/or manufacturing the retention mechanisms. This allows for subsequently manufactured items to be designed, modified, and/or manufactured based on previously manufactured items.

Figure 15:
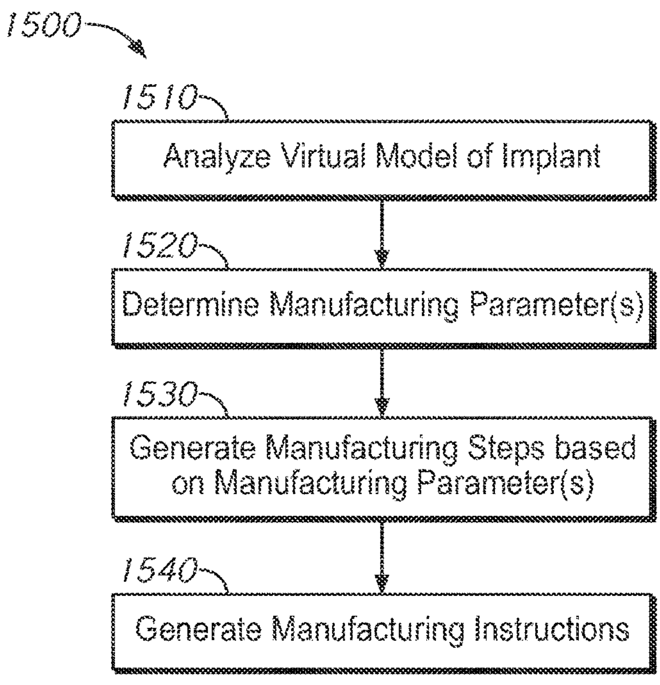
FIG. 15 is a flow diagram illustrating a method for generating manufacturing instructions in accordance with embodiments of the present technology.

FIG. 15 is a flow diagram illustrating a method 1500 for generating manufacturing instructions in accordance with embodiments of the present technology. The method 1500 can include analyzing a virtual model of an implant, determining manufacturing parameters based on the analysis, and generating manufacturing steps based on the manufacturing parameters. Manufacturing instructions can be generated based on the manufacturing steps. Manufacturing steps can be simulated, reordered, modified, or eliminated based on, for example, data collected during manufacturing, thereby providing real-time adaptive manufacturing. New or modified manufacturing instructions can be modified based on real-time modified manufacturing steps.

At block 1510, a virtual model of an implant is analyzed by, for example, analyzing regions of the virtual model and then generating manufacturing plans based on the analysis. The individually analyzed regions can be components, load-bearing features (e.g., regions or surfaces), discrete regions (e.g., slice-shaped regions), etc. In some embodiments, the virtual model is virtually sliced. For additive or subtractive manufacturing, the virtual model (or negative space surrounding the virtual model) can be partitioned for generating slice-shaped regions. The number, locations, and orientation of the virtual slices can be selected based on orientation-manufacturability of the virtual model. Additive or subtractive toolpaths can be planned based on the virtual slices. In additive manufacturing processes, the virtual model can be sliced to identify toolpaths for applying material. The spacing between slices can correspond to thicknesses of material layers that can be formed for each toolpath. For example, each virtual slice can represent one or more layers of applied material. In subtractive manufacturing processes, negative spaces around the virtual model can be sliced to identify toolpaths for removing material. Techniques for analyzing a virtual model can be selected based on the manufacturing technique and manufacturing equipment to be utilized.

At block 1520, manufacturing parameters are determined based on the implant analysis at block 1510. The manufacturing parameters can include, without limitation, order of manufacturing steps (e.g., order of manufacturing features or components of implant), orientation parameters (e.g., orientation of implant relative to the manufacturing machine, orientation of implant relative to toolpaths, etc.), material parameters (e.g., materials properties, composition of material, etc.), settings for equipment (e.g., manufacturing speeds, material application temperatures, etc.), or the like. In some multi-component implant embodiments, the manufacturing parameters can include component-toolpath orientations (e.g., vertical/horizontal orientation of components for vertical/horizontal toolpaths), material properties of the components, manufacturing steps for a manufacturing machine (e.g., tool path steps, manufacturing settings, etc.), or the like. For example, a virtual model can be sliced at different orientations to generate multiple slice datasets. The slice datasets can be analyzed to select an orientation of the implant with respect to the manufacturing equipment based on, for example, the position and orientation of patient-specific features of the implant, available toolpaths, etc.

At block 1530, manufacturing steps are generated based on the manufacturing parameter(s). The manufacturing steps can include, for example, establishing a coordinate system in which the virtual implant model is positioned. The system can then determine tool paths based on the coordinate system. For additive manufacturing, the manufacturing steps can include paths and print settings for three-dimensional printing, light settings for digital light processing, deposition settings for fused deposition melting, laser paths and deposition steps for selective laser melting, and other manufacturing steps for additive manufacturing. For subtractive manufacturing, the manufacturing steps can include tool paths and sequences for CNC machining, grinding tool orientations and paths for grinding, laser orientations and paths for laser cutting, pressures and tool paths for water jet cutting, or the like.

At block 1540, the manufacturing steps can be converted to manufacturing instructions. The manufacturing instructions can include code executable by manufacturing equipment. For example, the manufacturing instructions can be programs executable by manufacturing equipment (e.g., manufacturing equipment 124 of FIG. 1), additive manufacturing equipment, subtractive manufacturing equipment, or other manufacturing equipment. The manufacturing steps can optionally be converted to executable fabrication instructions configured to cause the manufacturing system to concurrently or sequentially manufacture features or components of the implant.

Figure 16:
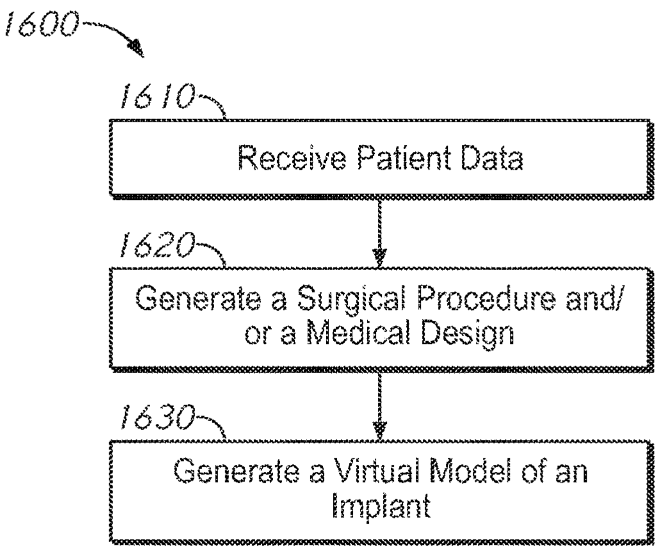
FIG. 16 is a flow diagram illustrating a method for generating a virtual model of an implant in accordance with embodiments of the present technology.

FIG. 16 is a flow diagram illustrating a method 1600 for generating a virtual model of an implant in accordance with embodiments of the present technology. Components can be designed based on other components of the implant. For example, a retention mechanism can be designed to couple to bony tissue using a virtual model of a spacer body or cage positioned along a virtual spinal model of the patient. The system can determine a number, orientations, and configurations of retention mechanisms based on, for example, the anatomical correction to be achieved. The sequence and protocols for designing components and features of implants can be selected by, for example, the system, a user, or both.

The method 1600 can include receiving a patient data set (block 1610). A subset of reference patient data can be selected, e.g., based on similarity to a patient data set and/or treatment outcomes of corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score. The patient data set can be compared to a plurality of reference patient data sets in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, segment flexibility, bone quality, rotational displacement, or treatment level of the spine.

In block 1620, a surgical procedure and/or medical device design is generated. The generating step can include developing at least one predictive model based on the patient data set and/or selected subset of reference patient data sets (e.g., using statistics, machine learning, neural networks, AI, or the like). The predictive model can be configured to generate the surgical procedure and/or medical design. In some embodiments, the predictive model includes one or more trained machine learning models that generate, at least partly, the surgical procedure and/or medical device design. In some embodiments, a user can generate the surgical procedure and/or medical device design based on inspection of the received patient data. Block 1620 can include a data analysis phase for identifying or determining, for at least one patient data set of the selected subset (e.g., for at least one similar patient data set), surgical procedure data and/or medical device design data associated with the favorable treatment outcome.

In block 1630, a virtual model of the implant is generated. The virtual model can be designed to fit a virtual anatomical model of the patient. Virtual models of implant components can be based on designs of other implant components. For example, virtual models of retention mechanisms can be designed after designing a spacer body or cage. This allows load-bearing components (or features) to be designed before anchoring components. Systems can determine the number, orientations, and configurations of the retention mechanisms. In other embodiments, anchoring components are designed prior to designing of load-bearing components. The order and sequence in which implant components and features are designed can be selected by the system, user, or a combination of both.

E. SELECT DEVICES AND METHODS FOR IMPLANTING PATIENT-SPECIFIC SPINAL FUSION DEVICES

Figure 17:
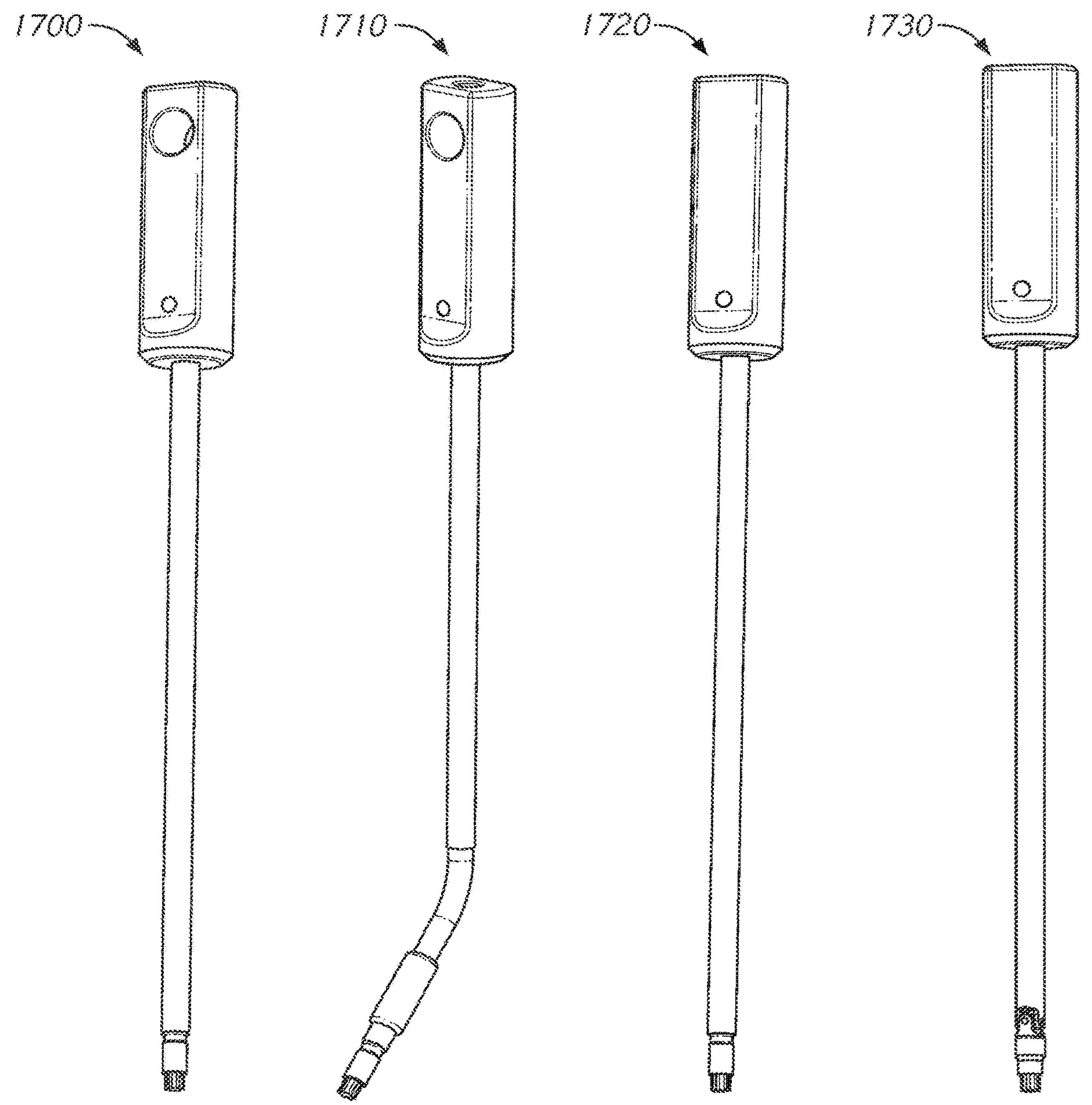
FIG. 17 illustrates four delivery devices configured in accordance with select embodiments of the present technology

In some embodiments, the present technology includes devices/instruments for implanting patient-specific spinal fusion devices, such as those described with reference to FIGS. 4-13B. For example, FIG. 17 illustrates four delivery devices configured in accordance with select embodiments of the present technology. More specifically, FIG. 17A illustrates an inserter device 1700, an angled awl 1710, a driver 1720, and a U-joint driver 1730. The inserter 1700 can be coupled to an anterior face of the implant (e.g., via a threaded connection) and used to deliver the implant to a target location. Once the implant is implanted and the location of the implant is verified (e.g., using an imaging system or technique), the inserter 1700 can be decoupled from the implant (e.g., by rotating it counterclockwise to disengage the threaded connection between the inserter 1700 and the implant). The angled awl 1710 has an angled distal end portion which can be used to prepare screw pilot holes (e.g., by extending the angled distal end portion of the angled awl 1710 through the screw holes or lumens on the implant and drilling a pilot hole in adjacent bony structure). The driver 1720 and/or the U-joint driver 1730 can be used to load fixation elements (e.g., screws) into the implant and through the pilot holes created by the angled awl 1710.

In some embodiments, the present technology includes surgical kits that include a patient-specific spinal fusion system (e.g., the device 400) and one or more delivery instruments, such as any of the instruments described with reference to FIG. 17. In such embodiments, one or more of the delivery devices 1700-1730 can be patient-specific and/or have patient-specific aspects. In other embodiments, however, one or more of the delivery devices 1700-1730 can be standardized for use with multiple different patient-specific spinal fusion systems. Moreover, the delivery devices 1700-1730 are provided by way of example only—in some embodiments, the patient-specific spinal fusions systems described herein can be implanted using other suitable delivery instruments.

F. EXAMPLES

Several aspects of the present technology are set forth in the following examples:

1. A patient-specific spinal fusion device, the device comprising:
   - an interbody implant configured to be positioned between a superior vertebral body and an inferior vertebral body, the interbody implant including
     - a superior surface configured to contact an inferior surface of the superior vertebral body,
     - an inferior surface configured to contact a superior surface of the inferior vertebral body, and
     - an anterior surface;
   - a first lumen extending through the implant between a first aperture in the anterior surface and a second aperture in the superior surface, wherein the first lumen is configured to receive a first fixation element for anchoring the implant to the superior vertebral body;
   - a second lumen extending through the implant between a third aperture in the anterior surface and a fourth aperture in the inferior surface, wherein the second lumen is configured to receive a second fixation element for anchoring the implant to the inferior vertebral body;
   - a rotatable retention mechanism configured to retain the first fixation element and the second fixation element in the implant, the rotatable retention mechanism including
     - a head defining one or more drive features for rotating the retention mechanism,
     - a shaft extending from the head and into to the implant, and
     - a ridge extending partially around a circumference of the shaft; and
   - a retention mechanism lumen configured to receive the shaft, wherein the retention mechanism lumen includes a channel extending partially around a circumference of the lumen for receiving the ridge,
   - wherein the rotatable retention mechanism is rotatable between (i) an unlocked configuration in which the head does not block the first aperture and the second aperture, and (ii) a locked configuration in which the head at least partially covers the first aperture and the second aperture, and wherein a degree of rotation between the unlocked configuration and the locked configuration is defined based at least in part on the ridge and the channel.

2. The device of example 1 wherein the ridge has a first circumferential length and the channel has a second circumferential length greater than the first circumferential length such that the ridge can rotate within the channel.

3. The device of example 2 wherein a difference between the first circumferential length and the second circumferential length defines the degree of rotation between the unlocked configuration and the locked configuration.

4. The device of any of examples 1-3 wherein the ridge extends around between about 90 degrees and about 270 degrees of the circumference of the shaft, and wherein the channel extends around between about 180 degrees and about 325 degrees of the circumference of the retention mechanism lumen.

5. The device of any of examples 1-3 wherein the ridge extends around about 180 degrees of the circumference of the shaft, and wherein the channel extends around about 270 degrees of the circumference of the retention mechanism lumen.

6. The device of example 5 wherein shaft is configured to rotate about 90 degrees between the unlocked configuration and the locked configuration.

7. The device of any of examples 1-6 wherein:
   - the ridge extends between a first surface and a second surface; and
   - the channel extends between a first channel wall and a second channel wall,
   - wherein
     - when the retention mechanism is in the unlocked configuration, the first surface is proximate the first channel wall, and
     - when the retention mechanism is in the locked configuration, the second surface is proximate the second channel wall.

8. The device of example 7 wherein:
   - the first channel wall permits the retention mechanism to rotate in only a first direction when the retention mechanism is in the unlocked position,
   - the second channel wall permits the retention mechanism to rotate in only a second direction when the retention mechanism is in the locked position, and
   - the first direction is opposite the second direction.

9. The device of any of examples 1-8 wherein the ridge has a height that is between about 20% and about 80% of a diameter of the shaft.

10. The device of any of examples 1-9 wherein the patient-specific spinal fusion device is configured to provide a patient-specific correction to a patient's spine when the patient-specific spinal fusion device is implanted in the patient.

11. the Device of Any of Examples 1-10 Wherein the Patient-specific Spinal fusion device is an ALIF device.

12. A patient-specific spinal fusion device, the device comprising:

an interbody implant configured to be positioned between a superior vertebral body and an inferior vertebral body, the interbody implant including
a superior surface configured to contact an inferior surface of the superior vertebral body,
an inferior surface configured to contact a superior surface of the inferior vertebral body, and
an anterior surface;
a first lumen extending through the implant between a first aperture in the anterior surface and a second aperture in the superior surface, wherein the first lumen is configured to receive a first fixation element for anchoring the implant to the superior vertebral body;
a second lumen extending through the implant between a third aperture in the anterior surface and a fourth aperture in the inferior surface, wherein the second lumen is configured to receive a second fixation element for anchoring the implant to the inferior vertebral body;
a rotatable retention mechanism configured to retain the first fixation element and the second fixation element in the implant, the rotatable retention mechanism including
a head defining one or more drive features for rotating the retention mechanism, and
a shaft extending from the head and into to the implant, wherein the shaft includes a projection extending transverse to a longitudinal axis of the shaft; and
a retention mechanism lumen configured to receive the shaft, wherein the retention mechanism lumen includes at least a first groove and a second groove,
wherein the rotatable retention mechanism is rotatable between (i) an unlocked configuration in which the head does not block the first aperture and the second aperture and in which the projection is in the first groove, and (ii) a locked configuration in which the head at least partially covers the first aperture and the second aperture and in which the projection is in the second groove.

13. The device of example 12 wherein the projection is configured to at least partially restrict rotational movement of the retention mechanism when the projection is in the first groove or the second groove.

14. The device of example 12 or example 13 wherein the unlocked configuration and the locked configuration are relatively low energy states, and wherein the device is configured such that transitioning the retention mechanism between the unlocked configuration and the locked configuration includes passing the retention mechanism through a relatively higher energy state.

15. The device of any of examples 12-14 wherein the retention mechanism lumen includes a third groove, and wherein the rotatable retention mechanism is rotatable through an intermediate configuration between the unlocked configuration and the locked configuration, and wherein the projection is in the third groove when the retention mechanism is in the intermediate configuration.

16. The device of any of examples 12-15 wherein the shaft includes at least two prongs spaced at least partially apart by a gap.

17. The device of example 16 wherein the projection is formed on at least one of the two prongs.

18. The device of example 16 or example 17 wherein each of the at least two prongs includes a projection.

19. The device of any of examples 16-18 wherein the at least two prongs include a back surface configured to abut a step of the retention mechanism lumen.

20. The device of any of examples 12-19 wherein the patient-specific spinal fusion device is configured to provide a patient-specific correction to a patient's spine when the patient-specific spinal fusion device is implanted in the patient.

21. The device of any of examples 12-20 wherein the patient-specific spinal fusion device is an ALIF device.

22. A spinal implant comprising:
a patient-specific interverbal spacer having a one-piece unitary spacer body including:
a first face configured to contact a first endplate of a first vertebra of a patient,
a second face configured to contact a second endplate of a second vertebra of the patient,
a sidewall, and
a first anchor channel extending from the sidewall to the first face, wherein a contoured portion of the first face surrounds an exit opening of the first anchor channel, wherein the contoured portion has irregular contours configured to match contours of a contoured region of the first endplate; and
a first screw configured to extend through the first anchor channel, out the exit opening, and into the first vertebra such that the first screw fixedly holds the contoured portion against of the contoured region of the first endplate.

23. The spinal implant of example 22, wherein the contoured portion comprises layers of material that define an endplate contact surface at the first face, and wherein the layers of material are fused, melted, and/or bonded together.

24. The spinal implant of example 22 or example 23, wherein
the first anchor channel includes a tubular sidewall defining a continuous surface extending from an entrance opening at the sidewall to the exit opening,
the one-piece unitary spacer body has a dense load-bearing portion and a porous portion coupling the tubular sidewall to the dense load-bearing portion, and
the dense load-bearing portion is configured to bear a majority of the loading applied by the subject's spine when the subject stands upright.

25. The spinal implant of example 24, wherein a mass of the dense load-bearing portion is majority of the total mass of the one-piece unitary spacer body.

26. The spinal implant of any of examples 22-25, wherein the one-piece unitary spacer body further includes a second anchor channel extending from the sidewall to the second face, the spinal implant further including:
a retention mechanism rotatably coupled to the one-piece unitary spacer body and rotatable between an unlocked position for allowing the first screw to be inserted into the first anchor channel and a second screw to be inserted into the second anchor channel and a locked position for captively holding the first and second screws in the first and second anchor channels, respectively.

27. The spinal implant of any of examples 22-26, wherein the one-piece unitary spacer body is asymmetrical with respect to a mid-sagittal plane of the one-piece unitary spacer and is asymmetrical with respect to a transverse plane of the one-piece unitary spacer.

28. A method of manufacturing, comprising:
obtaining a virtual model of a patient-specific interverbal spacer configured to be implanted between adjacent vertebrae of a patient;
generating additive manufacturing instructions based on the virtual model; and sequentially applying, using a manufacturing machine executing the additive manufacturing instructions, layers of material to form at least a portion of a one-piece unitary spacer body of the patient-specific interverbal spacer, and a retention mechanism configured to be assembled with the one-piece unitary spacer body, wherein the retention mechanism is rotatable between a screw insertion position and a locked screw position.

29. The method of example 28, further comprising designing the retention mechanism based on a design of the one-piece unitary spacer body.

30. The method of example 28 or example 29, further comprising using the virtual model of the one-piece unitary spacer body positioned along a virtual model of the adjacent vertebrae to design the retention mechanism.

31. The method of any of examples 28-30, further comprising:

determining an orientation of the patient-specific interverbal spacer to be manufactured with respect to orientations of the layers of material to be applied; and generating a plurality of toolpaths for concurrently forming a section of the one-piece unitary spacer body and a section of the retention mechanism.

32. The method of any of examples 28-31, further comprising:

determining a first set of toolpaths for forming a section of the one-piece unitary spacer body; and determining a second set of toolpaths for forming one or more locking cams, wherein the first and second sets of toolpaths are designed for execution by a single additive manufacturing machine or by multiple additive manufacturing machines.

33. The method of any of examples 28-32, further comprising determining a manufacturing orientation of the patient-specific interverbal spacer based on one or more potential tool paths for manufacturing one or more load-bearing surfaces of the patient-specific interverbal spacer.

34. The method of any of examples 28-33, further comprising layer-by-layer forming of non-planar load-bearing surfaces of the one-piece unitary spacer body.

35. The method of any of examples 28-34, further comprising:

slicing the virtual model; and generating an additive manufacturing path plan for the manufacturing machine to apply the layers of material based on the slicing.

36. The method of any of examples 28-35, further comprising:

designing one or more porous regions of the patient-specific interverbal spacer;

designing one or more non-porous regions of the patient-specific interverbal spacer; and analyzing the one or more porous regions and the one or more non-porous regions to generate additive manufacturing instructions.

37. The method of any of examples 28-36, further comprising:

establishing a coordinate system;

positioning the virtual model using the coordinate system; and determining toolpaths for the manufacturing machine to apply the layers of material of the virtual model positioned using the coordinate system.

38. A patient-specific interverbal spacer made by a process comprising:

obtaining a virtual model of a patient-specific interverbal spacer configured to be implanted between adjacent vertebrae of a patient;

generating additive manufacturing instructions based on the virtual model; and sequentially applying, using a manufacturing machine executing the additive manufacturing instructions, layers of material to form at least a portion of a one-piece unitary spacer body of the patient-specific interverbal spacer, and a retention mechanism configured to be assembled with the one-piece unitary spacer body, wherein the retention mechanism is rotatable between a screw insertion position and a locked screw position, and manufacturing the portion of a one-piece unitary spacer body and the retention mechanism.

39. The patient-specific interverbal spacer of example 38, wherein the patient-specific interverbal spacer comprises a layer-by-layer microstructure.

G. CONCLUSION

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2018, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/352,699, filed on Mar. 13, 2019, titled "SYSTEMS AND METHODS FOR ORTHOPEDIC IMPLANT FIXATION;"

U.S. application Ser. No. 16/383,215, filed on Apr. 12, 2019, titled "SYSTEMS AND METHODS FOR ORTHOPEDIC IMPLANT FIXATION;"

U.S. application Ser. No. 16/569,494, filed on Sep. 12, 2019, titled "SYSTEMS AND METHODS FOR ORTHOPEDIC IMPLANTS;" and U.S. application Ser. No. 16/699,447, filed Nov. 29, 2019, titled "SYSTEMS AND METHODS FOR ORTHOPEDIC IMPLANTS;"

U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS;"

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS;"

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS;"

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS;"

U.S. application Ser. No. 17/100,396, filed Nov. 20, 2020, titled "PATIENT-SPECIFIC VERTEBRAL IMPLANTS WITH POSITIONING FEATURES;"

U.S. application Ser. No. 17/342,439, filed Jun. 8, 2021, titled ""PATIENT-SPECIFIC MEDICAL PROCEDURES AND DEVICES, AND ASSOCIATED SYSTEMS AND METHODS;"

U.S. application Ser. No. 17/463,054, filed Aug. 31, 2021, titled "BLOCKCHAIN MANAGED MEDICAL IMPLANTS;"

U.S. application Ser. No. 17/518,524, filed Nov. 3, 2021, titled "PATIENT-SPECIFIC ARTHROPLASTY DEVICES AND ASSOCIATED SYSTEMS AND METHODS;"

U.S. application Ser. No. 17/531,417, filed Nov. 19, 2021, titled "PATIENT-SPECIFIC JIG FOR PERSONALIZED SURGERY;"

U.S. application Ser. No. 17/678,874, filed Feb. 23, 2022, titled "NON-FUNGIBLE TOKEN SYSTEMS AND METHODS FOR STORING AND ACCESSING HEALTHCARE DATA;"

U.S. application Ser. No. 17/835,777, filed Jun. 8, 2022, titled "PATIENT-SPECIFIC EXPANDABLE INTERVERTEBRAL IMPLANTS;"

U.S. application Ser. No. 17/842,242, filed Jun. 16, 2022, titled "PATIENT-SPECIFIC ANTERIOR PLATE IMPLANTS;"

U.S. application Ser. No. 17/851,487, filed Jun. 28, 2022, titled "PATIENT-SPECIFIC ADJUSTMENT OF SPINAL IMPLANTS, AND ASSOCIATED SYSTEMS AND METHODS;"

U.S. application Ser. No. 17/856,625, filed Jul. 1, 2022, titled "SPINAL IMPLANTS FOR MESH NETWORKS;"

U.S. application Ser. No. 17/867,621, filed Jul. 18, 2022, titled "PATIENT-SPECIFIC SACROILIAC IMPLANT, AND ASSOCIATED SYSTEMS AND METHODS;"

U.S. application Ser. No. 17/868,729, filed Jul. 19, 2022, titled "SYSTEMS FOR PREDICTING INTRAOPERATIVE PATIENT MOBILITY AND IDENTIFYING MOBILITY-RELATED SURGICAL STEPS;"

U.S. application Ser. No. 17/951,085, filed Sep. 22, 2022, titled "SYSTEMS FOR MANUFACTURING AND PRE-OPERATIVE INSPECTING OF PATIENT-SPECIFIC IMPLANTS;"

U.S. application Ser. No. 17/978,673, filed Nov. 1, 2022, titled "SPINAL IMPLANTS AND SURGICAL PROCEDURES WITH REDUCED SUBSIDENCE, AND ASSOCIATED SYSTEMS AND METHODS;"

U.S. application Ser. No. 17/978,746, filed Nov. 1, 2022, titled "PATIENT-SPECIFIC SPINAL INSTRUMENTS FOR IMPLANTING IMPLANTS AND DECOMPRESSION PROCEDURES;"

U.S. application Ser. No. 18/102,444, filed Jan. 27, 2023, titled "TECHNIQUES TO MAP THREE-DIMENSIONAL HUMAN ANATOMY DATA TO TWO-DIMENSIONAL HUMAN ANATOMY DATA;"

U.S. application Ser. No. 18/113,573, filed Feb. 24, 2023, titled "PATIENT-SPECIFIC IMPLANT DESIGN AND MANUFACTURING SYSTEM WITH A DIGITAL FILING CABINET;"

U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME;"

U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS;"

U.S. application Ser. No. 18/384,762, filed Oct. 28, 2023, titled "SYSTEMS AND METHODS FOR SELECTING, REVIEWING, MODIFYING, AND/OR APPROVING SURGICAL PLANS;"

U.S. application Ser. No. 18/537,600, filed Dec. 12, 2023, titled "PATIENT-SPECIFIC IMPLANT DESIGN AND MANUFACTURING SYSTEM WITH A REGULATORY AND REIMBURSEMENT MANAGER;"

U.S. Application No. 63/437,966, filed Jan. 9, 2023, titled "SYSTEM FOR EDGE CASE PATHOLOGY IDENTIFICATION AND IMPLANT MANUFACTURING;"

U.S. Application No. 63/437,975, filed Jan. 9, 2023, titled "SYSTEM FOR MODELING PATIENT SPINAL CHANGES;"

U.S. Application No. 63/522,815, filed Jun. 23, 2023, titled "SYSTEMS AND METHODS FOR DIAGNOSING SPINAL CONDITIONS AND DETERMINING TREATMENT OF THE SAME;"

U.S. Application No. 63/530,427, filed Aug. 2, 2023, titled "MEDICAL DEVICE INSERTER INSTRUMENTS WITH RETRACTABLE COUPLING ELEMENTS AND METHODS OF USING THE SAME;" and U.S. Application No. 63/542,264, filed Oct. 3, 2023, titled "PATIENT-SPECIFIC SURGICAL POSITIONING GUIDES AND METHODS OF MAKING AND USING THE SAME."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A patient-specific spinal interbody implant, comprising:

a tapered cage body configured to be delivered anteriorly into spine of a subject, the tapered cage body is asymmetrical with respect to a mid-sagittal plane of the tapered cage body and is asymmetrical with respect to a transverse plane of the tapered cage body, wherein the tapered cage body is configured to receive an anchor configured to anchor the tapered cage body to the spine and includes a first patient-specific endplate having a patient-contoured region, a lattice region beneath the patient-contoured region, a load bearing rim extending at least partially circumferentially about the patient-contoured region, wherein the load bearing rim includes a concave section and a convex section, wherein the patient-contoured region protrudes away from the transverse plane and past the concave section of the load bearing rim such that the patient-contoured region is positioned within a concave region of a first vertebral endplate of the spine and abuts a concave region of a vertebral surface of the spine when the tapered cage body is positioned between the first vertebral endplate and a second vertebral endplate of the spine;

a second patient-specific endplate, continuous smooth tubular surface defining an anchor-receiving throughhole extending through the tapered cage body, and one or more struts connected to the continuous smooth tubular surface and extending between the first patient-specific endplate and the second patient-specific endplate.

2. The patient-specific spinal interbody implant of claim 1, wherein the second patient-specific endplate with contours different from contours of the first patient-specific endplate.

3. The patient-specific spinal interbody implant of claim 1, wherein the tapered cage body includes one or more lattice regions extending along most of a distance between the first patient-specific endplate and a patient-specific second endplate.

4. The patient-specific spinal interbody implant of claim 1, wherein the tapered cage body has a graft holding chamber and a sidewall surrounding the graft holding chamber, wherein the sidewall includes a viewing lattice extending through the sidewall and defining a portion of the graft holding chamber.

5. The patient-specific spinal interbody implant of claim 1, further comprising:

an anchor configured to be positioned within the anchor-receiving throughhole to extend through an irregular patient-specific contoured surface of the first patient-specific endplate.

6. The patient-specific spinal interbody implant of claim 1, wherein the tapered cage body includes a continuous lumen defining the anchor-receiving throughhole that is tubular and arcuate.

7. A patient-specific spinal interbody implant, comprising:

a cage body configured to be delivered into spine of a subject, the cage body is asymmetrical with respect to a mid-sagittal plane of the cage body and is asymmetrical with respect to a transverse plane of the cage body, wherein the cage body includes a first patient-specific endplate having a patient-contoured region, an interior region including a plurality of solid regions and a plurality of lattice regions, wherein each of the solid regions is located between a respective pair of the lattice regions, and an outer solid rim defining a continuous surface extending along a periphery of the interior region, wherein the outer solid rim includes a concave section and a convex section, wherein the patient-contoured region protrudes outwardly past the concave section, and an anchor-receiving throughhole extending through the cage body and the patient-contoured region; and an anchor configured to be positioned within the anchor-receiving throughhole and to extend through the first patient-specific endplate and a first vertebral endplate of the spine of the subject such that the patient-contoured region is positioned along the first vertebral endplate when the cage body is positioned between the first vertebral endplate and a second vertebral endplate of the spine.

8. The patient-specific spinal interbody implant of claim 7, further comprising a second patient-specific endplate with contours different from contours of the first patient-specific endplate.

9. The patient-specific spinal interbody implant of claim 7, wherein the cage body includes one or more lattice regions extending along most of a distance between the first patient-specific endplate and a patient-specific second endplate.

10. The patient-specific spinal interbody implant of claim 7, wherein the cage body has a graft holding chamber and a sidewall surrounding the graft holding chamber, wherein the sidewall includes a viewing lattice extending through the sidewall and defining a portion of the graft holding chamber.

11. A patient-specific spinal interbody implant comprising:

a cage body configured to be delivered into a spine of a patient, the cage body is asymmetrical with respect to a mid-sagittal plane of the cage body and is asymmetrical with respect to a transverse plane of the cage body, wherein the cage body includes a first patient-specific endplate having a patient-contoured region, a lattice region, an outer solid rim defining a continuous surface extending along a periphery of the first patient-specific endplate, wherein the outer solid rim includes a concave section and a convex section, wherein the patient-contoured region protrudes outwardly past the concave section, an anchor-receiving throughhole extending through the cage body and the patient-contoured region, a second patient-specific endplate, a continuous smooth tubular surface defining the anchor-receiving throughhole extending through the cage body, and one or more struts connected to the continuous smooth tubular surface and extending between the first patient-specific endplate and the second patient-specific endplate; and an anchor configured to be positioned within the anchor-receiving throughhole and to extend through the first patient-specific endplate and a first vertebral endplate of the spine of the patient such that the patient-contoured region is positioned along the first vertebral endplate when the cage body is positioned between the first vertebral endplate and a second vertebral endplate of the spine.

12. The patient-specific spinal interbody implant of claim 7, wherein the anchor-receiving throughhole has an arcuate lumen extending between the patient-contoured region and a sidewall opening of the cage body.

13. The patient-specific spinal interbody implant of claim 7, wherein the cage body includes a second patient-specific endplate opposite the first patient-specific endplate, and a solid corner region extending between the first patient-specific endplate and the second patient-specific endplate.

14. The patient-specific spinal interbody implant of claim 7, wherein the patient-contoured region extends across most of a side-to-side width of the cage body.

15. A patient-specific spinal interbody implant comprising:

a cage body including a first patient-specific endplate having a first patient-contoured region configured to contact a first endplate of a spine of a patient, a second patient-specific endplate having a second patient-contoured region configured to contact a second endplate of the spine, a first lattice region positioned between the first patient-specific endplate and the second patient-specific endplate, a second lattice region positioned between the first patient-specific endplate and the second patient-specific endplate, a continuous tubular portion defining an anchor-receiving throughhole extending through the cage body, and a strut extending between the first patient-specific endplate and the second patient-specific endplate, wherein the strut is positioned between the first lattice region and the second lattice region, and wherein the second lattice region is positioned between the strut and an entrance opening of the anchor-receiving throughhole.

16. The patient-specific spinal interbody implant of claim 15, further comprising an anchor configured to be positioned in the anchor-receiving throughhole such that the anchor extends into the first endplate of the spine and the continuous tubular portion is located directly between the anchor and the first lattice region.

17. The patient-specific spinal interbody implant of claim 15, further comprising:

an anchor, and a retention mechanism movable relative to the cage body between an unlocked configuration for allowing the anchor to be inserted through the anchor-receiving throughhole and a locked configuration for contacting a head of the anchor when the anchor is positioned in the anchor-receiving throughhole.

18. The patient-specific spinal interbody implant of claim 15, wherein the cage body further includes a graft opening extending between the first patient-specific endplate and the second patient-specific endplate, wherein the continuous tubular portion has a convex sidewall that extends toward a longitudinal axis of the graft opening and defines a portion of the graft opening.

19. The patient-specific spinal interbody implant of claim 18, wherein the graft opening is configured to be filled with graft material that promotes bone growth between the first endplate and the second endplate of the spine.

20. The patient-specific spinal interbody implant of claim 18, wherein a patient-contacting edge of the convex sidewall has a patient-specific topography that matches a topography of the first endplate.

21. The patient-specific spinal interbody implant of claim 15, wherein the first patient-specific endplate, the second patient-specific endplate, and the strut are integrally connected together.

22. The patient-specific spinal interbody implant of claim 21, wherein the strut extends between the first patient-specific endplate and the second patient-specific endplate.

23. A patient-specific spinal interbody implant comprising:

a cage configured to be implanted along a spine of a patient, the cage including a first endplate having a first patient-contoured region, a second endplate having a second patient-contoured region, an interior region between the first endplate and the second endplate and including plurality of solid regions and a plurality of lattice regions, wherein each of the plurality of solid regions is located between a respective pair of the plurality of lattice regions, and an anchor-receiving throughhole extending through the cage and the first patient-contoured region; and an anchor configured to be positioned within the anchor-receiving throughhole and to extend through the first endplate of the cage and a first anatomical endplate of the spine such that the first patient-contoured region is positioned along the first anatomical endplate.

24. The patient-specific spinal interbody implant of claim 23, wherein a tubular portion of one of the plurality of solid regions has a continuous smooth surface that defines the anchor-receiving throughhole.

25. The patient-specific spinal interbody implant of claim 24, wherein the cage further includes a graft opening extending between the first endplate and the second endplate, wherein the tubular portion has a convex sidewall that extends toward a central region of the graft opening and defines a portion of the graft opening.

26. The patient-specific spinal interbody implant of claim 25, wherein the graft opening is configured to be filled with graft material that promotes bone growth between bony anatomy of the spine.

27. The patient-specific spinal interbody implant of claim 25, wherein the convex sidewall has a patient-contacting edge with a patient-specific topography that matches a topography of the first anatomical endplate.

28. The patient-specific spinal interbody implant of claim 23, wherein the plurality of lattice regions includes a first lattice region and a second lattice region, and wherein the plurality of solid regions includes a strut positioned between the first lattice region and the second lattice region.

29. The patient-specific spinal interbody implant of claim 28, wherein the strut extends between the first endplate and the second endplate.

30. The patient-specific spinal interbody implant of claim 23, wherein the first endplate, the second endplate, and the interior region are integrally connected together.

31. An interbody implant comprising:

a first patient-specific endplate having a first patient-contoured region configured to contact a first endplate of a spine of a patient;

a second patient-specific endplate having a second patient-contoured region configured to contact a second endplate of the spine;

a lattice region positioned between the first patient-specific endplate and the second patient-specific endplate;

a strut positioned between the first patient-specific endplate and the second patient-specific endplate;

a graft opening extending between the first patient-specific endplate and the second patient-specific endplate; and a tubular portion defining an anchor-receiving throughhole extending through the interbody implant, wherein the tubular portion includes a convex sidewall that extends toward and defines a portion of the graft opening, and wherein the convex sidewall has a patient-contacting edge portion with a patient-specific topography that matches a topography of the first endplate.

* * * * *